(12) United States Patent
Ulf-Hakan et al.

(10) Patent No.: US 7,414,023 B2
(45) Date of Patent: Aug. 19, 2008

(54) PEPTIDE LIGANDS FOR PROSTATE SPECIFIC ANTIGEN

(75) Inventors: Stenman Ulf-Hakan, Kauniainen (FI); Erkki Koivunen, Helsinki (FI); Jari Leinonen, Helsinki (FI); Ale Närvänen, Kuopio (FI)

(73) Assignee: Licentia Ltd., Helsinki (FI)

( * ) Notice: Subject to any disclaimer, the term of this patent is extended or adjusted under 35 U.S.C. 154(b) by 610 days.

(21) Appl. No.: 10/363,662

(22) PCT Filed: Oct. 1, 2001

(86) PCT No.: PCT/FI01/00856

§ 371 (c)(1),
(2), (4) Date: Sep. 26, 2003

(87) PCT Pub. No.: WO02/26777

PCT Pub. Date: Apr. 4, 2002

(65) Prior Publication Data

US 2004/0106557 A1    Jun. 3, 2004

(30) Foreign Application Priority Data

Sep. 29, 2000   (FI)   ................................. 20002159

(51) Int. Cl.
*A61K 38/12* (2006.01)
*A61K 38/00* (2006.01)
*A61K 38/02* (2006.01)
*A61K 38/10* (2006.01)
*C07K 2/00* (2006.01)
*C07K 7/64* (2006.01)
*C07K 5/12* (2006.01)
*C07K 7/08* (2006.01)
*C07K 1/00* (2006.01)
*C07K 1/04* (2006.01)

(52) U.S. Cl. .................. 514/9; 514/2; 514/10; 514/11; 514/14; 530/300; 530/317; 530/327; 530/333

(58) Field of Classification Search ........................ None
See application file for complete search history.

(56) References Cited

FOREIGN PATENT DOCUMENTS

EP           0905142 A1      3/1999

OTHER PUBLICATIONS

L. Leinonen, et al. Scand. J. Clin. Lab. Invest. (2000) 60(233 Suppl), pp. 59-64.*
W.-M. Zhang, et al. Scand. J. Clin. Lab. Invest. (2000) 60(233 Suppl), pp. 51-58.*
P. Wu, et al. Eur. J. Biochem. (2000) 267, pp. 6212-6220.*
"Motif" On-line Medical Dictionary <<http://www.cancerweb.ncl.c/uk/od/>> 1 page; accessed Nov. 14, 2006.*
"Motif" Drug Discovery and Development Glossary <<http://www.ddmag.com/scripts/glossary.asp>>1 page, accessed Nov. 14, 2006.*
A.S. Edwards, et al. J. Biol. Chem. (1997) 272(29), pp. 18382-18390.*
Ravi P. Nargund, et al., Journal of Medicinal Chemistry vol. 41, No. 17, Aug. 13, 1998, pp. 3103-3127.
Wadih Arap, et al., Cancer Treatment by Target Drug Delivery to Tumor Vasculature in a Mouse Model vol. 279 Jan. 16, 1998.
U.-H. Stenman, et al., Summary Report of the TD-3 Workshop: Characterization of 83 Antibodies against Prostate-Specific Antigen Tumor Biol, 1999 vol. 20, No. 1, pp. 1-12.
M.C. Wang, et al., Purification Of A Human Prostate Specific Antigen, Mar. 26, 1979, pp. 159-163.
Hans Lilja, et al. Seminal Vesicle-Secreted Proteins and Their Reactions during Gelation and liquefaction of Human Semen, vol. 80 Aug. 1987, 281-285.
U.K. Laemmli., Cleavage of Structural Proteins during the Assembly of the Head of Bacteriophage T4 Nature, vol. 227, Aug. 15, 1970.
Harry Towbin, et al., Electrophoretic transfer of proteins from polyacrylamide gels to nitrocellulose sheets: Procedure and some applications, vol. 76, No. 9, Sep. 1979, pp. 4350-4354.
P. Guntert C. Mumenthaler, et al., Torsion Angle Dynamics for NMR Structure Calculation with the New Program Dyana, vol. 76, No. 9, Sep. 1979, pp. 283-298.
Gail Hutchinson, et al., A revised set of potentials for β-turn formation in proteins., vol. 3, Oct. 10, 1994 pp. 2207-2216.
B. H. Meier, et al., Investigation of exchange processes by two-dimensional NMR spectroscopy, vol. 71, No. 11, Dec. 1, 1979 pp. 4546-4553.
Allister J. Maynard, et al., Origin of β-Hairpin Stability in Solution: Structural and Thermodynamic Analysis of the Folding of a Model Peptide Supports Hydrophobic Stabilization in Water, vol. 120, 1998, pp. 1996-2007.
Lars Sottrup-Jensen, α-Macroglobulins: Structure, Shape, and Mechanism of Proteinase Complex Formation, vol. 264, No. 20, Jul. 15, 1989, pp. 11539-11542.
Hannu Koistinen, et al., Different Forms of Insulin-Like Growth Factor-Binding Protein-3 Detected in Serum and Seminal Plasma by Immunofluorometric Assay with Monoclonal Antibodies, vol. 40, No. 4, 1994.
Pinchas Cohen, et al., Prostate-Specific Antigen (PSA) is an Insulin-Like Growth Factor Binding Protein-3 Protease Found in Seminal Plasma, vol. 75, No. 4. 1992, pp. 1046-1053.
Janita Lovegren[1], et al., Production of Recombinant PSA And HK2 And Analysis Of Their Immunologic Cross-Reactivity, vol. 213, No. 3, Aug. 24, 1995, pp. 888-895.
Erkki Koivunen, et al., Human Ovarian Tumor-associated Trypsin, vol. 264, No. 24, Aug. 25, 1989, pp. 14095-14099.

(Continued)

*Primary Examiner*—Andrew D. Kosar
(74) *Attorney, Agent, or Firm*—Sughrue Mion, PLLC

(57) ABSTRACT

The present invention relates to novel peptide ligands for prostate specific antigen (PSA) binding specifically with it and enhancing its enzyme activity, to a process for preparation of these peptides, to diagnostic and pharmaceutical compositions comprising these peptides, to the use of these peptides for pharmaceutical and research preparations, to methods using these peptides in diagnostic assays for determination of the concentrations of various molecular forms of PSA, to methods for modulating the PSA enzyme activity and PSA activity dependent conditions by using these peptides either in vivo or in vitro and to the use of these peptides in procedures for biochemical isolation and purification of PSA.

9 Claims, 31 Drawing Sheets

OTHER PUBLICATIONS

Erkki Koivunen, et al., [17] Peptides in Cell Adhesion Research, 1994, pp. 347-369.

Daniel Rajotte, et al., Molecular Heterogeneity of the Vascular Endotherlium Revealed by in Vivo Phage Display, vol. 102, No. 2, Jul. 1998, pp. 430-437.

Vladimir A.Slepushkin, et al., Targeting of Liposomes to HIV-1-Infected Cells by Peptides Derived from the DC4 Receptor, vol. 227, 827-833 (1996), Article No. 1592.

Samuel Zalipsky, et al. Peptide Attachments to Extremities of Liposomal Surface Grafted PEG Chains: Preparation of the Long-Circulating Form of Laminin Pentapeptide, YIGSR, vol. 6, 1995, pp. 705-708.

Richard P. Harbottle, et al., An RGD-Oligolysine Peptide: A Prototype Construct for Integrin-Mediated Gene Delivery, vol. 9, May 1, 1998, pp. 1037-1047.

Richard A. Houghten, et al., Journal of Medicinal Chemistry, vol. 42, No. 19, Sep. 23, 1999 pp. 3743-3778.

Robert J. Fisher, et al., Surface plasmon resonance based methods for measuring the kinetics and binding affinities of biomolecular interactions, pp. 389-395.

Zuxiong Chen, et al., Prostate Specific Antigen In Benign Prostatic Hyperplasia: Purification and Characterization, vol. 157, Jun. 1997, pp. 2166-2170.

Stephen D. Mikolajczyk, et al., A Precursor Form of PSA (pPSA) Is A Component Of The Free PSA In Prostate Cancer Serum, vol. 50, 1997, pp. 710-714.

Ulf-Håkan Stenman, et al., A Complex between Prostate-specific Antigen and α1-Antichymotrypsin Is the Major Form of Prostate-specific Antigen in Serum of Patients with Prostatic Cancer: Assay of the Complex Improves Clinical Sensitivity for Cancer[1], vol. 51, Jan. 1, 1991, pp. 222-226.

Wan-Ming Zhang, et al., Purification and Characterization of Different Molecular Forms of Prostate-Specific Antigen in Human Seminal Fluid, vol. 41, No. 11, Jun. 27, 1995, pp. 1567-1573.

Sirkka-Liisa Karonen, et al., Localization of Human Malignant Tumors with Radioiodinatd Recombinant Tissue Plasminogen Activator, vol. 29, Jan. 27, 1988, pp. 1194-1199.

Ilkka Hemmilä, et al., Europium as a Label in Time-Resolved Immunofluorometric Assays, vol. 137, 1984, pp. 335-343.

Gary S. Coombs[1], et al., Substrate specificity of prostate-specific antigen (PSA), vol. 5, Sep. 1998, pp. 475-488.

Hans Lilja, et al., Semenogelin, the Predominant Protein in Human Semen, vol. 264, No. 3, Jan. 25, 1989, pp. 1894-1900.

Jamie K. Scott, et al., Searching for Peptide Ligands with an Epitope Library, vol. 249, Jun. 13, 1990, pp. 386-390.

Sibo Feng, et al., Specific interactions outside the proline-rich core of two classes of Src homology 3 ligands, vol. 92, Dec. 1995, pp. 12408-12415.

Bradley A. Katz, et al., Design of potent selective zinc-mediated serine protease inhibitors, vol. 391, Feb. 5, 1998, pp. 608-612.

Jeremy M. Berg, et al., The Galvanization of Biology: A Growing Appreciation for the Roles of Zinc, vol. 271, Feb. 23, 1996, pp. 1081-1085.

Wan-Ming Zhang, et al., Characterization and immunological determination of the complex between prostate-specific antigen and $\alpha^2$-macroglobulin, vol. 44, No. 12, Sep. 28, 1998, pp. 2471-2479.

Hans Lilja, et al., Seminal Vesicle-secreted Proteins and Their Reactions during Gelation and Liquefaction of Human Semen, vol. 80, Aug. 1987, pp. 281-285.

M.C. Wang, et al., Purification of a Human Prostate Specific Antigen[1], pp. 159-163.

U.-H. Stenman, et al., Summary Report of the TD-3 Workshop: Characterization of 83 Antibodies against Prostate-Specific Antigen, vol. 20, No. 1, 1999, pp. 1-12.

Wadih Arap, et al. Cancer Treatment by Targeted Drug Delivery to Tumor Vasculature in a Mouse Model, vol. 279, Jan. 16, 1998,.pp. 377-380.

Ravi P. Nargund, et al., Journal of Medicinal Chemistry, vol. 41, No. 17, Aug. 13, 1998, pp. 3104-3127.

Samuel R. Denmeade, et al., Enzymatic Activation of a Doxorubicin-Peptide Prodrug by Prostate-Specific Antigen[1], Vol. 58, Jun. 15, 1998, pp. 2537-2540.

Samuel R. Denmeade, et al., Specific and Efficient Peptide Substrates for Assaying the Proteolytic Activity of Prostate-specific Antigen[1], vol. 57, Nov. 1, 1997, pp. 4924-4930.

Geoffrey M. Gersuk, et al., High-Affinity Peptide Ligands to Prostate-Specific Antigen Identified by Polysome Selection, vol. 232, 1997, pp. 578-582.

Gregory P. Adams, et al., Generating improved single-chain Fv molecules for tumor targeting, vol. 231, 1999, pp. 249-260.

H-H Heidtmann, et al., Generation of angiostatin-like fragments from plasminogen by prostate-specific antigen, vol. 81, No. 8, Jun. 8, 1999 pp. 1269-1273.

Anne H. Fortier, et al., Antiangiogenic Activity of Prostate-Specific Antigen, vol. 91, No. 19, Oct. 6, 1999, pp. 1635-1640.

Donald B. Smith, et al., Single-step purification of polypeptides esxpressed in *Eshcerichia coli* as fusions with glutathione S-transferase, vol. 67, 1988, pp. 31-40.

J. Leinonen, et al., Reactivity of 77 Antibodies to Prostate-Specific Antigen with Isoenzymes and Complexes of Prostate-Specific Antigen, vol. 20, No. 1, 1999, pp. 28-34.

Outi Itkonen, et al., Time-resolved immunopfluorometric assays for trypsinogen-I and 2 in serum reveal preferential elevation of trypsinogen-2 in pancreatitis, vol. 115, 1990, pp. 712-718.

Jari Leinonen, et al., Double-Label Time-Resolved Immunofluorometric Assay of Prostate-Specific Antigen and of Its Complex with α1-Antichymotrypsin, vol. 39, No. 10, pp. 2098-2103.

J. Leinonen, et al., Reactivity of Anti-PSA Monoclonal Antibodies with Recombinant Human Kallikrein-2, vol. 20, No. 1, pp. 35-37.

Robert J. Fisher, et al., Surface plasmon resonance based methods for measuring the kinetics and binding affinities of biomolecular interactions, vol. 5, 1994, pp. 389-395.

Wan-Ming Zhang, et al., Prostate-Specific Antigen Forms a Complex With and Cleaves α1-Protease Inhibitor In Vitro, vol. 33, (1997), pp. 87-96.

D.S. Wart, et al., Relationship between Nuclear Magnetic Resonance Chemical Shift and Protein Secondary Structure, vol. 222, 1991, pp. 311-333.

S. Raghothama, et al., NMR Analysis of a Conformational Transition in an Acyclic Peptide. Model System for Studying Helix Unfolding, vol. 100, 1996, pp. 1966-19671.

Ad Bax, et al., MLEV-17-Based Two-Dimensional Homonuclear Magnetization Transfer Spectroscopy, vol. 65, 1985, pp. 355-360.

Scand J Clin Lab Invest, vol. 60, Suppl. 233, 2000, J Leinonen et al: "Development of Novel Peptide Ligands Modulating the Enzyme Activity of Prostate-Specific Antigen", pp. 59-64.

Eur J. Boichem, vol. 267, 2000, Ping Wu et al: "Identification of Novel Prostate-Specific Antigen-Binding Peptides Modulating its Enzyme Activity", pp. 6212-6220.

International Search Report for PCT/FI01/00856 dated Mar. 7, 2002.

\* cited by examiner

PEPTIDE LIGANDS FOR PROSTATE SPECIFIC ANTIGEN

CROSS-REFERENCE TO RELATED APPLICATION

This application is a 371 of PCT/FI01/00856, filed Oct. 1, 2001; the disclosure of which is incorporated herein by reference.

FIELD OF THE INVENTION

The present invention relates to novel peptide ligands for prostate specific antigen binding and for enhancing its enzyme activity. The present invention also relates to a process for the preparation of these peptides. Further, the present invention concerns pharmaceutical and diagnostic compositions comprising these peptides and the use of the peptides for pharmaceutical and diagnostic preparations. Still further, the present invention relates to the use of these peptides as medicaments and diagnostic agents, for the preparation of medicaments and diagnostic agents and in biochemical isolation and purification procedures.

DESCRIPTION OF RELATED ART

Prostate specific antigen (PSA) is a highly specific product of prostatic epithelial cells (1). PSA is a 30 kD serine protease, the main biological function of which is liquefaction of the seminal gel formed after ejaculation by proteolytic cleavage of the semenogelins, which are the major constituents of the seminal clot (2). PSA in seminal fluid mainly consists of free PSA including enzymatically active forms and proteolytically cleaved or nicked forms of PSA (3). In human serum, the major immunoreactive forms of PSA are the PSA-a1-antichymotrypsin complex (PSA-ACT) and free PSA (PSA-F) (4).

Measurement of serum PSA is widely used for detection and management of patients with prostate cancer and it is increasingly used for screening of this disease. The major problem in the use of PSA for screening is the high false positive rate caused by benign prostatic hyperplasia. This can be reduced by assaying the proportion of either PSA-ACT or free PSA in relation to total PSA (4) but further improvement in the cancer specificity of PSA is desirable. This may be accomplished by developing specific assays for minor variants of PSA. Prostate cancer cells preferentially secrete the proenzyme form of PSA (5), whereas nicked PSA has been shown to be formed in benign tissue (6). Thus, assays for these forms of PSA are of potential clinical utility, but development of monoclonal antibodies (MAbs) specific for these forms has been difficult. Another assay with diagnostic utility is that for the PSA-alpha-2-macroglobulin complex (PSA-A2M) (7). However, in this complex binding agents with high molecular weight like antibodies cannot access PSA because the inhibitor encapsulates the proteinase. Thus, assay of PSA-A2M requires denaturation of the complex (7). Development of direct assay for PSA-A2M would require a small binding agent entering the inhibitor and recognizing specifically PSA.

PSA may inhibit tumor growth (8) and has recently been shown to generate angiostatin from plasminogen (9). Because angiostatin inhibits tumor growth by preventing formation of new blood vessels in the tumor, generation of angiostatin may retard tumor development. Thus, agents modulating the enzyme activity of PSA could be potentially useful in treatment of prostate cancer.

MAbs are widely used tools for imaging and treatment of cancer. However, the large size of MAbs limits their ability to diffuse from circulation into tissues. Furthermore, mouse antibodies are immunogenic in humans, which limits their use for therapy. MAbs may also exhibit a prolonged availability in circulation and interact with Fc receptors in normal tissues, endangering the patient when toxins or radioisotopes are attached (10). These problems can be eliminated by using alternative small molecular weight binding agents.

An alternative to MAbs in the development of specific binding agents is to use peptide libraries and phage display techniques. PSA-binding peptides have been produced before by the polysome selection method (11), but these peptides did not modulate the enzyme activity of PSA and were not shown to be useful as part of assays for PSA. Denmeade et al. have developed peptide substrates for PSA on the basis of the sequence of semenogelin, which is the substrate for PSA in seminal fluid (12). However, these peptides cannot be applied in techniques in which stable binding to PSA is required.

Although the above discussion shows that some peptides reacting with PSA have been developed they have not been shown to modulate the enzyme activity of PSA or be functional in applications for detection of PSA.

SUMMARY OF THE INVENTION

It is an object of the present invention to eliminate the problems of the prior art and to provide novel PSA binding chemical agents. In particular, the invention aims at providing novel peptide ligands and functional equivalents thereof which are therapeutically and diagnostically useful in particularly for treatment and diagnosis of conditions involving release of PSA into serum.

It is another object to provide a process for the preparation of novel peptide ligands for prostate specific antigen which are capable of modulating its enzyme activity.

It is a third object to provide pharmaceutical and diagnostic compositions comprising novel chemical compounds capable of binding to PSA.

Further, it is a fourth object of the invention to provide novel diagnostic and therapeutical methods.

These and other objects, together with the advantages thereof over known binding agents and processes, are achieved by the present invention as hereinafter described and claimed.

The present invention is based on the finding that a group of novel peptides having a specific structure (specific amino acid sequences or motifs) are capable of selectively binding to free PSA or to PSA in complex with A2M and of modulating its enzymatic activity. The peptides of the invention comprise at least one pair of cysteines which are spaced apart by a number of at least two amino acids and which are capable of forming a cyclic structure in which there is a disulphide bond between said at least one pair of cysteines. As a result of the disulphide bonding between the cysteines, the main chain of the peptide is bent and it takes up a 3-dimensional conformation, which can be used as a basis for development of peptidyl analogues or peptidomimetic compounds having similar bioactivity as the peptides.

The novel peptides, which illustrate the present binding agents, have been found by using phage display libraries of peptides that were conformationally restrained by designed disulfide bonds. Surprisingly, and quite contrary to expectations, the most active peptides enhance the enzyme activity of PSA against small molecular weight chromogenic substrates and natural protein substrates. This increased activity of PSA can be utilized in a number of applications in particular when enhancement of the enzymatic activity of PSA is used for therapeutic purposes.

More specifically, the peptide ligands and functional equivalents thereof according to the present invention are mainly characterized by what is stated in the characterizing parts of the following:

1. Binding agent for prostate specific antigen, comprising
   a. a peptide having at least 6 amino acids bonded together to form a peptide backbone 5 and including at least one pair of cysteines which are spaced apart by a number of at least two amino acids and interconnected by a disulfide bond to form a cyclic structure defined by the cysteines, the intermediary amino acids and the disulfide bond; or
   b. a peptidomimetic compound having a spatial conformation similar to the peptide, said peptide or peptidomimetic compound exhibiting selective binding to free prostate specific antigen.
2. The binding agent according to 1, wherein the peptide backbone comprising at least two pairs of cysteines interconnected by disulfide bonds.
3. The binding agent according to 2, wherein the peptide is capable of enhancing the enzymatic activity of the prostate specific antigen.
4. Peptide motifs or sequences according to formula (I) $CX^1X^2XXXX^6XXC$ wherein $X^1$ is V or I, $X^2$ is F, I, W or P, $X^6$ is Y, N or L, C is cysteine, and each X stands independently for an amino acid residue.
5. The peptide motifs or sequences according to 4, wherein $X^1$ is V or I, $X^2$ is F or I and $X^6$ is Y or N.
6. The peptide motifs or sequences according to 4, wherein X1 is V, X2 is F, X~ is Y and each X is an amino acid residue independently selected from the group consisting of T, S, D, Y, A, F, E, P, and L.
7. The peptide motifs or sequences according to 4, wherein XI is V, X2 is I, X6 is N and each X is an amino acid residue independently selected from the group consisting of Y, D, G, H, W, P, and V.
8. The peptide motifs or sequences according to 4, wherein $X^1$ is I, $X^2$ is F, $X^6$ is Y or N, and each X is art amino acid residue independently selected from the group consisting of E, P, D, S, Y, G, F, I and L.
9. The peptide motifs or sequences according to 4, wherein $X^1$ is V or I, $X^2$ is F, I, W or P, $X^5$ is D or N, $X^6$ is Y, N or L, $X^7$ is A or N, Xs is F or Y, the remaining structural units beating the same meanings as in 4.
10. Peptide motifs or sequences according to formula (1I) $CX^1X^2XXXX^6XX^8X^9X^{10}C$ wherein $X^1$ is V, T or R, $X^2$ is F, $X^6$ is Y, $X^8$ is Y or T, X9 is L, $X^{10}$ is V or M, and X and C have the same meaning as in 1.
11. The peptide motifs or sequences according to 10, wherein $X^1$ is V, $X^2$ is F, $X^6$ is Y, $X^8$ is Y, $X^9$ is L, $X^{10}$ is V and X is selected from the group consisting of A, H, N and D.
12. The peptide motifs or sequences according to 11, wherein $X^1$ is V, T, or R, $X^2$ is F, $X^6$ is Y, $X^7$ is D or N, $X^8$ is Y, T or A, $X^9$ is L, $X^{10}$ is V or M, and the other units bearing the same meanings as in 11.
13. Peptide motifs or sequences according to formula (III) $CX^1X^1X^3CXXXXCX^8X^9C$ wherein $X^1$ is V or A, $X^2$ is A, S, E, T, V or Q, $X^3$ is Y, $X^8$ is Y or W, $X^9$ is V, T, M, Y, G or F and X and C have the same meaning as in 1.
14. The peptide motifs or sequences according to 13, wherein $X^1$ is V, $X^2$ is A or S, $X^3$ is Y, $X^8$ is Y or W, $X^9$ is V, Y or T, and each X is independently selected from the group consisting of L, F, E, W, G, S, I, H, D, G, L, Q, Y, V, A, M and K.
15. The peptide motifs or sequences according to 13 or 14, wherein $X^1$ is V, $X^2$ is A and $X^3$ is Y.
16. The peptide motifs or sequences according to 13, wherein $X^3$ is Y or F and $X^5$ is E or Q, the remaining structural units having the same meanings as in 13.
17. Peptide motifs or sequences according to formula (IV) $CX^1XX^3CXXXCX^7XXXC$ wherein $X^1$ is L, $X^3$ is T or Y, $X^7$ is R or W, and X and C have the same meaning as in 1.
18. the peptide motifs or sequences according to 17, wherein $X^1$ is L and $X^3$ is T.
19. Peptide motifs or sequences selected from the group consisting of CVFTSDYAFC (SEQ ID NO 1), CVIYDGNHWC (SEQ ID NO 2), CIFEPDYSYC (SEQ ID NO 3), CVFDDLYSFC (SEQ ID NO 4), CTFSVDYKYLMC (SEQ ID NO 5), CVFAHNYDYLVC (SEQ ID NO 6), CRFDKEYRTLVC (SEQ ID NO 7), CVSYCLFEFCYVC (SEQ ID NO 8), CVEYCWEGSCYVC (SEQ ID NO 9), CVAYCEEWECYVC (SEQ ID NO 10), CVAYCIEHHCWTC (SEQ ID NO 11), CVSYCDGLQCWMC (SEQ ID NO 12), CLSTCAQSCRISC (SEQ ID NO 13), CLLYCHDACWWVC (SEQ ID NO 14), CVTYCYGEVCYYC (SEQ ID NO 15), CAAYCVAGLCYGC (SEQ ID NO 16), CVQYCIGGDCWFC (SEQ ID NO 17), 5 CVVYCDSMKCWTC (SEQ ID NO 18), CVAYCISSLCYYC (SEQ ID NO 19), CVWYTGNTWC (SEQ ID NO 20), CVFDALYTFC (SEQ ID NO 21) CVIYPGNVWC (SEQ ID NO 22), 10 CIFDGFYILC (SEQ ID NO 23), CVPYLOLWLC (SEQ ID NO 24), and CMFDPMYMWMTC (SEQ ID NO 25).
20. A peptidomimetic compound having a cyclic molecular structure made rigid by a beta-turn, comprising 10 to 12 structural units in the ring, and further comprising in positions 3 and 7 aromatic or amicyclic rigid side group substituents, the side group in position 7 having a substituent providing for hydrogen bonding, whereby the peptidomimetic compound is capable of selectively binding to free PSA and having a binding activity similar to that of a peptide motifs or sequence according to 4 or 10.
21. A peptidomimetic compound having a cyclic molecular structure comprising at least 13 structural units in the ring, stabilized by intramolecular bridges between the units in positions 1 and 13 and 5 and 10, further having in positions 4 and 11 aromatic or alicyclic rigid side group substituents, the substituent in position 4 having further an acid functionality or similar providing for hydrogen bonding capability, whereby the peptidomimetic compound is capable of selectively binding to free PSA and having a binding activity similar to that of a peptide motifs or sequence according to 13.
22. The peptidomimetic compound according to 20 or 21, comprising an oligomer/polymer selected from the group of poly(ester imide)s, polyesters, N-alkylamino cyclic urea, thiourea, bicyclic guanidines, imidazol-pyridino-indoles, hydantoins and thiohydantoins.
23. The peptidomimetic compound according to 22, comprising groups selected from phenyl, cyclopentyl, cyclopenanyl, cyclohexenyl, cyclohexanyl, napthyl, indnyl, furyl, theinyl, pyrrolyl, pyrrolinyl, pyrrolidinyl, pyrazolyl, pyrazolinyl, pyrazolidiniyl, pyridyl, imidazoyl, imidazolinyl, imidazolidinyl, morpholinyl, piperidinyl, pyrazinyl, piperazinyl, pyrimidinyl, pyridazinyl, oxazolyl, oxazolidinyl, isoxazolyl, isoxazolidinyl, isothiazolidinyl, thiazolyl, thiazolidinyl, isothiazolyl, and bicyclic rings.

24. A PSA binding peptide and regulator of enzyme activity comprising a peptide motif 10 and/or sequence according to any of 1 to 19.

25. A PSA binding peptide and regulator of enzyme activity comprising at least one peptidomimetic compound according to any of 20 to 23.

The diagnostic compositions according to the present invention are mainly characterized by what is stated in the characterizing parts of the following:

26. A diagnostic composition comprising at least one peptide motif and/or sequence according to any if 1 to 19 and a diagnostically accepted carrier and/or labeling substance.

27. A diagnostic composition comprising at least one peptidomimetic compound according to any of 20 to 23 and a diagnostically accepted carder and/or labeling substance.

The pharmaceutical compositions according to the present invention are mainly characterized by what is stated in the characterizing parts of the following:

28. A pharmaceutical composition comprising at least one peptide motif and/or sequence according to any of 1 to 19 and a pharmaceutically acceptable carrier and/or labeling substance.

29. A pharmaceutical composition comprising at least one peptidomimetic compound according to any of 20 to 23 and a pharmaceutically acceptable carder and/or labeling substance.

The process for the preparation of the peptide ligands according to the present invention is mainly characterized by what is stated in the characterizing part of the following:

30. A process for producing peptide motifs and sequences according to any of 1 to 19, characterized in that the process comprises a solid-phase Merrifield-type peptide synthesis.

The therapeutic methods according to the present invention is mainly chaacterized by what is stated in the characterizing parts of the following:

31. A method for the therapeutic treatment of conditions dependent on PSA producing cells in mammals, comprising administering to a mammal a peptide motif or sequence according to any of 1 to 19 in an effective mount for binding to PSA and/or regulating its enzyme activity in said mammal.

32. A method for the therapeutic treatment of conditions dependent on PSA producing cells in mammals, comprising administering to a mammal a peptidomimetic compound according to any of 20 to 23 in an effective amount for binding to PSA and/or regulating its enzyme activity in said mammal.

The uses of the present peptide motifs and sequences and peptidomimetics are mainly characterized by what is stated in the characterizing parts of the following:

33. The use of a peptide motif or sequence according to any of 1 to 19 or a peptidomimetic compound according to any of 20 to 23 as a medicine.

34. The use of a peptide motif or sequence according to any of 1 to 19 or a peptidomimetic compound according to any of 20 to 23 for the preparation of a medicament for the treatment of conditions based on regulations of PSA enzyme activity.

35. The use of a peptide motif or sequence according to any or 1 to 19 or a peptidomimetic compound according to any of 20 to 23 as a diagnostic agent.

36. The use of a peptide motif or sequence according to any of 1 to 19 or a peptidomimetic compound according to any of 20 to 23 for the preparation of a reagaent to be used for a PSA-based diagnosis of benign or malignant prostatic diseases and diseases derived from other tissues producing PSA.

37. The use of a peptide motif or sequence according to any of 1 to 19 or a peptidomimetic compound according to any of 20 to 23 in biochemical isolation and purification procedures of various molecular forms of PSA.

Considerable advantages are obtained with the aid of the present invention. The present invention provides for the first time PSA binding ligands which are capable of modulating and even specifically enhancing the enzyme activity of PSA. The peptides according to the present invention can bind specifically with various forms of PSA as part of immunopeptide assays or chromatographical matrices. Furthermore, the peptides display binding specificities which have not been obtained with antibodies. The present peptides and corresponding peptidomimetic compounds can be formulated into pharmaceutical compositions for treatment of PSA secreting cell dependent conditions.

The peptides developed by Denmeade et al. have been conjugated to a cytotoxic drug to form a prodrug, which is activated when cleaved by PSA (13). In an analogous way, the present peptides showing stable binding with PSA can be potentially used to selectively deliver cytotoxic drugs, gene therapy vectors and imaging agents to prostate cancer tissue, without the need for any activation step.

Next, the invention will be described in more detail with the aid of a detailed description and by making reference to the attached drawings.

DETAILED DESCRIPTION OF THE INVENTION

Definitions

Figure 1:
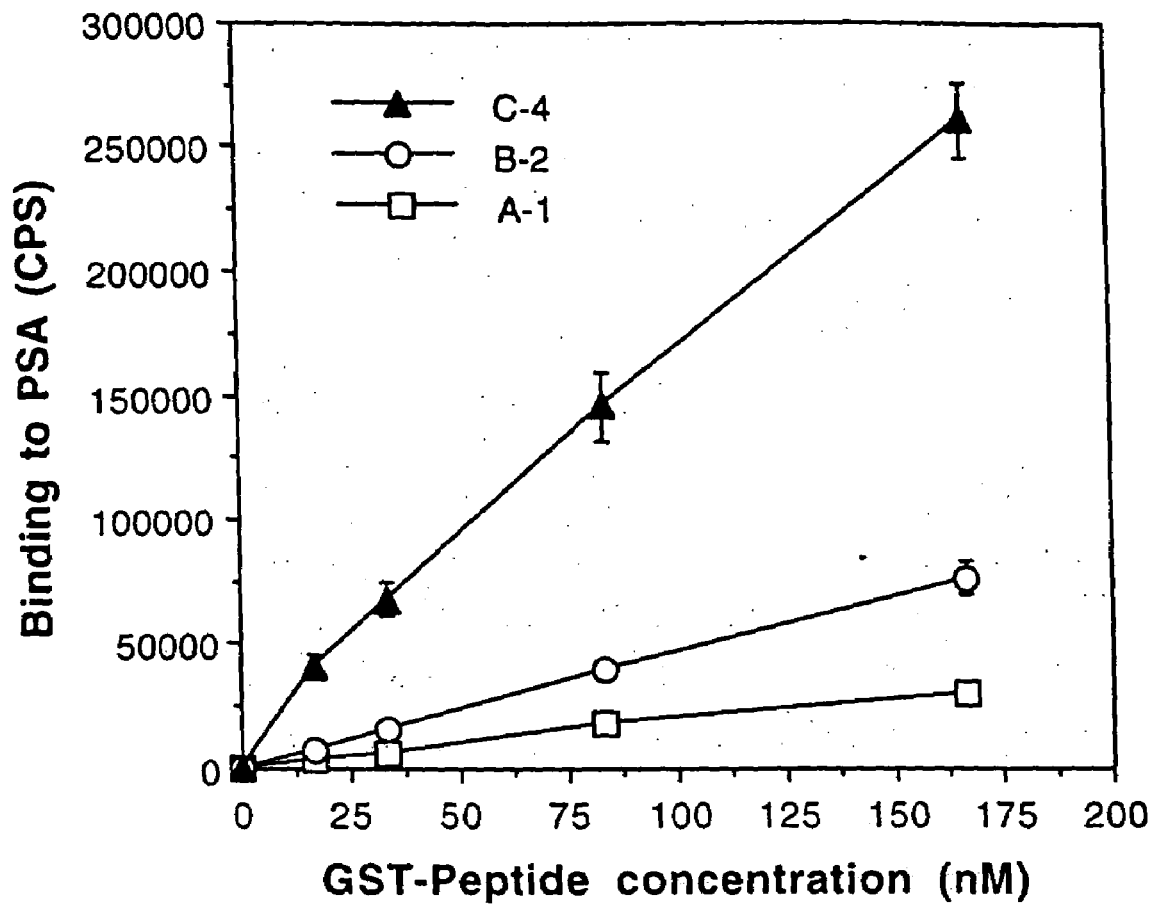
FIG. 1 shows the binding of GST-peptides to immobilized PSA.

For the purpose of the present invention, the term "ligand" stands for a chemical compound or a part of a chemical compound which is capable of binding to the binding domain present on a large polypeptide molecule, such as a hormone, or on the surface of a cell. The present peptide ligands bind to PSA, and modulate or even, in many cases, increase its enzyme activity against synthetic and natural IGF-BP-3 substrate. In the present context, "ligand" is used synonymously with "binding agent".

Generally, the ligand is a chemical compound, e.g. a peptide, which is soluble in physiological solutions or miscible with water and serum. The binding of the present ligands to PSA can be characterized as being "stable" (in contrast to, e.g., an enzymatic reaction) in the respect that the ligand is attached to a binding domain of PSA to the extent that its binding can be measured and determined e.g. by surface plasmon resonance or immuno-peptide assays (IFMA-assay). Further, the bonded ligand cannot be washed or rinsed away with physiologically buffered water. The bonding strength of the present ligands is comparable to that of peptide agents used for the targeting of breast cancer (14).

The binding of the present ligands to PSA is "selective" which is indicated by the fact that MAbs, which are specific for free PSA and serine proteinase inhibitors in complex with PSA prevent the binding of the ligands to PSA. It would appear that the present ligands bind to a site of PSA located in the vicinity of the active site, but this is only a theory which we do not wish to be bound by. Typically, the present peptides and the corresponding peptidomimetic compounds bind to "free" PSA or PSA in complex with α2-macroglobulin. Free PSA is the form of PSA synthesized and secreted by the prostatic epithelial cells.

"Peptide" stands for a strand of several amino acids bonded together by amide bonds to form a peptide backbone. Generally the peptides comprise molecules with molecular weight lower than 10 kDa, i.e. containing about 90 amino acids or less. Peptides can be designated as "small peptides" when they consist of about 6-30 amino acid units. As mentioned above, the present peptides generally comprise at least one cross-link formed by disulfide bonding between cysteine units. If the peptides contain several pairs of cysteines, there can be a multiple number of such cross-links. In addition to disulfide bonds, there can be other cross-links within the peptides as well. The specific structures of some exemplary peptides are discussed in more detail below.

"Peptidyl analogues" are chemical derivatives of the peptides based on the modification of the peptides by various chemical reactions, such as cycloadditions, condensation reactions and nucleophilic additions.

"Peptidomimetic compounds" are compounds, which resemble the original peptides mentioned above. They are generally built up of different chemical building blocks than the amino acids, which form the original peptides. For example, non-peptidyl compounds like benzolactam or piperazine based analogues based on the primary sequence of the original peptides can be used (15, 16). The resemblance between the peptidomimetic compounds and the original peptides is based on structural and functional similarities. Thus, the peptidomimetic compounds mimic the bioactive conformation of the original peptides and, for the purpose of the present application, their binding activity with respect to the binding site of PSA is similar to that of the peptide they resemble. The peptidomimetic compounds can be made up of amino acids (such as D-amino acids), which do not appear in the original peptides, or they can be made from other compounds forming amide bonds or even ester bonds Examples of synthetic peptidomimetic compounds comprise poly(ester imide)s, polyesters, N-alkylamino cyclic urea, thiourea, bicyclic guanidines, imidazol-pyridino-indoles, hydantoins and thiohydantoins (15, 16). They may contain, e.g., the following groups: phenyl, cyclopentyl, cyclopentanyl, cyclohexenyl, cyclohexanyl, naphthyl, indanyl, furyl, thienyl, pyrrolyl, pyrrolinyl, pyrrolidinyl, pyrazolyl, pyrazolinyl, pyrazolidinyl, pyridyl, imidazoyl, imidazolinyl, imidazolidinyl, morpholinyl, piperidinyl, pyrazinyl, piperazinyl, pyrimidinyl, pyridazinyl, oxazolyl, oxazolidinyl, isoxazolyl, isoxazolidinyl, isothiazolidinyl, thiazolyl, thiazolidinyl, isothiazolyl, and bicyclic rings.

The peptidomimetic compounds can be characterized as being "structurally and functionally equivalent" to the peptides.

Generally, the novel binding agent for prostate specific antigen (PSA) comprises either a. a peptide having at least 6 amino acids bonded together to form a peptide backbone and including at least one pair of cysteines which are spaced apart by a number of at least two amino acids and interconnected by a disulfide bond to form a cyclic structure defined by the cysteines, the intermediary amino acids and the disulfide bond; or b. a peptidomimetic compound having a spatial conformation similar to the peptide (mimicking the bioactive conformation of the original peptide).

Both of said compounds exhibit selective binding to free prostate specific antigen and to PSA-A2M (as defined above).

According to a first preferred embodiment of the present invention, the novel PSA binding peptide ligands are based on cyclic structures (disulfide bond between cysteines) of the peptide motifs according to formula (I)

$$CX^1X^2XXXX^6XXC \qquad (I)$$

wherein
$X^1$ is V or I,
$X^2$ is F, I, W or P,
$X^6$ is Y, N or L,
C is cysteine, and
each X stands independently for an amino acid residue.

In particular, in formula (I) $X^1$ is V or I, $X^2$ is F or I and $X^6$ is Y or N. When $X^1$ is V and $X^2$ is F, then $X^6$ is preferably Y and each X is an amino acid residue independently selected from the group consisting of T, S, D, Y A, F, E, P, and L. When $X^1$ is V and $X^2$ is I, $X^6$ is preferably N and each X is an amino acid residue independently selected from the group consisting of Y, D, G, H, W, P, and V. Further, when $X^1$ is I, $X^2$ is preferably F, $X^6$ Y or N, and each X is an amino acid residue independently selected from the group consisting of E, P, D, S, Y, G, F, I and L.

According to another particularly preferred embodiment of peptides according to formula (I), $X^1$ is V or I, $X^2$ is F, I, W or P, $X^5$ is D or N, $X^6$ is Y, N or L, $X^7$ is A or N, $X^8$ is F or Y, the remaining structural units bearing the same meanings as above.

Examples of peptides are represented by the sequences according to SEQ ID NOs: A-1 (SEQ ID NO 1), A-2 (SEQ ID NO 2), A-4 (SEQ ID NO 4), Z-6 (SEQ ID NO 20), Z-7 (SEQ ID NO 21), Z-8 (SEQ ID NO 22), and Z-10 (SEQ ID NO 24) in Table 1 and SEQ ID NOs: A-3 (SEQ ID NO 3) and Z-9 in Table 1(SEQ ID NO 23).

Single-stranded DNA was purified from phage clones after three rounds of selection with PSA. Peptide sequences were deduced from the DNA sequences of the corresponding region of the phage genome. Consensus residues found in several clones are indicated by bold font. Peptides expressed as glutathione S-transferase (GST) fusion proteins are indicated with an asterisk.

According to a second preferred embodiment of the present invention the novel PSA binding peptide ligands can further be based on a cyclic structure of the peptide motifs according to formula (II)

$$CX^1X^2XXXX^6XX^8X^9X^{10}C \qquad (II)$$

wherein
$X^1$ is V, T or R,
$X^2$ is F,
$X^6$ is Y,
$X^8$ is Y or T
$X^9$ is L
$X^{10}$ is V or M, and
X and C have the same meaning as above.

Preferably, in formula (II), $X^1$ is V, $X^2$ is F, $X^6$ is y, $X^8$ is Y, $X^9$ is L, $X^{10}$ is V and X is selected from the group consisting of A, H, N and D. Preferred sequences are exemplified by SEQ ID NOs: B-1 (SEQ ID NO 5), B-2 (SEQ ID NO 6) and B-3 (SEQ ID NO 7) in Table 1.

The structural units in formula (II) may also carry the following meanings: $X^1$ is V, T, or R, $X^2$ is F, $X^6$ is Y, $X^7$ is D or N, $X^8$ is Y, T or A, $X^9$ is L, $X^{10}$ is V or M, and the other units bearing the same meanings as above.

According to a third preferred embodiment of the present invention, the novel PSA binding peptide ligands are based on a cyclic structure of the peptide motifs according to formula (III)

$$CX^1X^2X^3CXXXXCX^8X^9C \qquad (III)$$

TABLE 1

Amino acid sequences of PSA-binding peptides.

| SEQ ID | Code | Library | Peptide Sequence | No of isolates |
|---|---|---|---|---|
| 1 | A-1* | $CX_8C$ | C V F T S D Y A F C | 2 |
| 2 | A-2 | $CX_8C$ | C V I Y D G N H W C | 2 |
| 3 | A-3 | $CX_8C$ | C I F E P D Y S Y C | 2 |
| 4 | A-4 | $CX_8C$ | C V F D D L Y S F C | 1 |
| 5 | B-1 | $CX_{10}C$ | C T F S V D Y K Y L M C | 15 |
| 6 | B-2* | $CX_{10}C$ | C V F A H N Y D Y L V C | 2 |
| 7 | B-3 | $CX_{10}C$ | C R F D K E Y R T L V C | 1 |
| 8 | C-1 | $CX_3CX_4CX_2C$ | C V S Y C L F E F C Y V C | 2 |
| 9 | C-2 | $CX_3CX_4CX_2C$ | C V E Y C W E G S C Y V C | 7 |
| 10 | C-3 | $CX_3CX_4CX_2C$ | C V A Y C E E W E C Y V C | 1 |
| 11 | C-4* | $CX_3CX_4CX_2C$ | C V A Y C I E H H C W T C | 3 |
| 12 | C-5 | $CX_3CX_4CX_2C$ | C V S Y C D G L Q C W M C | 1 |
| 13 | D-1 | $CX_3CX_3CX_3C$ | C L S T C A Q S C R I S C | 7 |
| 14 | D-2 | $CX_3CX_3CX_3C$ | C L L Y C H D A C W W V C | 2 |
| 15 | Z-1 | $CX_3CX_4CX_2C$ | C V T Y C Y G E V C Y Y C | |
| 16 | Z-2 | | C A A Y C V A G L C Y G C | |
| 17 | Z-3 | | C V Q Y C I G G D C W F C | |
| 18 | Z-4 | | C V V Y C D S M K C W T C | |
| 19 | Z-5 | | C V A Y C I S S L C Y Y C | |
| 20 | Z-6 | CX8C | C V W Y T G N T W C | |
| 21 | Z-7 | | C V F D A L Y T F C | |
| 22 | Z-8 | | C V I Y P G N V W C | |
| 23 | Z-9 | | C I F D C F Y I L C | |
| 24 | Z-10 | | C V P Y L G L W L C | |
| 25 | Z-11 | CX10C | C M F D P M Y M W M T C | | wherein
- $X^1$ is V or A,
- $X^2$ is A, S, E, T, V or Q,
- $X^3$ is Y,
- $X^8$ is Y or W,
- $X^9$ is V, T, M, Y, G or F and
- X and C have the same meaning as above.

Particularly, the peptide motifs or sequences according to formula (II) comprise the following amino acid residues: $X^1$ is V, $X^2$ is A or S, $X^3$ is y, $X^8$ is Y or W, $X^9$ is V, Y or T, and each X is independently selected from the group consisting of L, F, E, W, G, S, I, H, D, G, L, Q, Y, V, A, M and K. As will be discussed below in more detail, strong binding to PSA is achieved by clones containing the CVAYC (SEQ ID NO 11) motif. Thus, in formula III, $X^1$ is preferably V, $X^2$ is A and $X^3$ is Y.

$X^3$ can also have the meaning Y or F and $X^5$ the meaning E or Q, the remaining structural units having the same meanings as above, in particular as in the preceding paragraph.

Peptides having formula (III) are shown under the following sequence numbers in Table I: SEQ ID C-1 (SEQ ID NO 8)-C-5 (SEQ ID NO 12), Z-1 (SEQ ID NO 15)-Z-6 (SEQ ID NO 20) and Z-8 (SEQ ID NO 22).

According to a fourth preferred embodiment of the present invention, the novel PSA binding peptide ligands based on a cyclic structure of the peptide motifs according to formula (IV)

$$CX^1XX^3CXXXCX^7XXXC \quad (IV)$$

wherein
- $X^1$ is L,
- $X^3$ is T or Y,
- $X^7$ is R or W, and
- X and C have the same meaning as above.

Preferably, $X^1$ is L and $X^3$ is T. Corresponding sequences in Table 1 have been assigned the numbers SEQ ID NOs: D-1 (SEQ ID NO 13) and D-2 (SEQ ID NO 14).

The present investigation also relates to the use of the motifs described above as lead sequences for development of binding agents with alternative characteristics.

It is another object of the present invention to provide novel PSA binding peptide ligands based on the sequences listed in Table 1. The peptides with SEQ ID A-1 (SEQ ID NO 1)-A-4 (SEQ ID NO 4), B-1 (SEQ ID NO 5)-B-3 (SEQ ID NO 7), C-1 (SEQ ID NO 8)—C-5 (SEQ ID NO 12) and D-1 (SEQ ID NO 13)-D-2 (SEQ ID NO 14) were isolated as described in methods section below. The peptides Z-1 (SEQ ID NO 15)-Z-11 (SEQ ID NO 25) were isolated as the peptides of A-, B-, C- and D-series but 200 μM of $ZnCl_2$ was included in the buffer used for panning.

Peptides A1 (CVFTSNYAFC, SEQ ID NO 1), B2 (CVFAHNYDYLVC, SEQ ID NO 6) and C4 (CVAYCIEHHCWTC, SEQ ID NO 11) exhibit particularly strong binding and their properties and structures have been studied in more detail. The results of these studies are given in Examples 4 and 5.

The structural analyses discussed in Example 5 show that the two peptides A-1 and B-2 (corresponding to general formulas I and II, respectively) have a very similar structure and similar or even the same biological activity. The preferred side chains in A-1 peptide are Phenylalanine (Phe, F) in position 3 and Tyrosine (Tyr, Y) in position 7. In the peptide B-2 the preferred amino acids are the same, viz. Phenylalanine (Phe, F) in position 3 and Tyrosine (Tyr, Y) in position 7.

In sequences A-1 and B-2, the rigid β-turn stabilises the position of aromatic side chains of Phenylalanine (Phe, F) in position 3 and Tyrosine (Tyr, Y) in position 7. The structure is stabilised in the peptide A-1 by hydrogen bond between the carbonyl oxygen of Threonine (Thr, T) in position 4 and the hydrogen of amide of Tyrosine (Tyr, Y) in position 7. The structure is stabilised in the peptide B-2 by the hydrogen bond between the carbonyl oxygen of Alanine (Ala, A) in position 4 and the hydrogen of the amide of Tyrosine (Tyr, Y) in position 7.

The preferred amino acids of the peptide C-4 are Tyrosine (Tyr, Y) in position 4 and Tryptophan (Trp, W) in position 11. The structure is stabilized by the two disulphide bridges; the first between positions Cys1 and Cys13 and second between the positions Cys5 and Cys10.

It should, however, be pointed out that, in addition to the above-mentioned preferred amino acids in the indicated positions, also those alternative amino acids having similar structure and mentioned in the substituent listings relating to the of formulas will give rise to the desired activity. The positions mentioned are calculated from the whole length of the peptides and the cysteins have also been numbered, which means that, for example, the F in position 3 of peptide A-1 corresponds to $X^2$ in formula I.

Based on the data obtained, the peptidomimetic compounds according to the invention having an activity similar to that of the present peptides of formulas I or II will exhibit a basic structure comprising 10 to 12 structural units and in particular having in positions 3 and 7 aromatic or alicyclic rigid groups, the structure being made rigid by a β-turn. The side group attached to the structural unit in position 7 should further have a group providing for hydrogen bonding. The peptidomimetic compounds according to the invention having an activity similar to that of the present peptides of formula III will exhibit a basic structure of 13 structural units, which is stabilized by intramolecular bridges between the units in positions 1 and 13 and 5 and 10, respectively. Further, in positions 4 and 11, the peptidomimetic will exhibit aromatic or alicyclic rigid substituents (side groups), the substituent in position 4 having further an acid functionality or similar providing for hydrogen bonding capability.

The peptidomimetic compounds, as well as the actual peptides, can have a longer molecular chain than the ones disclosed above, as long as the motifs (or the corresponding functional patterns) are present.

The present invention also relates to diagnostic compositions comprising an amount of the novel PSA binding peptides. The diagnostic composition comprising the present peptides and a diagnostically acceptable carrier may be used as such or as peptide-conjugate immobilized to a solid phase matrix of the assay or as labelled peptide-tracer reagent. The diagnostic composition according to the present invention finds use in assays based on determination of various molecular forms of PSA. The diagnostic compositions contain the active component in liquid phase, preferably aqueous phase, in a concentration of about 0.1 to 500 μg/l. The compositions may contain detergents, such as Tween or polysorbates, and stabilizing agents. The concentrations of the other components can be about 0 to 50% of the weight of the composition.

As the results of Example 4 show, the present peptides can be used for purification of PSA and for differentiation between various forms of free PSA. Because these peptides possess novel binding specificities towards PSA, i.e. they bind specifically with the intact form of free PSA, they are potentially useful in development of assays with improved accuracy for prostate cancer.

The present invention also relates to a pharmaceutical composition comprising an amount of the novel PSA binding peptide ligands. The pharmaceutical composition comprising the novel PSA binding peptides according to the invention may be used systemically, locally and/or topically, and may be administered e.g. parenterally, intravenously, subcutaneously, intramuscularly, intranasally, by pulmonary aerosol or in depot form. The compositions may also include all potential combinations of the peptides with labelling reagents, imaging reagents, drugs and other chemicals/-molecules.

The present invention also relates to the use of the peptides to mediate gene delivery to PSA expressing cells or to cells in the vicinity of PSA expressing cells. A general description of the use of peptides for gene delivery mediation may be found in reference 17.

Pharmaceutical compositions suitable for intravenous infusion or injection are particularly preferred and they comprise the active component in a concentration of, generally, about 0.1 to 500 g/l, preferably about 1 to 250 g/l. It is preferred to have somewhat higher concentrations (e.g. about 20 to 200 g/l), to allow for administration without causing excessive volume load to the patients. The preparation may be lyophilized and reconstituted before administration or it may be stored as a solution ready for administration. The pH of the solution product is in the range of about 5 to about 8, preferably close to physiological pH. The osmolality of the solution can be adjusted to a preferred value of at least 200 mosmol/l using sodium chloride and/or sugars, polyols or amino acids or similar components. The compositions can further contain pharmaceutically acceptable excipients and stabilizers, such as albumin, sugars and various polyols. The amounts of these components can vary broadly within a range of about 0 to 50 wt-% of the active component. Liquid formulations provide the additional advantage of being ready for administration without reconstitution.

For oral administration it may be necessary to prepare derivatives of the present peptides. According to a particularly interesting embodiment, the peptides (and peptidomimetics) are incorporated into a liposome package containing diagnostic/therapeutic compounds, such as cytotoxic drugs doxorubicin and methotrexate. Liposome packaging peptides are disclosed in references 18, 19. Coupling of the peptides to the surface of the liposome enables the targeting of it to PSA producing cells.

The present invention also includes the use of the novel PSA binding peptides for the manufacture of reagents for PSA based diagnosis of benign and malignant prostatic disease and diseases derived from other tissues producing PSA.

The present invention also includes the use of novel PSA binding peptides for the manufacture of the above-mentioned pharmaceutical preparations for the treatment and targeting of conditions based on the use of present invention. The present invention also includes the use of novel PSA binding peptides for treatment of conditions based on regulation of PSA enzyme activity. Thus, generally the novel peptides and structurally and functionally equivalent peptidomimetics (=active components) can be employed in pharmaceutical compositions to treat mammalian cancers as well as other conditions, by administering an effective dose of the peptide or peptidomimetic or a therapeutically acceptable acid or salt or derivative thereof in a pharmaceutical carrier. They can be administered with a pharmaceutically acceptable carrier at dosages of from about 1 to about 1,000 micrograms per kg of body weight daily. As mentioned above the composition may be administered parenterally, intravenously, subcutaneously, intramuscularly, intranasally, by pulmonary aerosol or in depot form.

The present invention also relates to the use of the novel PSA binding peptides for biochemical isolation and purification procedures of various forms of PSA.

The present invention also relates to a process for the preparation of these PSA binding peptides by standard solid phase Merrifield peptide synthesis. The peptides according to the present invention can be used as such or as labelled derivatives as part of quantitative assays for various molecular forms of PSA, or as compounds to regulate the activity of PSA or for targeting of PSA producing cells. Furthermore, these peptides can be used as lead compounds to design peptidomimetics for purposes described above. The peptides can also be used in column chromatographic matrices for biochemical isolation and purification of various forms of PSA, as already discussed above and further studied in Example 4. Yet further, the motifs according to the present invention can be used as lead sequences for development of binding agents with alternative characteristics.

The present peptides can also be used in methods for modulating the PSA enzyme activity and PSA activity-dependent conditions by using these peptides either in vivo or in vitro. Further, the peptides according to the present invention can be used in procedures for biochemical isolation and purification of PSA.

The peptides according to the present invention also increase the activity of PSA against IGF-BP-3, and, thus, they also affect the activity of PSA against natural substrates. Thus, the present peptides are potentially useful for modulation of the biological function of PSA in prostate pathology and physiology. Interestingly, none of the peptides identified inhibited enzyme activity.

PSA has been shown to inhibit endothelial cell proliferation and invasion [8, 1999 #626], and to split plasminogen into fragments corresponding to angiostatin, which inhibits endothelial cell growth and vessel formation (9). The present peptides bind to PSA, and increase its enzyme activity against synthetic and natural substrate. Thus, the peptides could also increase the ability of PSA to produce angiostatin and to inhibit the growth of blood vessels associated with cancer progression.

Because of its highly prostate specific expression, PSA is a potential target for prostate cancer therapy. Denmeade et al. have developed peptide substrates (12), which are specifically cleaved by PSA. These peptides have been conjugated to a cytotoxic drug to form a prodrug, which is activated when cleaved by PSA (13). In an analogous way, the peptides according to the present invention can be used to selectively deliver cytotoxic drugs, gene therapy vectors and imaging agents to prostate cancer tissue. The small size of these peptides enables them to penetrate efficiently into prostatic tissue. Peptides homing selectively to endothelium of specific target organs have been previously developed by phage display (20). Likewise, the prostate specificity of our PSA-binding peptides peptides enables them to be localized specifically to PSA-producing cells.

The following non-limiting examples illustrate the invention further.

EXAMPLE 1

Identification of PSA Binding Phage

A convenient way to develop novel binding agents for various targets is to screen libraries of random peptides. Phage display is a powerful method for selection of novel ligands for various target proteins (21) including enzymes, antibodies and receptors. Phage display libraries offer a way to identify specific ligands possessing binding specificities different from those displayed by antibodies.

Phage Display Libraries

The construction of phage display peptide libraries in fuSE 5-phage has been described (21). Libraries with the structures $CX_8C$, $CX_{10}C$, $CX_3CX_3CX_3C$ and $CX_3CX_4CX_2C$, where C is cysteine and X is any of the 20 naturally occurring amino acids, were used.

Antibodies and Proteins

The development of MAb 5E4 will be described in a separate report (Leinonen, manuscript in preparation). MAb H117 was obtained from Abbott Diagnostics (North Chicago, Ill., USA) and 5A10 was from EG&G-Wallac, Turku, Finland. Anti phage monoclonal antibody was a kind gift from Dr. Petri Saviranta, University of Turku, Turku, Finland. A polyclonal anti GST antibody was from Amersham Pharmacia Biotech. PSA was purified from human seminal fluid as described previously (3). HK2 was a kind gift from Dr. Janita Lövgren, University of Turku, Turku, Finland. The proteinases chymotrypsin and cathepsin G were from Athens Research and Technology, Athens, Ga., USA, trypsin was purified as described (22), and kallikrein was from Calbiochem, Calif., USA. The antibodies against chymotrypsin and cathepsin G were from Fitzgerald, Mass., USA, an antibody against human plasma kallikrein from Calbiochem, Calif., USA, and an antibody against trypsin was prepared as described (23). Anti-ACT and anti-API antibodies were from Dako, Glostrup, Denmark.

Selection of Phage Peptides

The screening of phage display peptide libraries was performed essentially as described by Koivunen et al. (21). Briefly, each phage library was separately screened with PSA captured on microtiter wells coated with the monoclonal antibody 5E4, which binds both free and complexed PSA (24). 33 nM PSA in TBS buffer containing 10 g/L BSA (BSA-TBS) was incubated in wells coated with MAb 5E4 for 1 h, then the wells were washed to remove unbound PSA. An aliquot of each phage library (1011-1012 infectious particles) was added to the wells, and incubated for 3 h at 22° C. during the first round of panning and for 1 h during subsequent rounds. The phage solution was removed and the wells were washed with TBS containing 0.5% Tween 20. The panning was also performed in the presence of 200 μM ZnCl2. The bound phage were eluted with 0.1 M glycine buffer, pH 2.2 and neutralized with 1 M Tris base. The eluted phage were amplified by infection of E. coli K91 kan cells, and purified by precipitation with polyethylene glycol. After three rounds of selection and amplification single stranded DNA from individual phage clones was prepared and the peptide sequences were determined by sequencing the relevant part of the viral DNA. Sequencing was performed with an ABI 310 Genetic analyzer and Dye Terminator Cycle Sequencing Core Kit (PE Applied Biosystems, Foster City, Calif., USA) using the oligonucleotide 5'CCCTCATAGTTAAGCGTAACG (SEQ ID NO:26) 3' as a primer.

To isolate PSA-binding peptides, we screened four phage libraries expressing cyclic disulfide-constrained peptides containing 10, 12 or 13 amino acids at the N-terminus of phage protein III. The peptides isolated from each library contained characteristic consensus amino acids in addition to the cysteine engineered in fixed positions, (Table 1). Most peptides derived from the $CX_8C$, $CX_{10}C$ and $CX_3CX_4CX_2C$ libraries (9 out of 12) contained valine in the $X^1$ position. In addition, phenylalanine frequently occurred at the $X^2$ position of the $CX_8C$, and $CX_{10}C$ libraries. The $X^3$ position was favored by tyrosine and $X^9$ position was favored by V in the $CX_3CX_4CX_2C$ library peptides. In the phage IFMA (data not shown) and GST-peptide IFMA, the clones containing the CVAYC (SEQ ID NO 29) motif showed the strongest binding to PSA (cf. FIG. 1, Table 1).

FIG. 1 shows the results of experiments in which various amounts of each GST-peptide were added to wells containing PSA captured by MAb 5E4. After washing the binding of GST-peptide was quantified by IFMA using an Eu-labelled anti GST antibody as tracer. Data represent mean values from duplicate wells ±standard error (SE).

A tyrosine residue was also enriched in either the position $X^6$ or $X^8$ of the $CX_8C$ and $CX^{10}C$ peptides and in position $X^8$ of the $CX^3CX^4CX^2C$ peptides. After including $Zn^{2+}$ in the panning buffer, several PSA binding peptides could be isolated (Table 1, peptides with SEQ ID Z-1 (SEQ ID NO 15)-Z-11 (SEQ ID NO 25)). Most of these peptides contained similar motifs as the peptides isolated without $Zn^{2+}$.

EXAMPLE 2

Characterization of the Peptides

Construction of GST Fusion Protein Containing Selected Peptides

Single-stranded phage DNA was purified and the insert region was amplified by PCR with primers upstream (5'AGGCTCGAGGATCCTCGG CCGACGGGGCT 3') (SEQ ID NO 27) and downstream (5'AGGTCTAGAATTCGCCCCAGC GGCCCC 3') (SEQ ID NO 28) of the fuse 5 gene III sequence (20). The amplified DNA was isolated and subcloned between the BamH I and EcoR I sites of the PGEX-2TK vector (Amersham Pharmacia Biotech, Helsinki, Finland) for expressing the selected peptides as GST fusion protein. Recombinants were verified by DNA sequencing. The fusion proteins were expressed in E. coli BL 21 cells and purified by glutathione affinity chromatography (Amersham Pharmacia Biotech) as described (25). The purity of the fusion protein was analyzed by SDS-polyacrylamide gel electrophoresis in 12.5% homogeneous gels on the PhastSystem (Amersham Pharmacia Biotech). Their ability of binding to PSA was measured by an immunofluorometric assay (IFMA) (see below).

Peptide was released from the GST fusion partner by thrombin cleavage. 20 units of thrombin (Amersham Pharmacia Biotech) was incubated with 1 mg GST-C-4 in PBS buffer at 22° C. for 12 h. Cleaved and intact GST-C-4 fusion proteins were analyzed by gel filtration on a Superdex 200 HR 10/30 column using 50 mM sodium-phosphate, pH 7.4 containing 150 mM NaCl and a flow rate of 30 ml/h. Absorbance was monitored at 280 nm and the protein-containing fractions of 0.5 ml volume were collected and analyzed by the GST-peptide IFMA as described below.

Immunofluorometric Assays (IFMAs)

The solid phase antibodies used in the IFMAs were coated onto microtitration wells at a concentration of 5 μg/mL in TBS for 16 h at 22° C., the solution was discarded and the wells were saturated with 10 g/L bovine serum albumin in TBS for 3 h at 22° C. The antibodies used as tracers were labeled with a $Eu^{3+}$ chelate as described previously (26). The assay buffer was 50 mM Tris-HCL, pH 7.7, 150 mM NaCl, 33.3 μM bovine serum albumin, 1 μM bovine globulin.

The binding of individual phage clones to PSA was tested by IFMA (phage IFMA). In the phage IFMA, about 30 ng of PSA was added to MAb 5E4 coated wells for 1 h. After washing (Buffer: 150 mM NaCl, 7.7 mM $NaN_3$, 0.2 g/L Tween 20), 15 μL of phage and 200 μl assay buffer was added. After incubation for 1 h, the wells were washed and filled with 200 µl of assay buffer containing 50 ng europium-labeled anti phage monoclonal antibody recognizing the M13 coat protein of the phage. After incubation for 60 min, the wells were washed 4 times, and enhancement solution (EG&G-Wallac) was added. The fluorescence was quantified with a 1234 DELFIA Research fluorometer (EG&G-Wallac). Binding of GST-peptide to PSA was determined by an IFMA (GST-peptide IFMA) similar to the one for phage peptides except that $Eu^{3+}$-labeled antibody to GST was used. Various amounts of GST-peptide or wild type GST were added to wells containing captured PSA in 200 µL of assay buffer and incubated for 1 h. To test the effect of $Zn^{2+}$ on the binding between GST-peptide and PSA, various concentrations of $Zn^{2+}$ (1-200 µM) were added to the buffer in the incubation step of GST-peptide and PSA. In competition experiments, GST-peptide (167 nM) or wild type GST were first incubated with increasing amounts of PSA (0-333 nM) in 0.5% BSA-TBS buffer for 60 min, then added to wells containing PSA captured by MAb 5E4. After incubation for 1 h the wells were washed and $Eu^{3+}$-labeled anti GST antibody was added. After further incubation and washing the bound fluorescence was measured as described above. When assessing the binding of the GST-peptides to other proteinases, including chymotrypsin, cathepsin G, trypsin, and kallikrein, these proteinases were captured by their specific antibodies coated to the microtitration well. Recombinant hK2 was captured by MAb 5E4, which is known to bind hK2 (24). For assessing the binding of the GST-peptides with complexes of PSA, including PSA-ACT and PSA-α1-protease inhibitor (PSA-API) (28), the complexes were captured by antibodies against ACT and API, respectively. After capturing the various proteinases or PSA complexes, GST-peptide was added and binding was monitored as described above for the GST-peptide IFMA.

Surface Plasmon Resonance

The binding kinetics of selected peptides to PSA was studied by surface plasmon resonance (29) on a BIAcore 2000™ instrument (Biacore AB, Uppsala, Sweden). PSA was captured to the solid phase by MAb H117 which binds to the same epitope as MAb 5E4 (30). The capture antibody was covalently coupled onto the surface of the CM5 sensor chip according to the manufacturer's instructions, using coupling levels of 5000 resonance units (RU). PSA was captured by injection of 416 nM of PSA in PBS, 4-min contact time (5 µl/min) and 60 min wash (20 µl/min) providing ligand levels in the range 500-600 RUs. Each analyte (GST-peptide), at various concentrations, was injected for 1 min at 20 µl/min flow rate. To characterize the effect of $Zn^{2+}$ on the affinity of the peptides, the sensorgrams were recorded for a constant amount of peptide in the presence of $Zn^{2+}$ both in the running and sample buffer (0-30 µM). PSA-binding to either chemically activated/deactivated blank surface or MAb H117 alone was subtracted as a non-specific interaction. Regeneration after each measurement cycle was done with 3×0.5 min injections of 10 mM HCl. Binding data were analyzed using the BIAEVALUATION software.

The activity of the peptide cleaved from GST fusion protein was determined by a competition experiment. After fractionation of digested fusion protein by gel filtration, the fractions were incubated in wells containing PSA captured by MAb 5E4 for 60 min. After emptying of the wells, the GST-peptide (167 nM) was added and incubated for 1 h. The effect of the cleaved peptide on the binding between GST-peptide and PSA was monitored by the GST-peptide IFMA.

For characterization of the binding site of the peptides on PSA, monoclonal anti PSA antibodies recognizing various epitopes on PSA were used (30). Each MAb (33 nM) was incubated in wells containing PSA captured by MAb 5E4. After washing, 167 nM GST-peptide was added and binding was monitored by GST-peptide IFMA as described above.

Reactivity of the Peptides with Various Forms of Free PSA

The reactivity of the GST-peptides with propSA and intact PSA was compared by using active PSA (3) and propSA (31). 100 ng of propSA or intact PSA was reacted with MAb 5E4 coated onto microtitration wells. After washing, one µg of each GST-peptide was added to wells containing immobilized PSA. The binding of GST-peptide was quantified by IFMA using Eu-labelled anti-GST antibody as tracer.

Binding of Synthetic Peptides with PSA

Peptides A1 and C4 were synthesized by standard solid phase Merrifield peptide synthesis using fmoc-chemistry. The peptides were assayed for binding with PSA by studying the ability of the synthetic peptide to inhibit the binding of the corresponding GST peptide with PSA. Synthetic peptide (0-333 nM) and the corresponding GST peptide (167 nM) were incubated with PSA captured by MAb 5E4 for 1 h. After this, the wells were washed, after which $Eu^{3+}$-labeled anti GST antibody was added. After further incubation and washing the bound fluorescence was measured as described above.

We constructed GST fusion proteins from four peptides, which display the strongest binding in the phage IFMA. Among them, peptide C-4 with the sequence CVAYCIEHHCWTC (SEQ ID NO 11) showed the strongest binding to PSA both as a GST-peptide (FIG. 1, Table 2) and when expressed on phage (data not shown).

TABLE 2

Kinetics and affinity for the binding of GST-peptides to PSA

| Peptide no. | Maximal binding (CPS)* | ka × $10^3$ (1/Ms) | kd × $10^{-3}$ (1/s) | $K_D$ (µM) | 50% stimulation (µM)# |
|---|---|---|---|---|---|
| A-1 | 219000 | 10.3 | 80 | 7.8 | 2.2 |
| B-2 | 428000 | 16.3 | 57 | 3.5 | 1.7 |
| C-4 | 790000 | 9.9 | 28 | 2.9 | 0.57 |

The association rate constat (ka), dissociation rate constant (kd) and equilibrium dissociation constant ($K_D$) for GST-peptides to PSA were measured by surface plasmon resonance. The values shown are the average ka, kd and $K_D$ at 3 different concentrations of analyte (GST-peptides).

*Data from GST-peptide IFMA. The experimental procedure is described on the legend to FIG. 1.

The peptide concentration required for half maximal stimulation of the enzyme activity of PSA. For experimental procedures see legend to FIG. 6.

Figure 2:
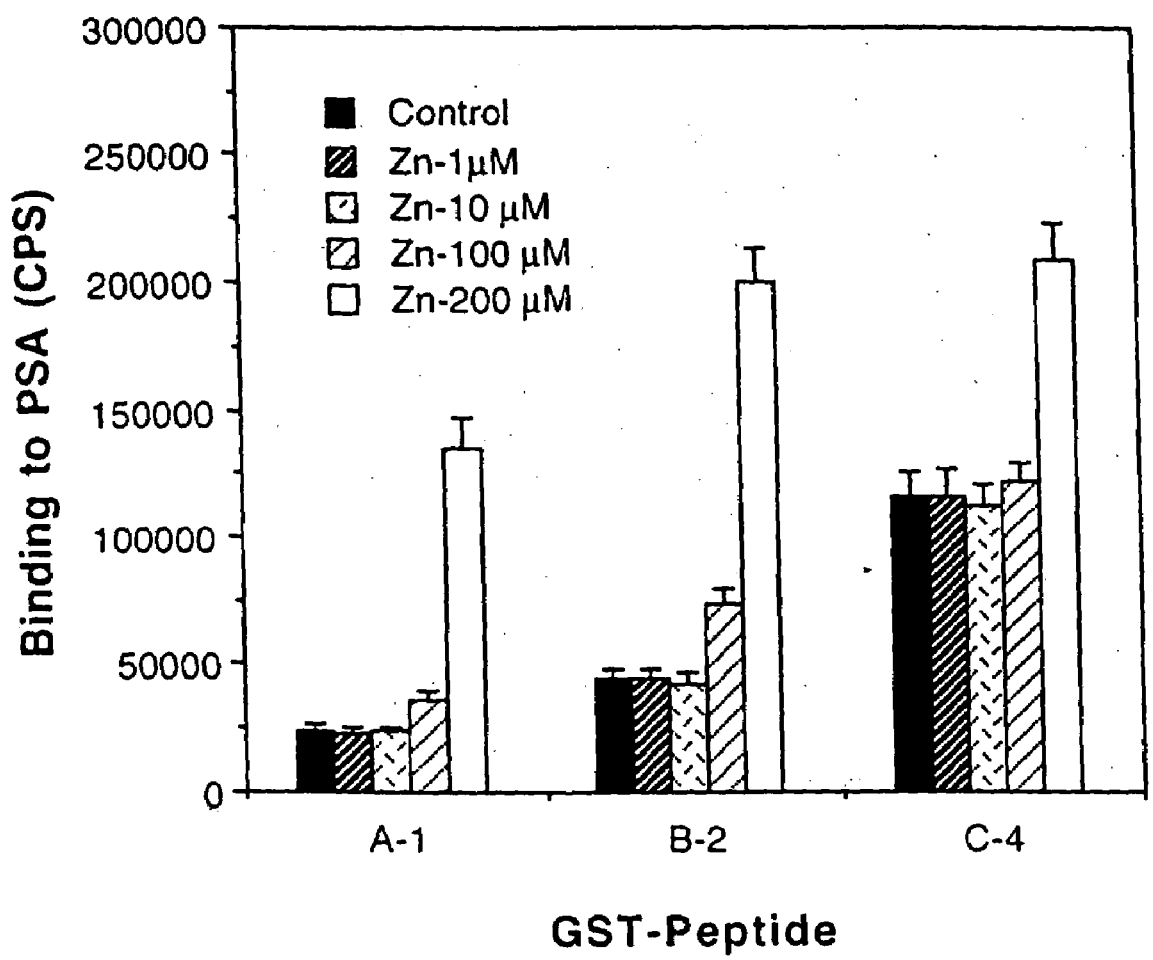
FIG. 2 shows the effect of $Zn^{2+}$ on the binding of GST-peptides to PSA.

Two other selected peptides, B-2 (SEQ ID NO 6) (CVFAH-NYDYLVC) and A-1 (SEQ ID NO 1) (CVFTSDYAFC) bound to PSA but less efficiently than C-4 (SEQ ID NO 11). When $Zn^{2+}$, a cation known to bind to PSA, was included in the assay buffer the binding activity of peptides was increased. $Zn^{2+}$ had a dose dependent effect and the maximal increase in binding response was detected at a 200 µM concentration (FIG. 2). In the experiments, the results of which are illustrated in FIG. 2, each GST-peptide was incubated in PSA-containing wells in the presence of various concentrations of $Zn^{2+}$. The binding of GST-peptide was quantified by IFMA. The control shows the binding of GST-peptide in the absence of $Zn^{2+}$. Data represent mean values from duplicate wells ±SE. However, the effective $Zn^{2+}$ concentration is lower because BSA in the buffer contains several binding sites for $Zn^{2+}$. The fourth peptide produced as a GST fusion protein, D-1 (SEQ ID NO 13) (CLSTCAQSCRISC) did not show significant binding to PSA even though the corresponding phage bound to PSA (data not shown). Wild type GST did not bind to PSA confirming that the binding of the fusion protein was mediated by the inserted peptide.

Figure 3:
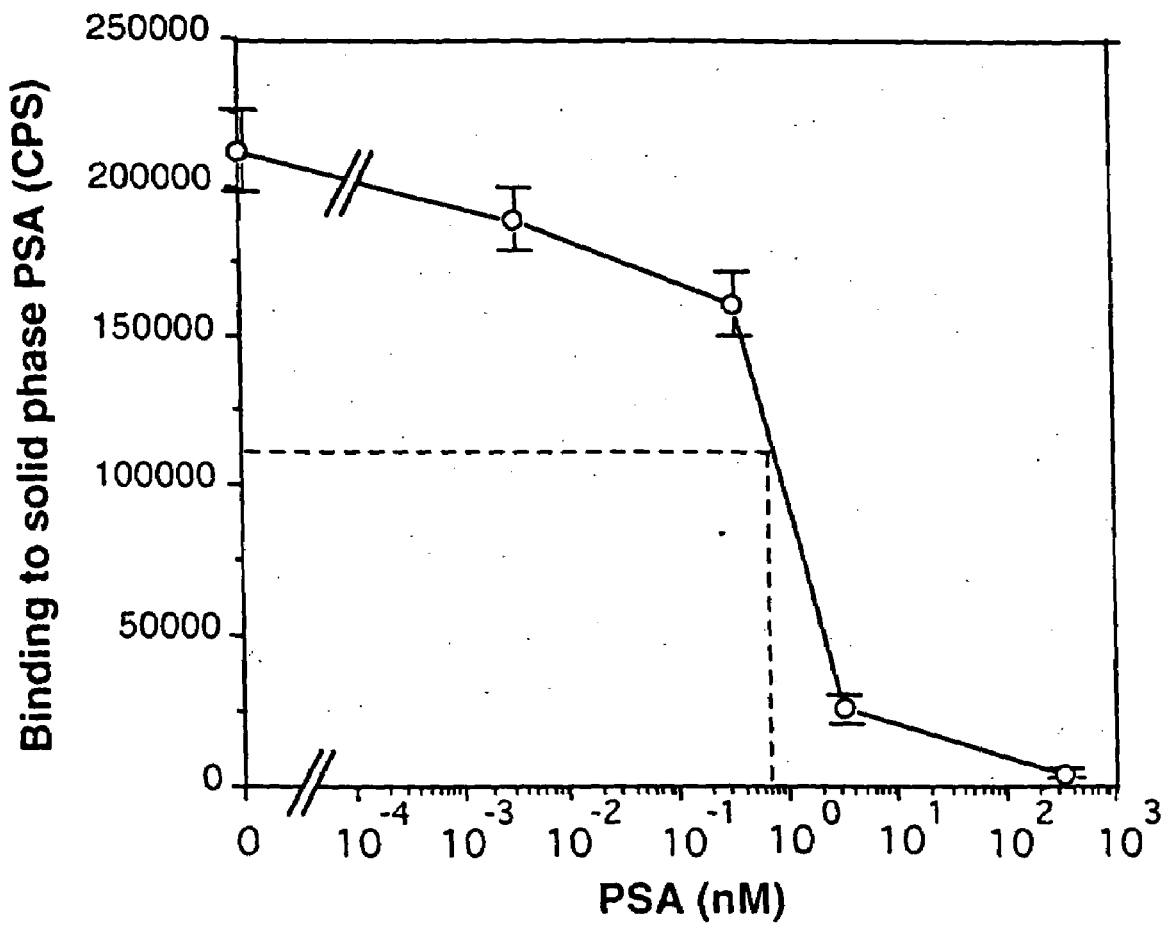
FIG. 3 depicts the effect of PSA in solution on the binding of GST-C-4 with solid phase PSA.

The PSA-binding peptides were further characterized by estimating the PSA concentration required to reduce the binding of the peptide to immobilized PSA by 50% (IC50). In this connection, we refer also to FIG. 3. GST-C-4 was preincubated with increasing concentrations of PSA in solution for 1 h. Then the samples of the mixtures were added to wells in which PSA had been captured by anti PSA MAb. The binding was measured by IFMA. Data represent mean values from duplicate wells ±SE. The corresponding values for the peptides A-1 (SEQ ID NO 1) and B-2 (SEQ ID NO 6) were 3.3 nM and 1 nM, respectively (data not shown). Preincubation of the GST-peptides with an excess of free PSA inhibited binding to the solid phase PSA. The binding of peptide C-4 (SEQ ID NO 11) to captured PSA was reduced by 50% at a PSA concentration of 0.7 nM. These results confirmed that the selected peptides bind not only to PSA captured by MAb 5E4 but also to free PSA in solution.

Figure 4A:
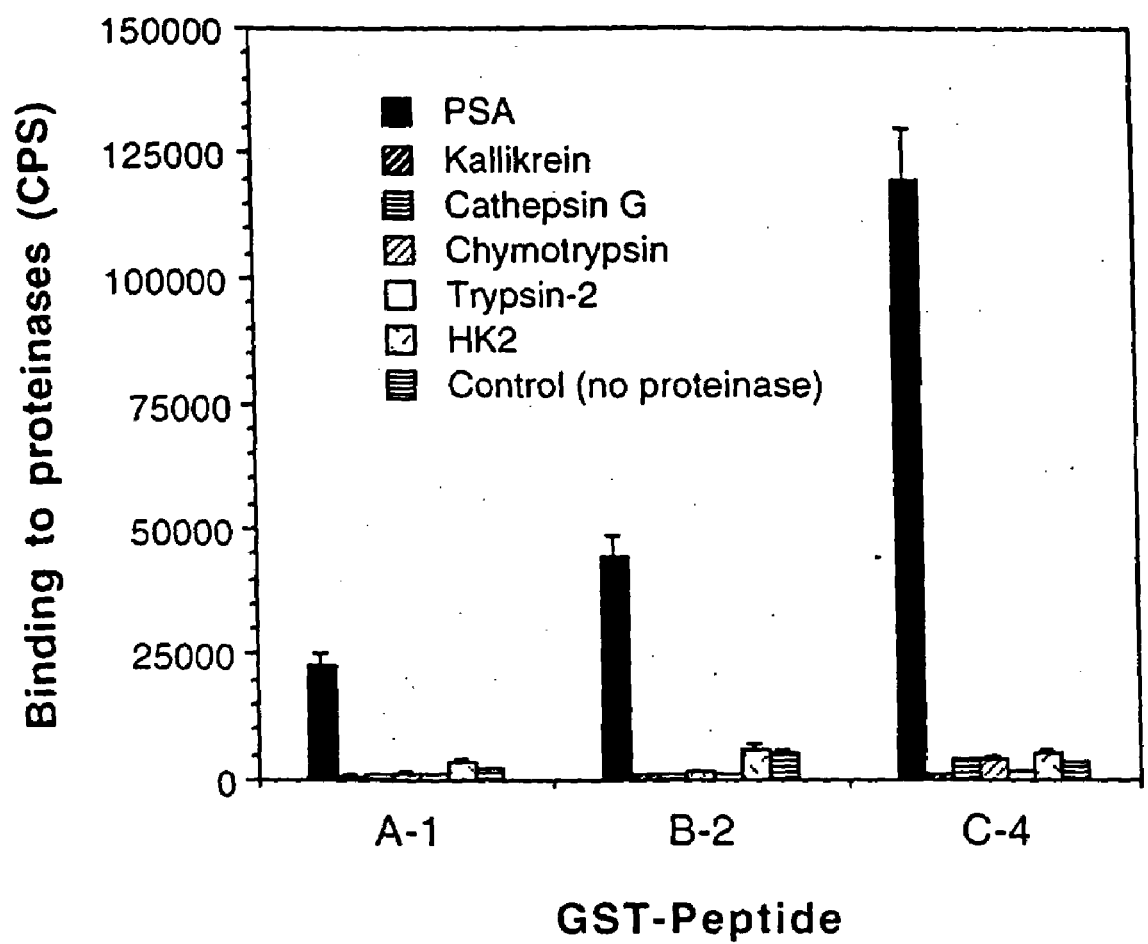
FIGS. 4a and 4b present, respectively, the reactivity of GST-peptides with various proteinases related to PSA and with PSA-serpin complexes.
Figure 4B:
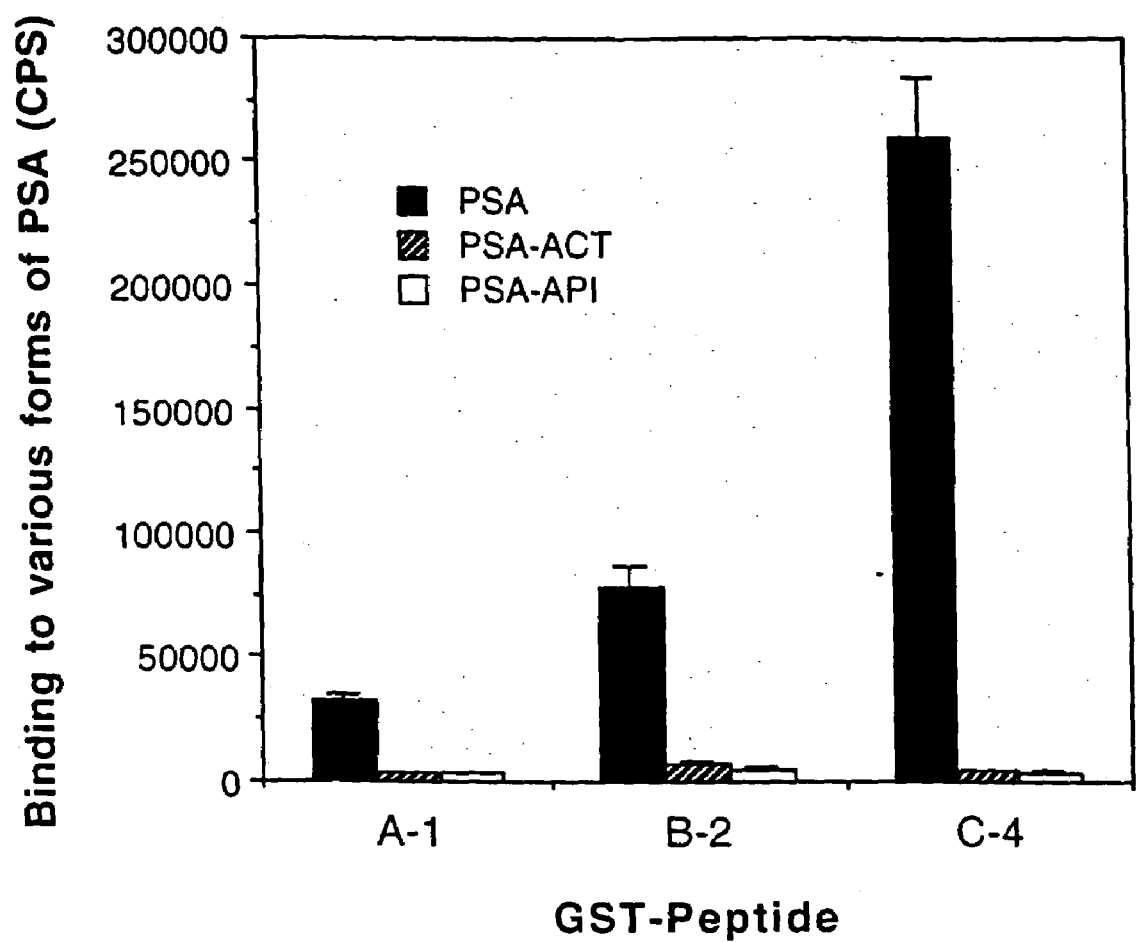

The specificity of the peptides was studied by reacting them with various proteinases and PSA complexes captured by antibodies to microtitration wells. PSA, kallikrein, cathepsin G, chymotrypsin, trypsin-2, and recombinant hK2 were captured onto wells coated with antibodies against each proteinase, respectively. GST-peptide binding was measured by IFMA. The results obtained are presented in FIG. 4a. None of the proteinases tested showed significant binding of the GST-peptides. PSA, PSA-ACT and PSA-API were captured onto wells coated with antibodies against PSA, ACT and API, respectively. GST-peptide binbnding to PSA complexes was measured by IFMA. The results obtained are presented in FIG. 4b. The peptides did not either bind to PSA-ACT and PSA-API captured by antibodies to ACT and API, respectively.

The binding kinetics and affinity of the peptides to PSA was estimated by surface plasmon resonance. Increasing concentrations of GST-peptides were injected over PSA captured by MAb H117. Background-corrected sensorgrams were fitted to single-site interaction between GST-peptide and PSA using three different GST-peptide concentrations and the rate equation:

$$d(GST\text{-peptide:}PSA)/dt = ka(GST\text{-peptide}) \times (PSA) - kd(GST\text{-peptide:}PSA).$$

Figure 5:
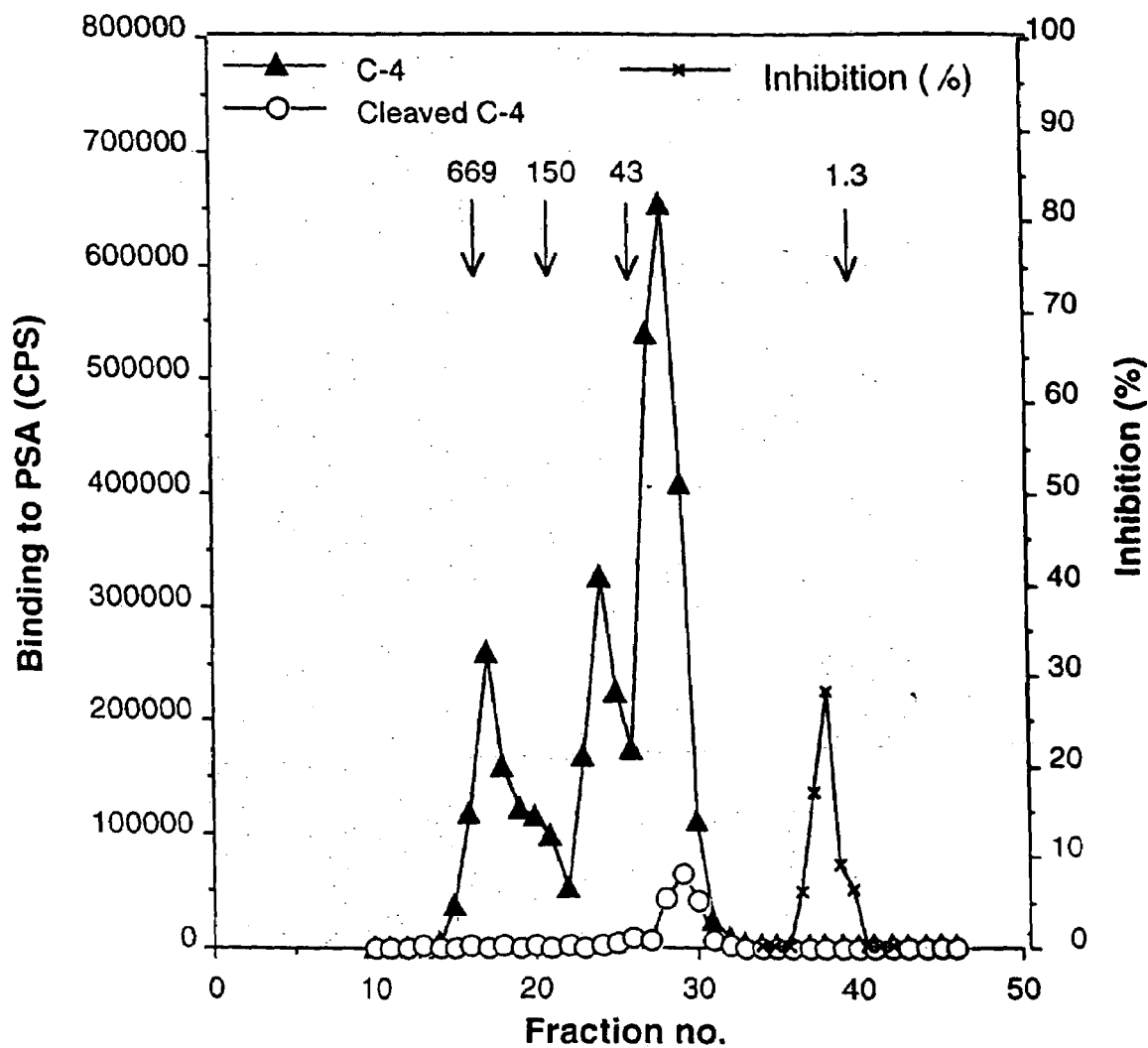
FIG. 5 presents the fractionation of the GST-C-4 by gel filtration.

The average equilibrium dissociation constants (KD) for the peptides A-1, B-2 and C-4 were 2.9-7.8 µM (Table 2). Zn2+ at concentrations of 1-30 µM reduced both association and dissociation rates. The affinity increased 3-7-fold because of a greater decrease in kd than in ka (Table 3). Slow dissociation of PSA from the capturing MAb caused a decreasing baseline and the binding constants were corrected for the baseline drift. In gel filtration, GST-C-4 revealed four peaks (Table 4, FIG. 5).

The association rate constat (ka), dissociation rate constant (kd) and equilibrium dissociation constant ($K_D$) for GST-peptides to PSA were measured by surface plasmon resonance.

† Evaluations are based on average of 3 single fits between analyte concentrations 3.4-8.5 µM. Values are given with the standard deviation.

\* Evaluations are based on single fits at the given $Zn^{2+}$ concentrations using 3.4 µM peptide. Values are given with the obtained standard errors in each fit.

TABLE 4

Comparison of the activities of different molecular size forms of GST-C-4.

| Fusion protein | MW (kD) | Protein (% of total) | Binding activity (% of total) |
|---|---|---|---|
| GST-C-4 | ~3 | 3.4 | |
| | ~30 | 83.4 | 53 |
| | ~100 | 11.4 | 26 |
| | >500 | 1.7 | 21 |
| Thrombin-cleaved GST-C-4 | ~3 | 17 | |
| | ~30 | 83 | 5.2* |

In gel filtration, GST-C-4 and thrombin-cleaved GST-C-4 revealed four and two peaks, respectively. The percentage of protein in each peak was estimated by absorbance at 280 nm. The binding activity ws calculated from the GST-peptide IFMA assay.

*Denotes binding activity remaining after thrombin-treatment.

After fractionation of GST-C-4 or thrombin-treated GST-C-4, 5 µl of each fraction was first incubated in wells containing PSA captured by MAb 5E4. The binding was measured by GST-peptide IFMA. The arrows show the elution of molecular size standards (669 kD, 150 kD, 43 kD and 1.3 kD).

The molecular sizes of the peaks were >500 kD, 100 kD, 30 kD and about 3 kD. All of these forms except the 3 kD peak bound to PSA (Table 4, FIG. 5). This indicates that the fusion protein exists as a 30 kD monomer, an oligomer (about 100 kD) and a polymer. The polymeric fusion protein showed the strongest binding to PSA as indicated by the response in relation to the protein absorbance at 280 nm. Thrombin treatment of GST-C-4 caused its nearly complete cleavage into 30 kD and 3 kD components. The latter consisted of the estimated 31-residue long peptide cleaved from the GST fusion protein by thrombin. The 30 kD component had only about

TABLE 3

Effect of $Zn^{2+}$ on the binding kinetics and affinity for the binding of GST-peptides to PSA

| Concentration of zinc (µM) | A-1 | | | | B-2 | | | | C-4 | | | |
|---|---|---|---|---|---|---|---|---|---|---|---|---|
| | ka × 10³ (1/Ms) | kd × 10⁻³ (1/s) | $K_D$ (µM) | increase (fold) | ka × 10³ (1/Ms) | kd × 10⁻³ (1/s) | $K_D$ (µM) | increase (fold) | ka × 10³ (1/Ms) | kd × 10⁻³ (1/s) | $K_D$ (µM) | increase (fold) |
| 0† | 10.3 [±0.4] | 80 [±2.6] | 7.8 [±0.6] | — | 16.3 [±3.5] | 57 [±0.8] | 3.5 [±0.7] | — | 9.9 [±1.0] | 28 [±1.3] | 2.9 [±0.2] | — |
| 1* | 1.8 [±0.01] | 4.7 [±0.1] | 2.6 [±0.1] | 3 | 1.06 [±0.03] | 3.5 [±0.06] | 3.1 [±0.3] | — | 4.1 [±0.1] | 12 [±0.1] | 2.9 [±0.1] | — |
| 10* | 1.2 [±0.01] | 1.6 [±0.01] | 1.4 [±0.05] | 5.9 | 2.65 [±0.03] | 1.6 [±0.02] | 0.6 [±0.02] | 6 | 3.8 [±0.04] | 2.0 [±0.2] | 0.53 [±0.05] | 5.5 |
| 30* | 1.9 [±0.01] | 2.0 [±0.02] | 1.0 [±0.1] | 7.7 | 0.83 [±0.02] | 0.6 [±0.1] | 0.8 [±0.05] | 4.7 | 4.6 [±0.2] | 4.0 [±0.1] | 0.86 [±0.1] | 3.4 |

5% of the response in the GST-peptide IFMA in comparison to non-cleaved GST-C-4 (Table 4).

In inhibition experiment, the 3 kD peak reduced the binding of GST-peptide to PSA by about 30% (FIG. 5) showing that the thrombin cleaved peptide retained PSA binding activity. The cross symbol (x) shows the inhibition of the binding of GST-peptide induced by peptide cleaved form GST-peptide. 200 μl of each fraction containing free peptide was first incubated in wells containing PSA captured by MAb 5E4. After 1 h, the wells were emptied and GST-C-4 (167 nM) was added. After incubation for 1 h, the binding of GST-peptide was measured by GST-peptide IFMA. Data represent average values from duplicate wells.

To determine the binding site of the peptides on PSA, inhibition experiments were performed with MAbs binding to various epitopes on PSA. Antibodies binding to epitope regions, which in complexed PSA are covered by the serine proteinase inhibitors (so called free-specific antibodies) inhibited the binding of the peptides most strongly (>80%). MAbs binding to epitopes distant from the active site of PSA showed lower degree of inhibition (Table 5).

TABLE 5

Inhibition of GST-peptide binding to PSA by anti PSA MAbs.

| | | GST-Peptide | | |
|---|---|---|---|---|
| ISOBM-MAb | Epitope Group | A-1 | B-2 | C-4 |
| 25 | 1 | ++ | ++ | ++ |
| 26 | 1 | ++ | ++ | ++ |
| 40 | 2-a | + | + | + |
| 90 | 2-b | + | + | + |
| 57 | 3-a | + | + | + |
| 89 | 3-b | + | + | + |
| 86 | 5 | + | + | + |
| Control | 6 | − | − | − |

PSA-MAbs representing four epitope groups on PSA were used to compete with the GST-peptides for binding with PSA. Antibody from group 6, in which MAb 5E4 belongs, was used as a negative control. Each MAb (33.3 nM) was incubated with PSA captured by 5E4 coated onto microtiter wells. After washing, GST-Peptide was added. The binding of GST-peptides was quantified by IFMA.

Reduction of binding of GST-peptide to solid phase PSA (%)+

++=>80%+
+=60-80%
−=No inhibition

The GST peptides showed significantly lower binding to propSA as compared to active PSA. In the experiments 100 ng of propSA or intact PSA was reacted with MAb 5E4 coated onto microtitration wells. After washing, 1 μg of each GST-peptide (SEQ ID A-1 (SEQ ID NO 1), B-2 (SEQ ID NO 6) and C-4 (SEQ ID NO 11), Table 1) was added to wells containing immobilized PSA. The binding of GST-peptide was quantified by IFMA using Eu-labelled anti-GST antibody as tracer.

Figure 6:
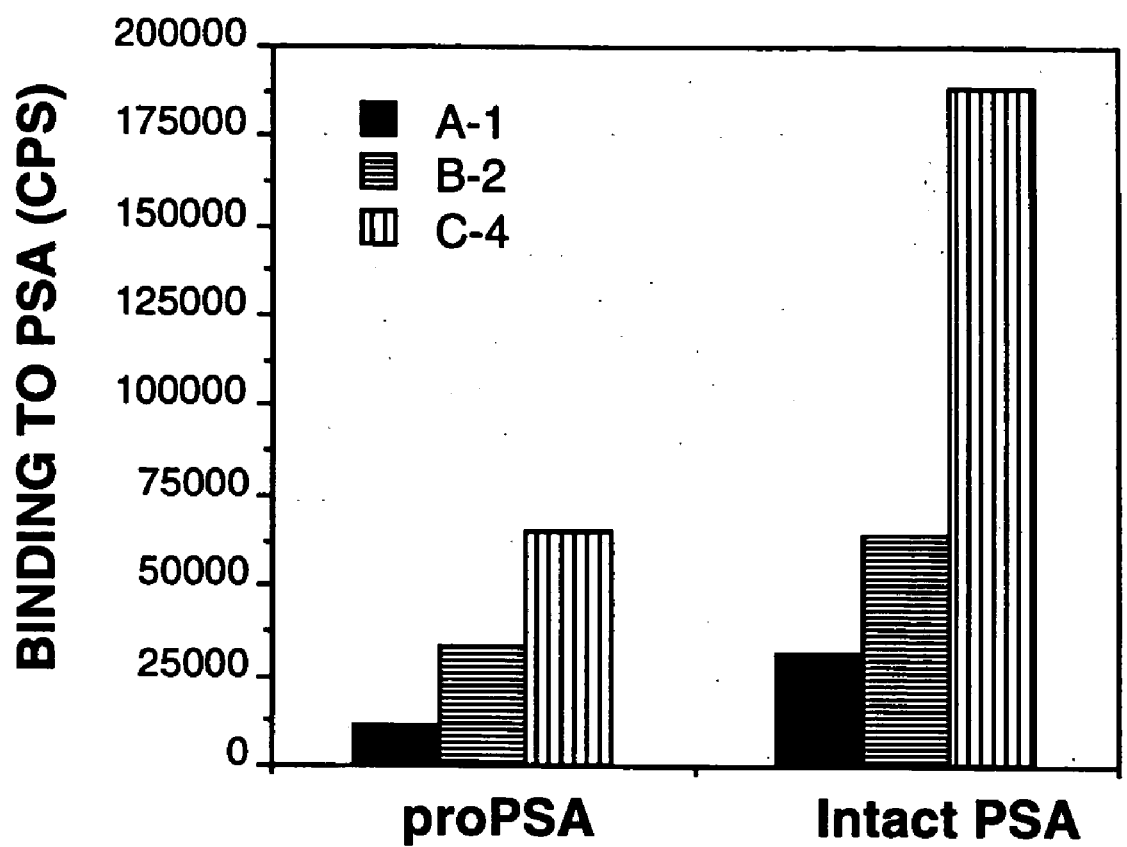
FIG. 6 illustrates the binding of the GST peptides with the proenzyme form of PSA and with active PSA.

The reactivity with propSA was 30-60% of that with active PSA (FIG. 6). After studying 80 MAbs for the ability to preferentially bind with either form of PSA, no MAb preferentially recognizing propSA or intact PSA could be found. Thus, the peptides may provide novel binding specificities for PSA.

Figure 7:
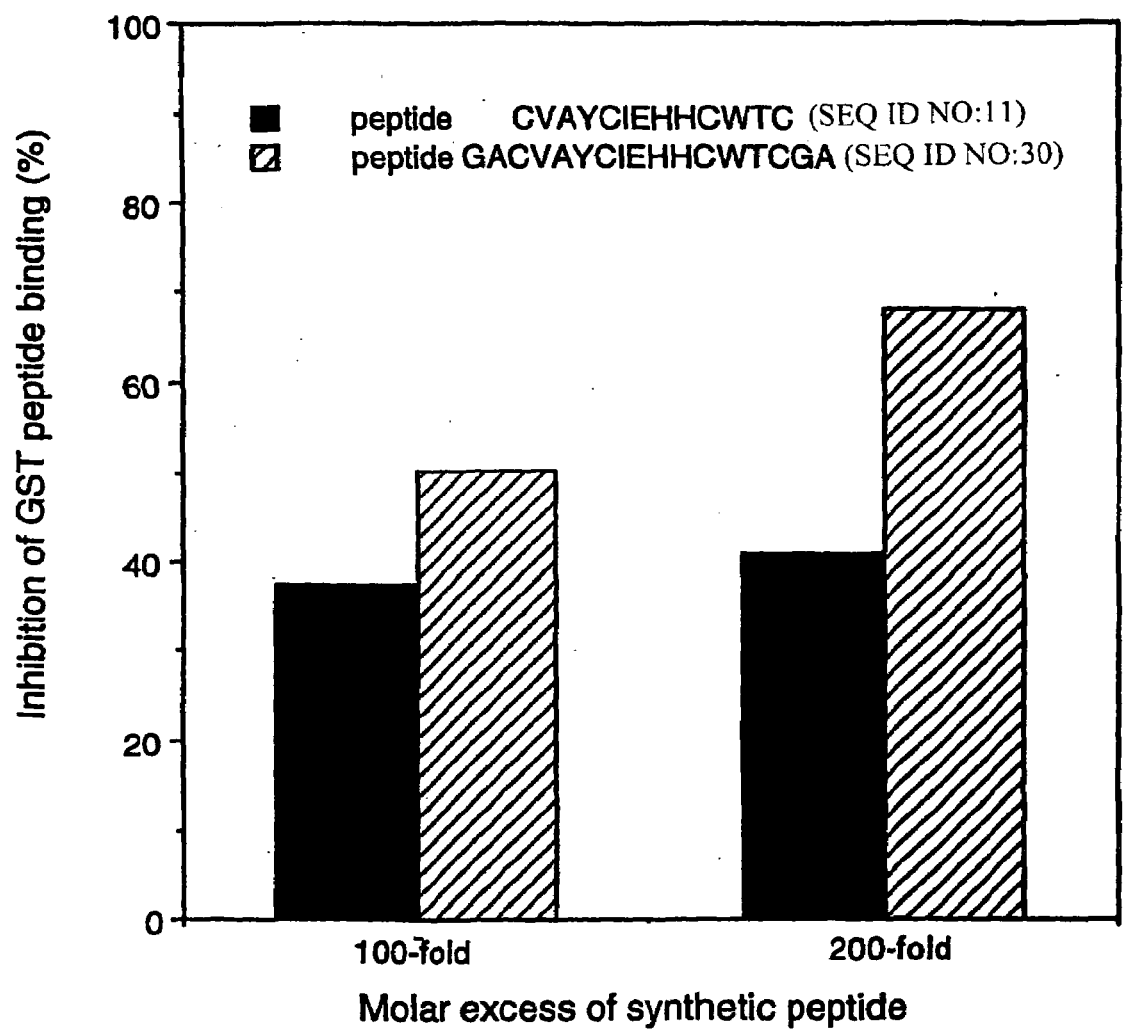
FIG. 7 depicts the effect of chemically synthesized peptides on the binding of GST-C-4 to solid phase PSA.

Peptides synthesized chemically by standard solid phase Merrifield peptide synthesis inhibited efficiently the binding of GST peptides to PSA (FIG. 7) which shows that they bind with PSA in a similar manner as the GST-peptides. The chemically synthesized peptide C-4 (SEQ ID NO 11) (GACVAYCIEHHCWTCGA) in 20-fold molar excess inhibited the binding of the corresponding GST-peptide to PSA by about 70%. Also a shorter derivative of C-4 lacking the flanking GA-motif in the N- and C-termini of the peptide efficiently inhibited the binding of GST-peptide with PSA (FIG. 7). PSA had been captured by anti-PSA MAb in the microtitration wells. The binding was measured by IFMA.

EXAMPLE 3

Effect of Peptides on the Enzyme Activity of PSA

The enzyme activity of PSA was studied in the presence of peptides alone or together with $Zn^{2+}$ by using the chymotrypsin substrate S-2586 (MeO-Suc-Arg-Pro-Tyr-pNA) (Chromogenix, Mölndal, Sweden). Furthermore, the enzyme activity was studied in the presence of peptides synthesized by standard solid phase Merrifield peptide synthesis using fmoc-chemistry including a biotin-conjugated form of the peptide. PSA (333 nM) was incubated with a 1-100-fold molar excess of GST-peptide or 100-fold excess of synthetic peptide in TBS buffer, pH 7.8 containing 0.5 g/L BSA for 1 h at 22° C. The effect of $Zn^{2+}$ on the enzyme activity of PSA was studied by including 1-200 μM of ZnCl2 in the reaction buffer. The combined effect of peptides and Zn2+ on the enzyme activity of PSA was studied by incubating PSA (333 nM) with peptide (333 nM) in the buffer containing 1-200 μM $Zn^{2+}$ for 1 h. After addition of substrate to a final concentration 0.2 mM, the absorbance was monitored at 5-min intervals for 2 h at 405 nm on a Labsystems Multiskan MCC/340 photometer (Labsystems, Helsinki, Finland). As a control, the effect of wild type GST on the enzyme activity of PSA was tested.

The effect of the peptides on the enzyme activity of chymotrypsin, cathepsin G and trypsin was studied as described above for PSA. As substrates, S-2586 was used for chymotrypsin and cathepsin G, and S-2222 (CO-Ile-Glu-(OR)-Gly-Arg-pNA) (Chromogenix) for trypsin.

Effect of the peptides on the enzyme activity towards high molecular weight protein substrates was studied by using PSA to proteolytically cleave insulin like growth factor-binding protein 3 (IGF-BP-3) (32) alone or in the prescence of synthetic peptide C-4 and A1. The extent of the cleavage of the substrate was quantitated by monitoring the decrease in IGF-BP-3 immunoreactivity due to proteolytic cleavage of it. PSA (5 μg/mL) was incubated with IGF-BP-3 (70 ng/mL) for 16 h at 37° C. with 100-fold molar excess of peptides to PSA and measured for IGF-BP3 immunoreactivity by IFMA as described (33). As control, the peptide was also added to the reaction mixture containing PSA and IGF-BP3 just before starting the immunoassay to quantify the possible interference of the peptide in the IFMA for IGF-BP-3.

The effect of chemically synthesized peptide C-4 on the enzyme activity of PSA in complex with alpha-2-macroglobulin (A2M) was analyzed by using purified PSA-A2M complex prepared as described (7). 1 μg of PSA in complex with A2M was incubated alone or with 2.5 μg of peptide C4 (SEQ ID NO 11) (GACVAYCIEHHCWTCGA) synthesized by standard solid phase Merrifield synthesis for 1 h at 22° C. in 100 μL of TBS buffer containing 1 g/L of BSA. 10 μg of monoclonal antibody 4G10 was included to inhibit the activity due to PSA released from the complex. As a control, the enzyme activity of 1 μg of free PSA was measured. The enzyme activity was monitored as above by using S-2586 (Chromogenix) as substrate.

Figure 8:
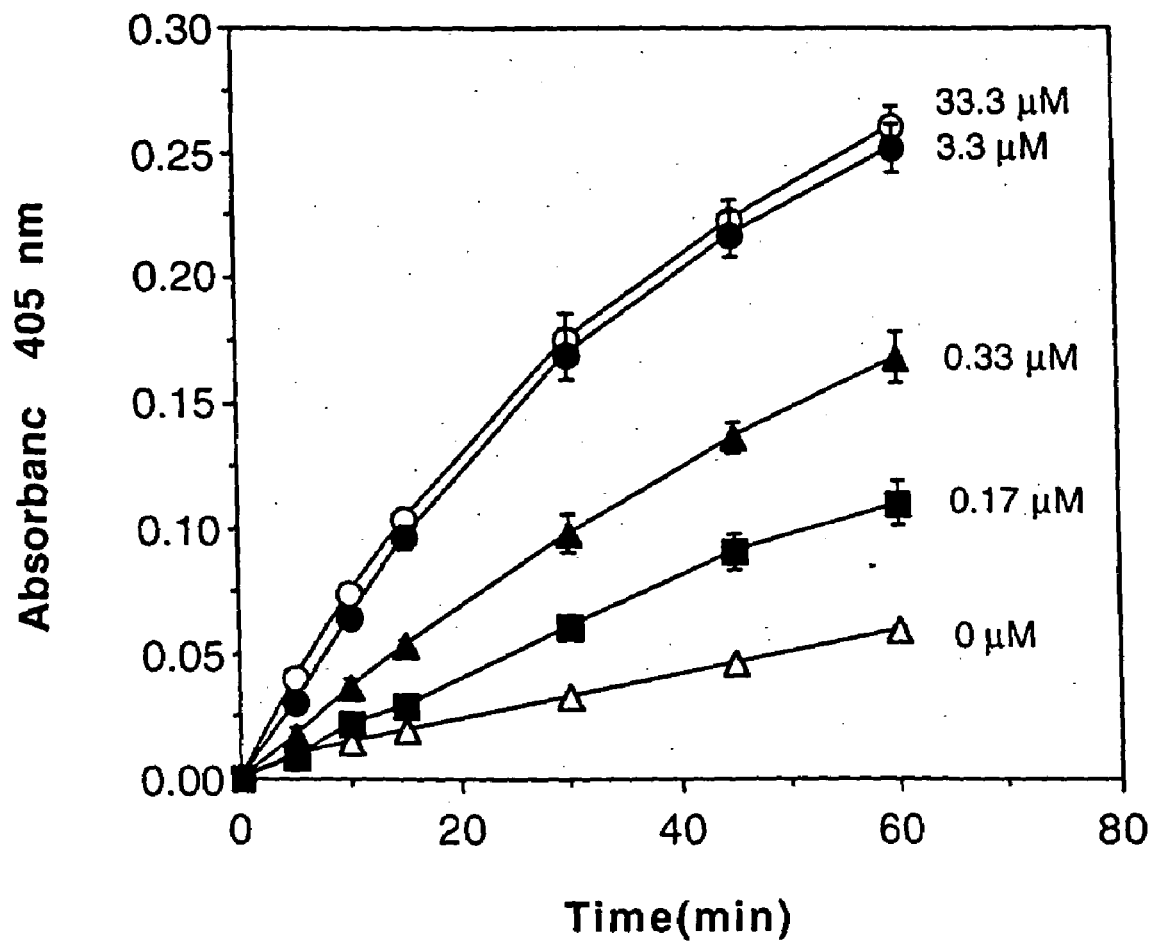
FIG. 8 shows the effect of GST-C-4 on the enzyme activity of PSA.

The enzyme activity of PSA was significantly enhanced by the GST-peptides and GST-C-4 was the most active one, stimulating PSA activity against the chromogenic substrate about 5-fold (FIG. 8). In the experiments, PSA (0.33 µM) was incubated with increasing concentrations of GST-C-4 (0-100-fold molar excess) for 1 h, after which the chromogenic substrate S-2586 was added and enzyme activity was monitored by measuring the absorbance at 405 nm. Data represent mean values from duplicate wells ±SE.

Figure 9:
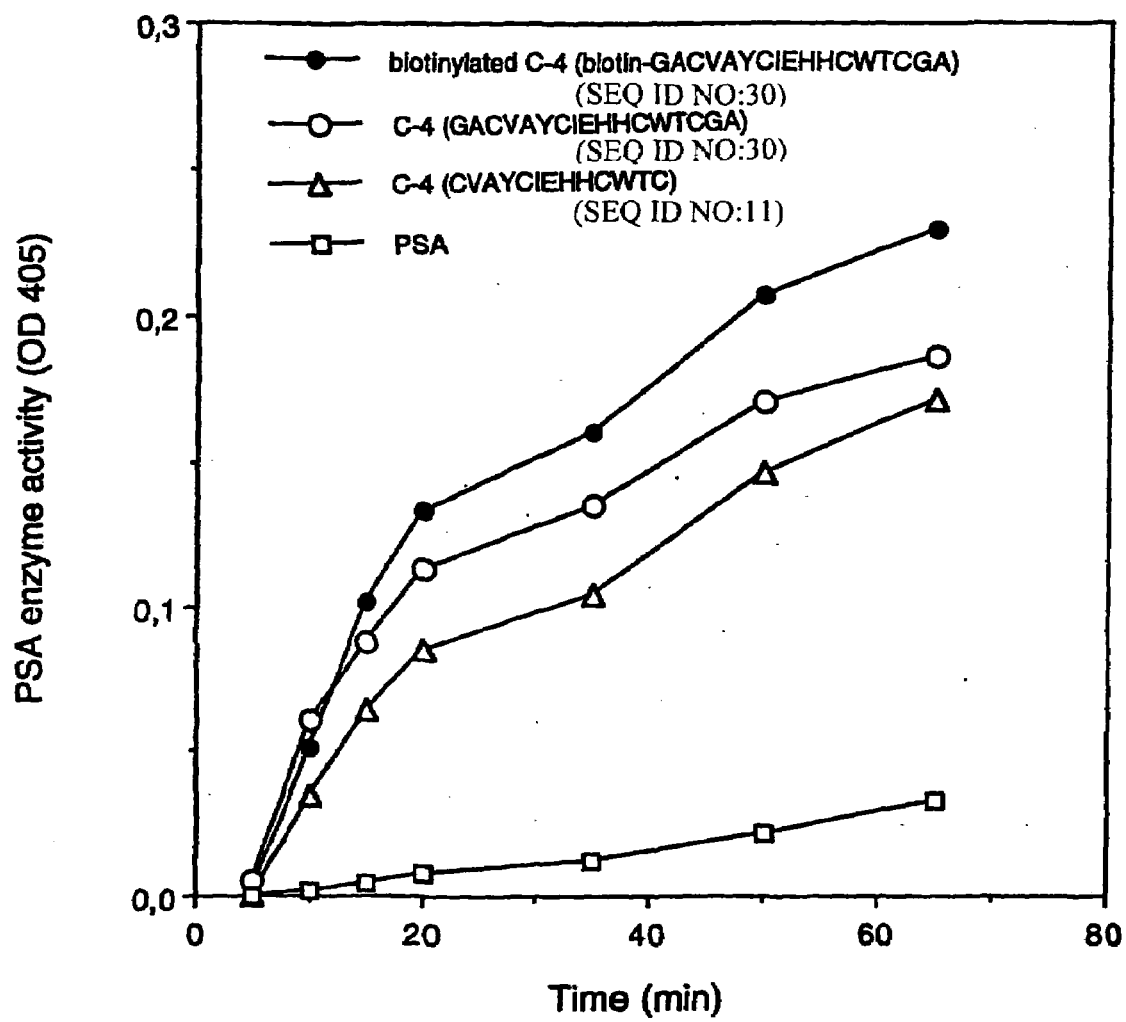
FIG. 9 depicts the effect of chemically synthesized peptide C4 on the enzyme activity of PSA.

The effect was dependent on the GST-peptide concentration and half maximal stimulation was detected with concentrations in the micromolar range (Table 2). The minimum peptide concentration affecting the activity varied between 20 nM for C-4 and 300 nM for A-1 and B-2. Wild type GST did not affect the activity of PSA (data not shown). The peptides did not have any effect on the enzyme activity of the other proteinases tested, including chymotrypsin, cathepsin G and trypsin (data not shown). The peptides prepared by standard peptide synthesis enhanced the enzyme activity in a similar manner (FIG. 9). Furthermore, biotin conjugated peptide C-4 also enhanced the enzyme activity in the same way as the non-conjugated form of C-4 (FIG. 9). In FIG. 9, the derivatives of C-4 tested include peptides with or without the GA-flanking residues in the N- and C-termini and a biotin conjugated form of C-4. PSA (0.33 µM) was incubated with chemically synthesized peptides (100-fold molar excess) for 1 h, after which the chromogenic substrate S-2586 was added and enzyme activity was monitored by measuring the absorbance at 405 nm.

Figure 10:
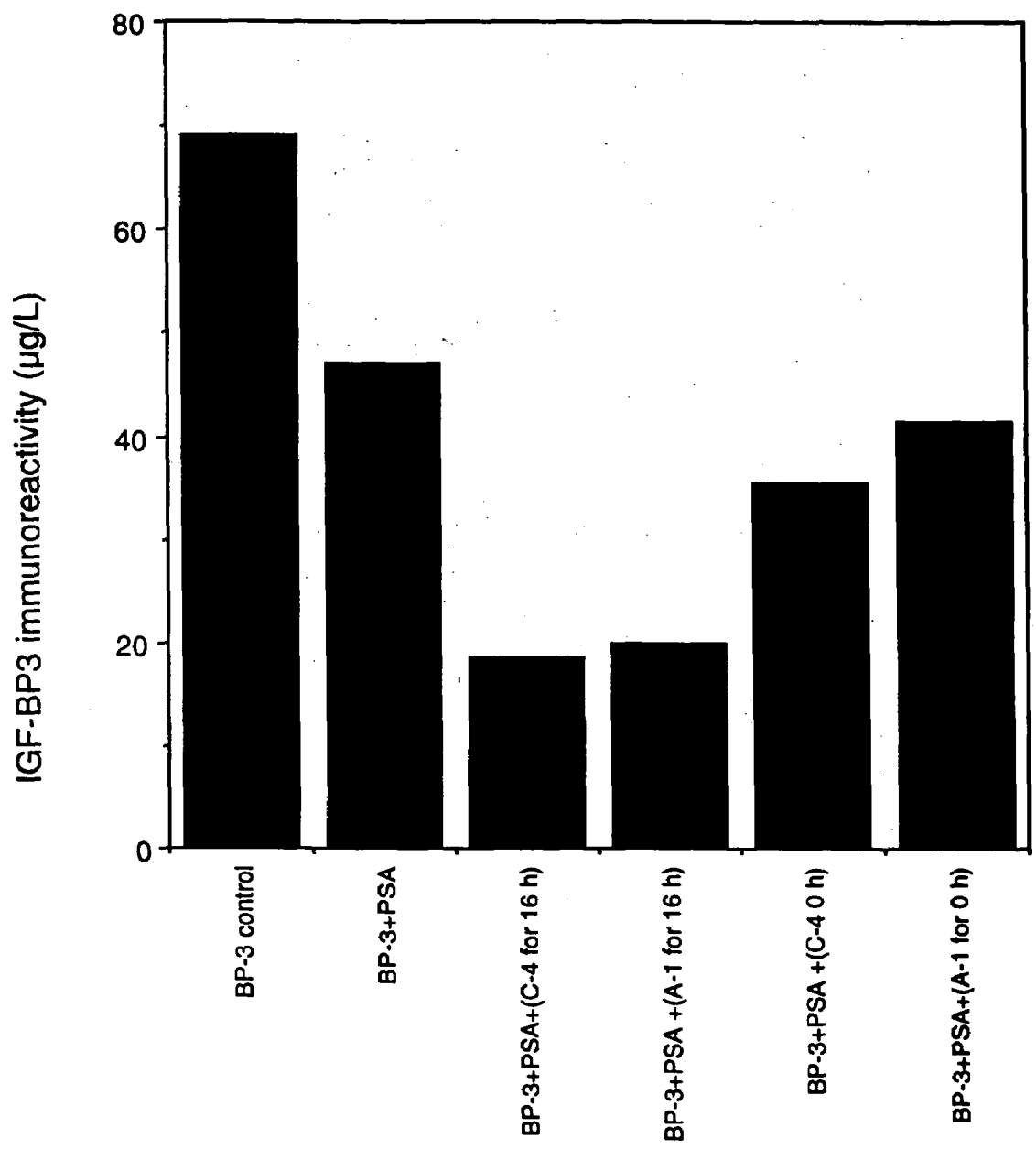
FIG. 10 illustrates the effect of chemically synthesized peptide C-4 and A-1 on the proteolytic activity of PSA towards IGF-BP-3.

The effect of the peptides on the enzyme activity towards high molecular weight protein substrates was assessed by studying the ability of PSA to proteolytically cleave insulin like growth factor-binding protein 3 (IGF-BP-3) alone or in the presence of synthetic peptides (SEQ ID C-4 (SEQ ID NO 11) and A-1 (SEQ ID NO 1), table 1). In the experiments, PSA (5 µg/mL) in TBS buffer, pH 7.8 alone or with 100-fold molar excess of peptide was incubated with IGF-BP-3 (70 ng/mL) for 16 h at 37° C., after which the concentration of intact IGF-BP-3 was determined by IFMA. As control, the peptide was also added to the reaction mixture containing PSA and IGF-BP3 just before starting the immunoassay to quantify the possible interference of the peptide in the IFMA for IGF-BP-3 (labeled as BP-3+PSA+(C-4/A-1 for 0 h). PSA alone slowly cleaved IGF-BP-3 as revealed by an 30% decrease in immunoreactivity (FIG. 10). The peptides C-4 and A-1 enhanced the activity of PSA towards IGF-BP-3 leading to about 70% cleavage of IGF-BP-3.

Figure 11:
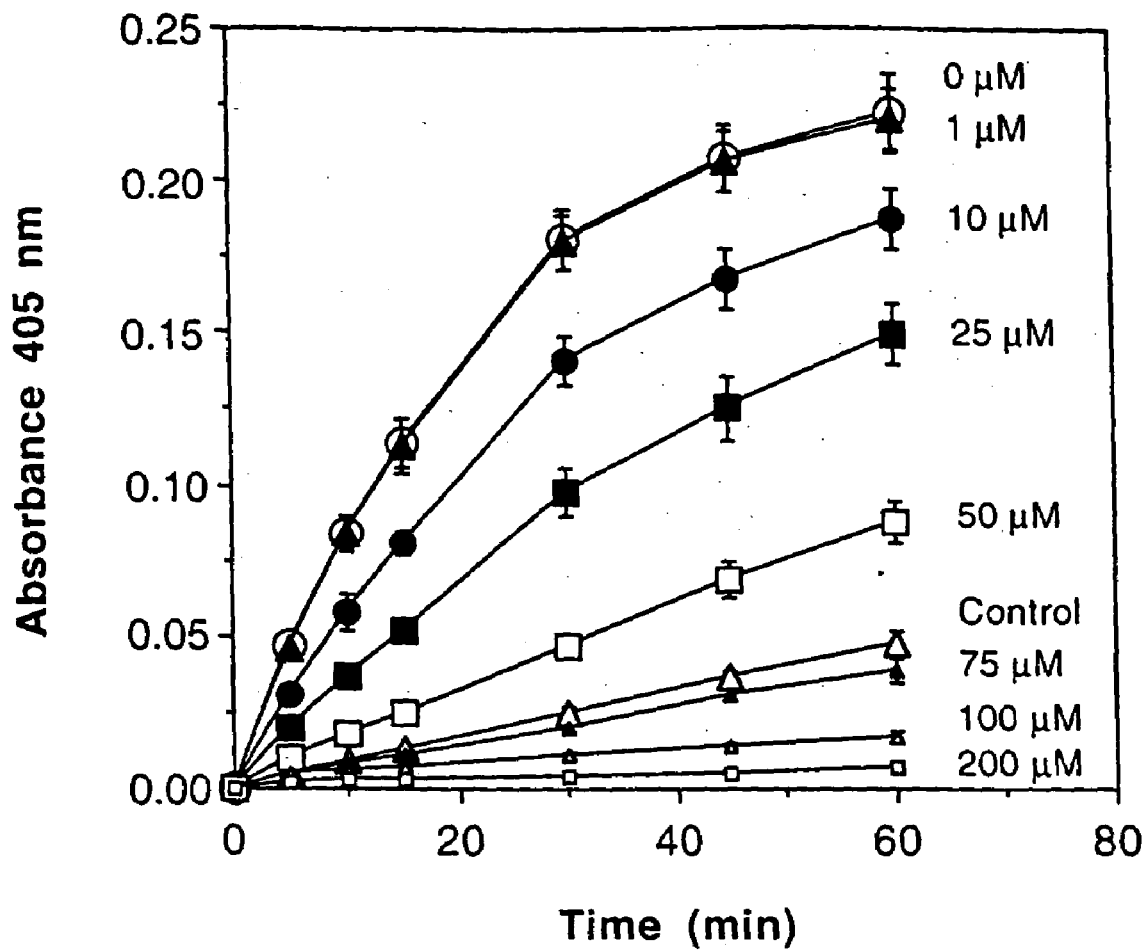
FIG. 11 presents the combined effect of GST-C-4 and $Zn^{2+}$ on the enzyme activity of PSA.

Because zinc is known to inhibit the enzyme activity of PSA, we further characterized the effect of GST-peptides on the enzyme activity of PSA by assessing the combined effect of peptides and $Zn^{2+}$. $Zn^{2+}$ negated the enhancement effect of C-4 and reduced PSA activity in a dose dependent fashion. The effect of GST-C-4 and $Zn^{2+}$ on enzyme activity was determined by incubating PSA (0.33 µM) with the same molar concentration of GST-C-4 and various concentrations of $Zn^{2+}$. The reaction was monitored by measuring absorbance at 405 nm after addition of the chromogenic substrate S-2586. The control shows the activity of PSA in the absence of peptide and $Zn^{2+}$. Data represent mean values from duplicate wells ±SE. At a $Zn^{2+}$-concentration of 75 µM the activity was similar to that of PSA in the absence of zinc and peptide, and at a concentration of 200 µM, almost total inhibition of enzyme activity was observed (FIG. 11).

Figure 12:
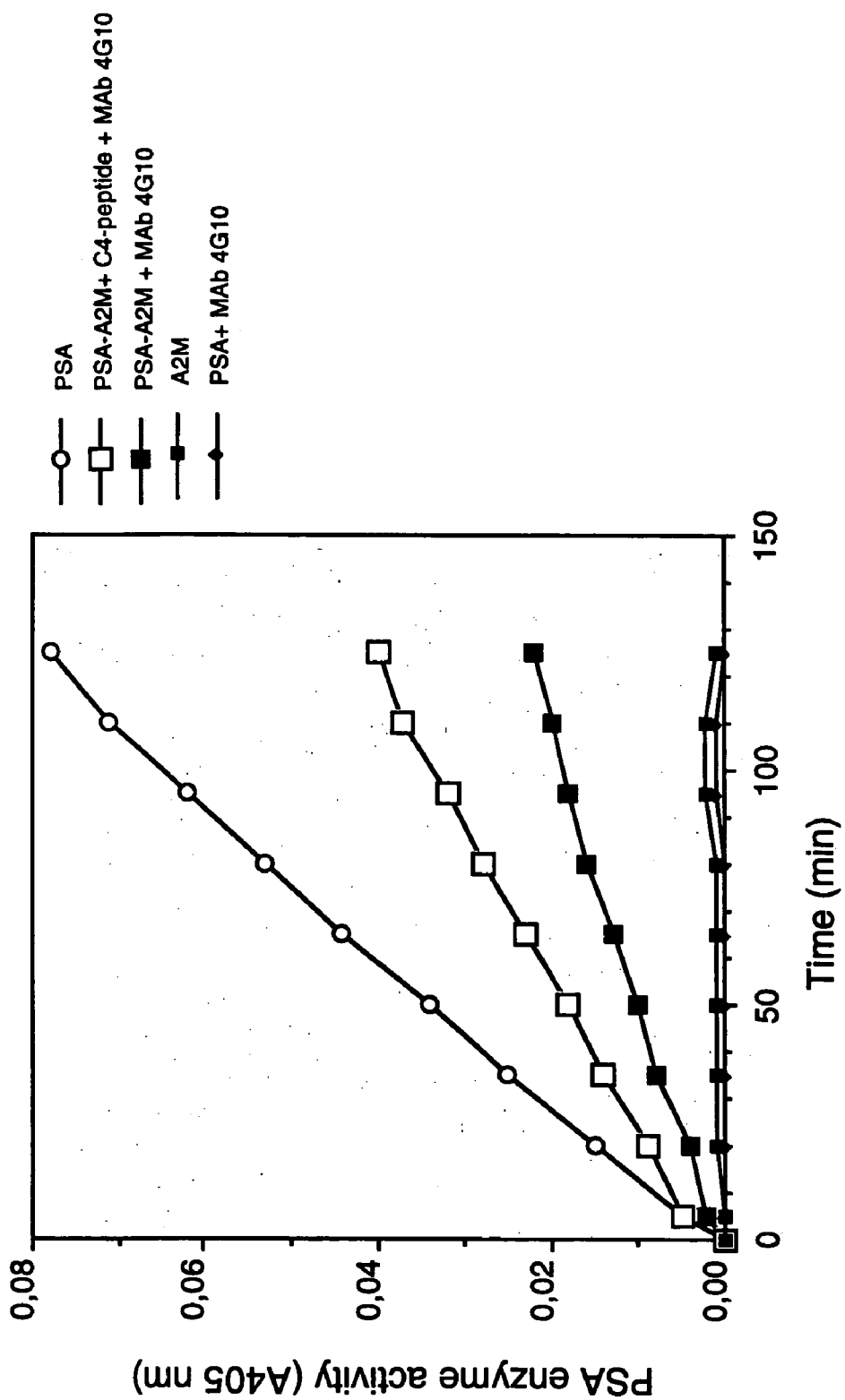
FIG. 12 depicts the effect of the chemically synthesized peptide C-4 on the enzyme activity of PSA in complex with A2M.

The effect of the chemically synthesized peptide C-4 on the enzyme activity of PSA in complex was analyzed by using purified PSA-A2M complex. It has been shown with other proteinases that after binding with A2M they still can cleave small molecular weight substrates (34). 1 µg of PSA in complex with A2M was incubated alone or with 50-fold molar excess of chemically synthesized peptide C-4 (table 1) for 1 h at 22° C. in 100 µL of TBS buffer containing 1 g/L of BSA. 10 µg of monoclonal antibody 4G10 was included to inhibit the activity due to PSA released from the complex. As control, the enzyme activity of 1 µg of free PSA was measured. The enzyme activity was monitored by measuring optical density at 405 nm with 0.2 mM S-2586 (MeO-Suc-Arg-Pro-Tyr-pNA) (Chromogenix, Mölndal, Sweden) as substrate. The enzyme activity of PSA in complex with A2M was reduced about 4-fold compared to that of free PSA, but significant activity could still be detected (FIG. 12). Thus, the active site of PSA in complex with A2M is not blocked. The possibility that the activity could be derived from PSA released from the complex was ruled out by including a MAb which inhibits the activity of free PSA completely (FIG. 12). After adding C-4 peptide the enzyme activity of A2M-complexed PSA was enhanced about 2-fold showing that the peptide could bind with PSA encapsulated by the inhibitor and exert the same effect on A2M-complexed PSA as on free PSA (FIG. 12).

The present invention provides for the first time PSA binding ligands which can specifically enhance the enzyme activity of PSA. Several PSA-binding peptides were identified using random phage-displayed peptide libraries by screening with PSA bound through a monoclonal antibody. When PSA was initially coated directly onto microtitration wells, no PSA-binding phage could be isolated. However, by capturing PSA to a monoclonal solid phase antibody specific PSA binding phage could be isolated. The monoclonal antibody used for capturing PSA does not to block the active site of PSA (27) and thus facilitated isolation of PSA-binding phage. Apparently, direct coating of PSA onto plastic changes its structure or causes an unfavorable orientation for biopanning.

Some typical amino acid residues could be identified in most of the selected peptides. The amino acid sequences CVF or CVA were present in 5 of 12 peptides derived from the degenerate $CX^8C$, $CX^{10}C$, and $CX^3CX^4CX^2C$ libraries, and tyrosine was found in 12 of 14 peptides. The peptides with the highest affinity contained four cysteines. The peptides were expressed and characterized as GST fusion proteins, which facilitated studies on the binding affinity and specificity. When expressed as fusion proteins, the peptides retained their binding activity and the relative affinities, as estimated by IFMA, were similar on phage and fusion proteins. The surface plasmon resonance experiments showed that the peptides bound to PSA with considerable affinity (Table 2).

PSA has been shown to bind $Zn^{2+}$, and the selected peptides also contain sequences resembling $Zn^{2+}$ binding sites on zinc finger proteins (35). In the presence of $Zn^{2+}$ the affinity constants of the GST-peptides increased 3-7 fold, suggesting involvement of $Zn^{2+}$ in the binding between PSA and peptides. The increase in affinity is explained by a stronger decrease in the dissociation rate than in the association rate of the complex between peptide and PSA. This may be mediated by $Zn^{2+}$ chelated between amino acid residues of PSA and the peptide. Interestingly, $Zn^{2+}$ has been shown to mediate a high affinity binding between another serine proteinase, trypsin, and its small molecule size inhibitor (36). Another possibility is that $Zn^{2+}$ stabilizes the 3-D structure of the peptide in a way similar to that by which $Zn^{2+}$ interacts with DNA-binding zinc finger proteins.

PSA-binding peptides have been produced before by the polysome selection method (11). These peptides are linear rather than cyclic, and show no similarity with the peptides isolated in the present study. Furthermore, these peptides were not shown to effect enzyme activity of PSA and the when conjugated with biotin the peptides did not show consistent binding with PSA. The affinity of our peptides is fairly typical of phage display peptides (37) but lower than those of peptides developed by the polysome technique (11). However, the differences in affinity may be accounted for by differences in measuring techniques.

The phage display peptides were selected against PSA captured to an anti PSA MAb on the wall of a microtitration well. The antibody used for capture enhances the enzyme activity of PSA, apparently by affecting the conformation of the enzyme (30). This could have contributed to the increase in peptide binding. However, PSA in solution completely inhibited the binding of GST-peptides with solid phase PSA. Thus the conformational change induced by the capture antibody was not necessary for binding of GST-peptides.

When peptides were expressed as GST fusion proteins, three molecular size forms were observed: polymer, oligomer and monomer. The polymer displayed the strongest binding to PSA, and the oligomer also bound more avidly than the monomer. This result shows that multivalent binding enhances the binding avidity. Because phage fuSE 5 expresses three to five copies of peptide inserts with the same sequence its binding is also multivalent (38). In spite of the apparent multivalent binding of GST-peptides, the monomeric peptide cleaved from the GST fusion partner substantially inhibited the binding of GST-peptide to PSA.

The peptides did not bind to chymotrypsin and cathepsin G, although the enzyme specificity of these is similar to that of PSA. They did not either bind to trypsin and hK2 which cleave C-terminal to an arginine or lysine residues. HK2 is structurally closely related to PSA showing 79% identity at the amino acid level. Thus the peptides we have selected appear to be highly specific for PSA. The GST-peptides did not either bind to PSA-serpin complexes occurring in serum, i.e. PSA-ACT and PSA-API, in which the serpins cover the peptide-binding region on PSA. Peptide-binding was also blocked by the antibodies that react with free PSA through epitopes covered in PSA-serpin complexes. These MAbs also inhibit enzyme activity (30). Some MAbs binding to other epitopes on PSA could also inhibit the binding, but to a lower degree. Taken together, these results suggest that the peptides bind close to the active site of PSA.

PSA has a restricted chymotrypsin-like enzyme activity cleaving C-terminally to tyrosine and leucine residues on semenogelin I, the natural substrate of PSA (39). However, PSA is more dependent on the sequences surrounding these amino acids than is chymotrypsin, and several residues surrounding the preferred P1 residues, tyrosine and leucine, play an important role in determining the substrate specificity and efficiency (40). PSA can also cleave after glutamine and this type of peptide substrate is more specific for PSA than those containing tyrosine and leucine at P1 (12). All the peptides selected by phage display contain tyrosine or leucine residues, often in combination with other amino acids (Y-S, Y-A, Y-D, L-V) forming cleavage sites in semenogelin I (39). However, no peptide contained more than three amino acids identical to a cleavage site in semenogelin I. All the peptides contained either two or four cysteines. Thus they probably formed tight loops, whereas the natural substrate, semenogelin I, does not contain any disulfide bridge.

Three of the four GST-peptides studied enhanced the enzyme activity of PSA against the synthetic peptide substrate S-2586, and the effect correlated with the affinity. Therefore, the peptides do not appear to interact with the catalytic triad of PSA, but rather to bind in the vicinity of the active site changing the conformation and possibly making the catalytic pocket more accessible to the synthetic substrate. The effect on enzyme activity was peptide-specific as wild type GST and GST-D-1 had no effect. $Zn^{2+}$, which inhibits the enzyme activity of PSA, reversed the stimulating effect of the peptides in a dose dependent manner.

EXAMPLE 4

Labeling and Use of PSA Binding Peptides in Affinity Chromatography

Preparation of Labeled Peptide Conjugates

Peptides were synthesized using solid phase synthesis and fmoc-chemistry. Biotin was attached in the amino terminus of the peptides during solid phase synthesis. Labeling of the peptides with the Eu-chelate was as described in Hemmilä et al., 1984 (41). 50-100 µg of peptides were labelled with 3-10-fold molar excess of Eu-chelate. After Eu-labeling the peptides were purified with reverse phase chromatography using NovaPak or Sep-Pak C18-column (Waters, Mass., USA). The columns were equilibrated with 50 mM triethylammoniumacetate, pH 7 and eluted with acetonitrile gradient. For 99m-technetium labeling the peptide was first reduced with 0.2 M mercaptoethanol. After reduction, the peptide was purified by a Sep-Pak C18 column equilibrated with 0.1 M phosphate buffer at pH 7.5 and using acetonitrile for elution. Technetium hydroxylmethylene diphosphonate (HDP)-method was used for peptide labeling with 99 mTc. 20 µg of the reduced C4-peptide was labeled with 3 mCi of 99 mTc. After labeling the peptide was purified by a Sep-Pak C18 column equilibrated with 0.1 M phosphate buffer, pH 7.5 and using acetonitrile for elution. Peptides were iodinated by the iodogen method (42).

Figure 13:
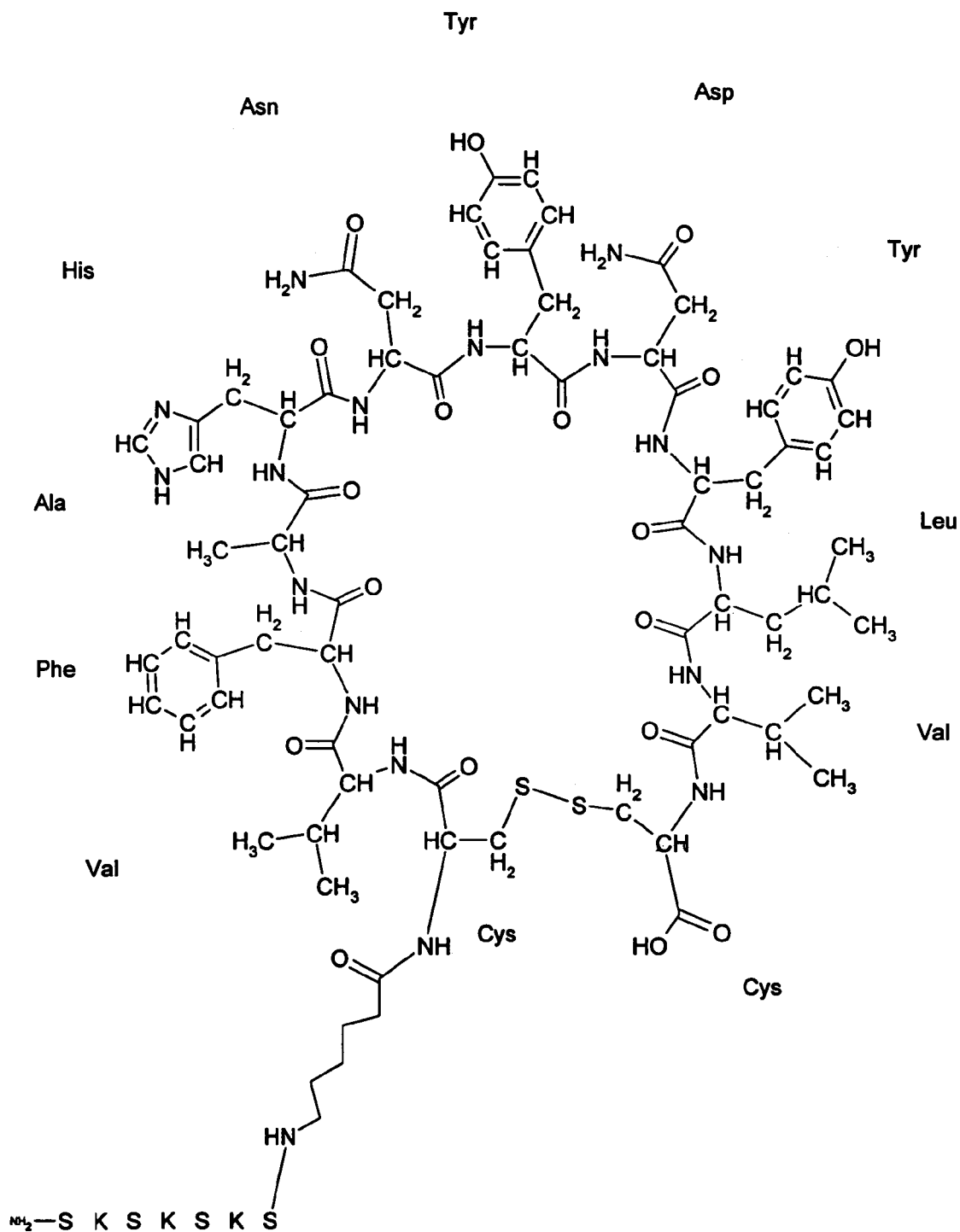
FIG. 13 shows the structure of the derivatized peptide B2.
Figure 14:
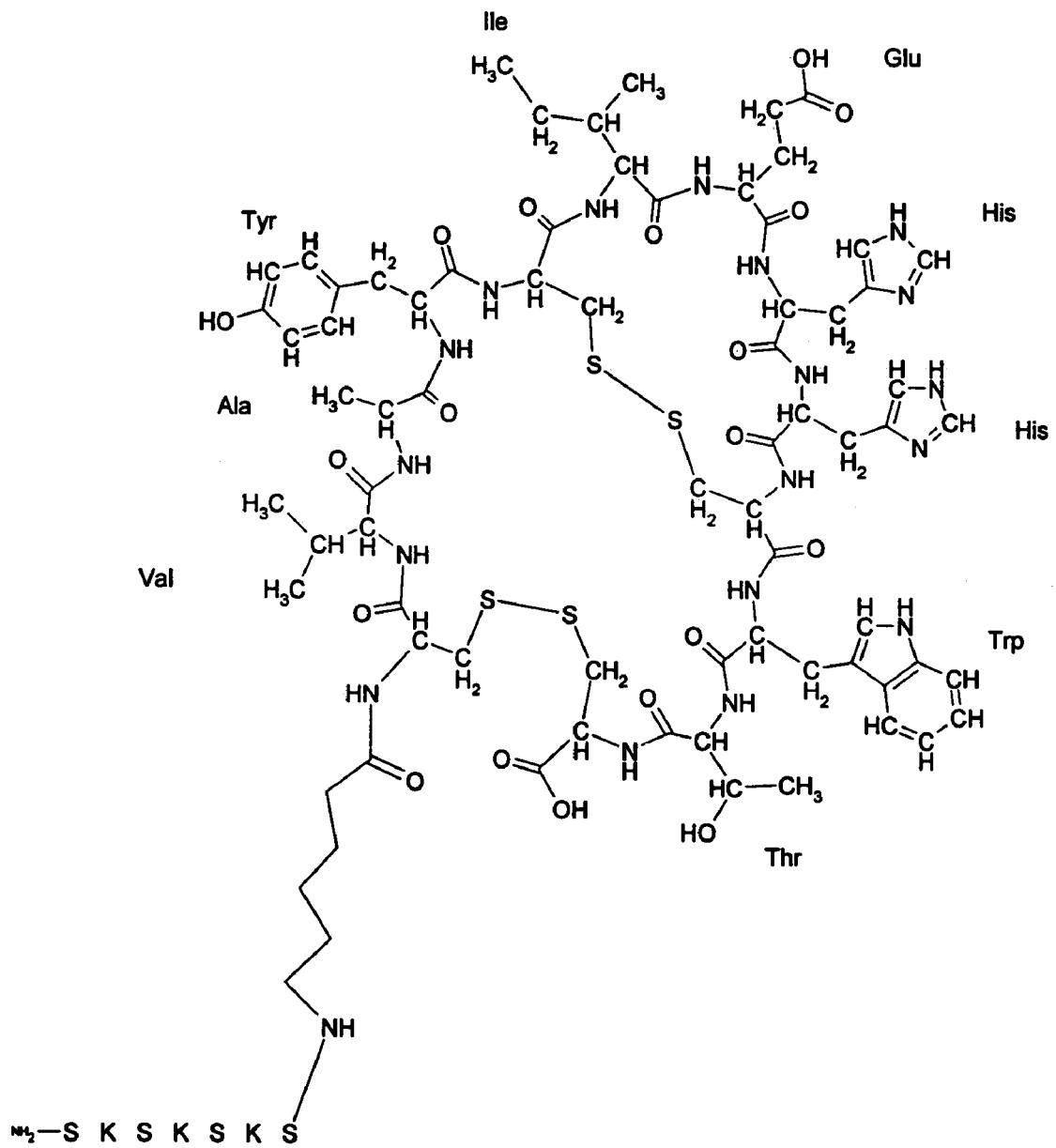
FIG. 14 shows the structure of the derivatized peptide C4.

As assayed by monitoring the effect of the peptides on the enzyme activity of PSA, the synthetic peptides could be labeled with biotin without reduction in PSA binding activity (FIG. 9). To increase the Eu labeling efficiency of the peptides we added to B2 (CVFAHNYDYLVC (SEQ ID NO:6)) and C4 (CVAYCIEHHCWTC (SEQ ID NO:11)) peptides a tail in the amino terminus consisting of serine and lysine. The structure of the corresponding B2-peptide derivative is SKSKSKS (SEQ ID NO:47)—amino caproic acid (aca)-CVFAHNYDYLVC (SEQ ID NO:6) and C4-peptide derivative is SKSKSKS (SEQ ID NO:47)—aca-CVAYCIEHHCWTC (SEQ ID NO:11). The structures of these derivatized B2 and C4 peptides are also shown in FIGS. 13 and 14, respectively.

Figure 15:
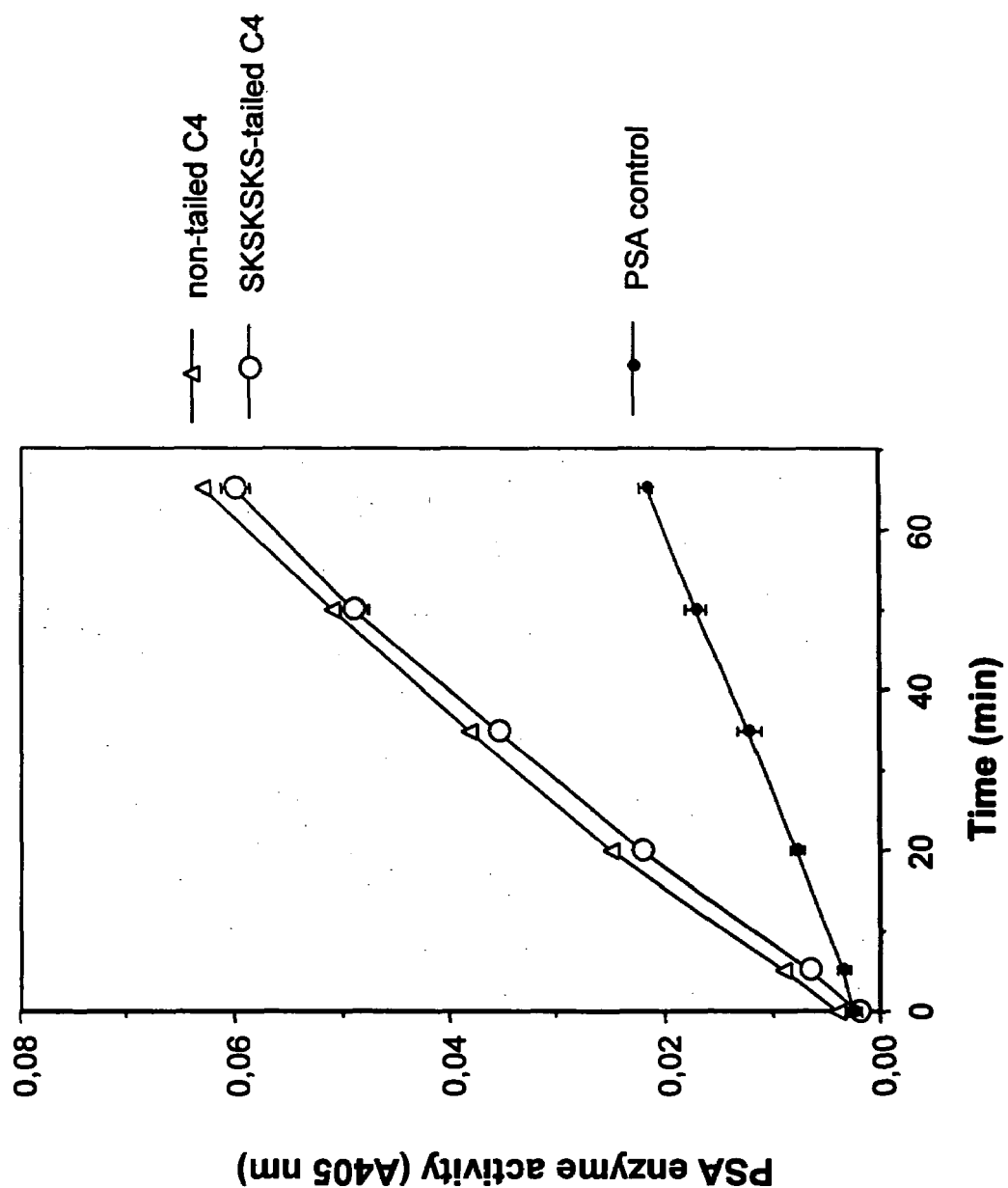
FIG. 15 indicates the effect of SKSKSKS (SEQ ID NO:47)-tailed peptide C4 on the enzyme activity of PSA.

FIG. 15 shows the effect of SKSKSKS (SEQ ID NO:47)-tailed peptide C4 on the enzyme activity of PSA. PSA (0.33 mM) was incubated with non-tailed and SKSKSKS (SEQ ID NO:47)-tailed C4 (in 30-fold molar excess) for 1 h, after which the chromogenic substrate S-2586 was added and enzyme activity was monitored by measuring the absorbance at 405 nm. Data represent mean values from duplicate wells ±SE. This result showed that the addition of the tail did not affect the binding activity of the peptides.

Figure 16:
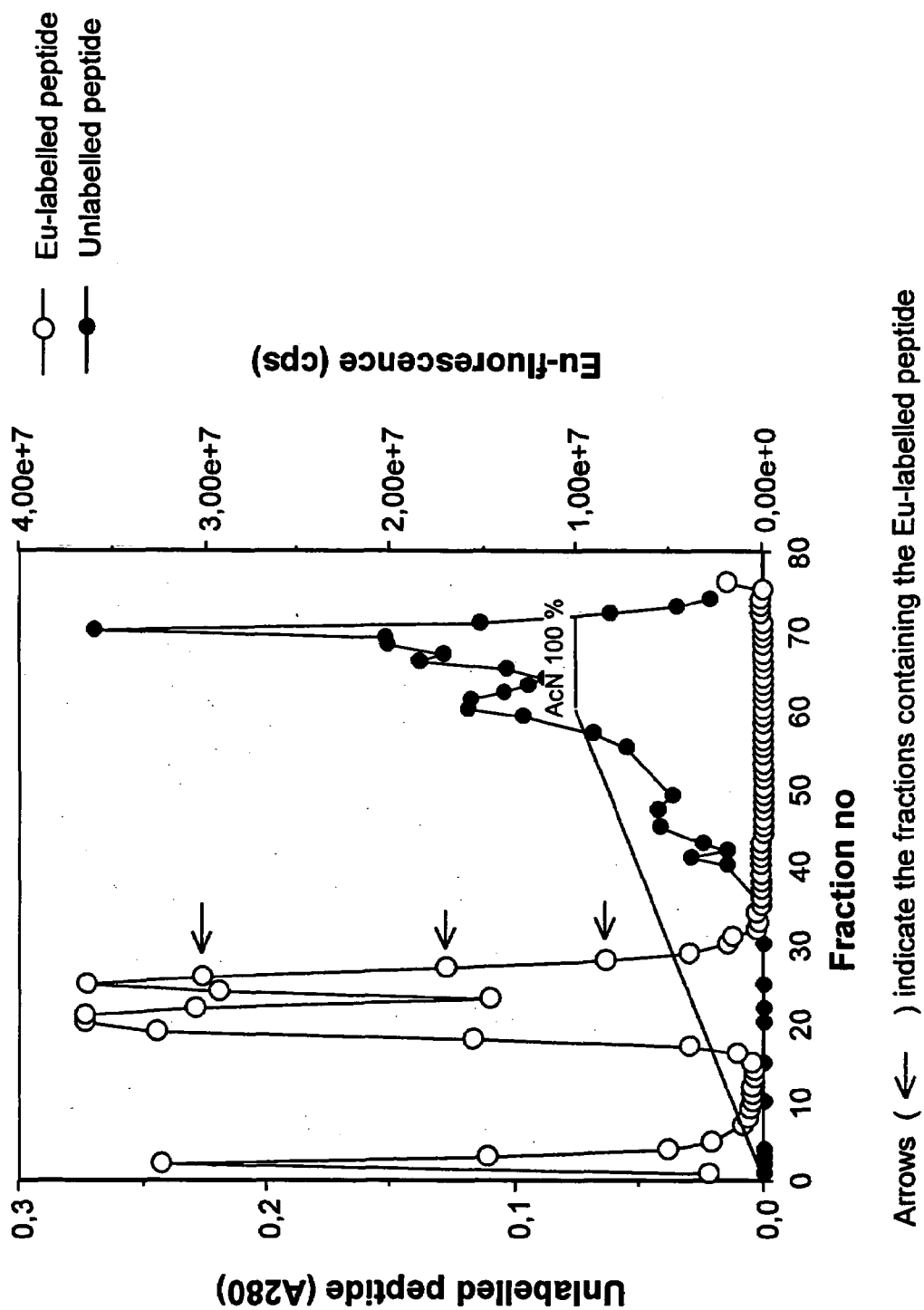
FIG. 16 shows the fractionation of an Eu-labelling reaction mixture of peptide C4.

After Eu-labeling the peptides were purified by C18 chromatography. FIG. 16 shows the fractionation of Eu-labelling reaction mixture containing 50 µg C4 peptide on C18 Sep-Pak column. Acetonitrile (AcN) gradient was used for elution. Flow rate was 0.5 mL/min and 1 mL fractions were collected. For comparison, the elution curve of unlabelled C4 peptide in the same column is shown. This result shows that the Eu-labelled peptide can be separated from the unlabelled peptide by C18 chromatogaphy.

Figure 17:
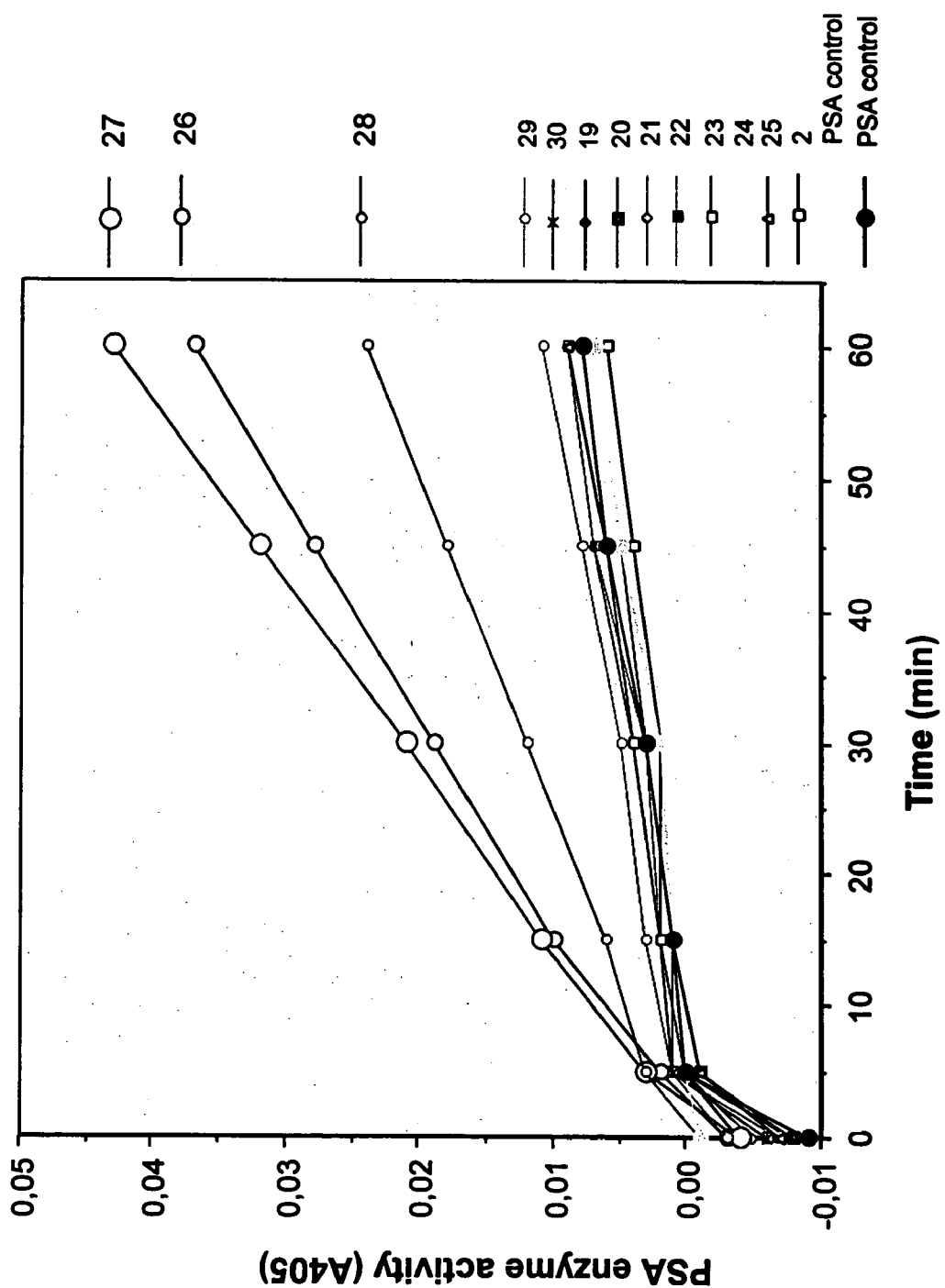
FIG. 17 indicates the effect of the various fractions of the C18 chromatography shown in FIG. 16 on enzyme activity of PSA.

FIG. 17 shows the effect of the fractions from the C18 chromatography (FIG. 16) on enzyme activity of PSA. PSA (0.33 µM) was incubated with 100 µL aliquots of the fractions obtained by C18 chromatography of the Eu-labelling reaction mixture of C4 (FIG. 16) for 1 h, after which the chromogenic substrate S-2586 was added and enzyme activity was monitored by measuring the absorbance at 405 nm. Fractions 26-28 contained the Eu-labelled C4-peptide because they enhanced the enzyme activity of PSA strongly (FIG. 17). As control the enzyme activity of PSA alone was measured. The elution position of Eu-labelled C4 is also indicated by arrows in FIG. 16. This result shows that Eu-chelate can be attached to the peptides without affecting their PSA binding activity.

Figure 18:
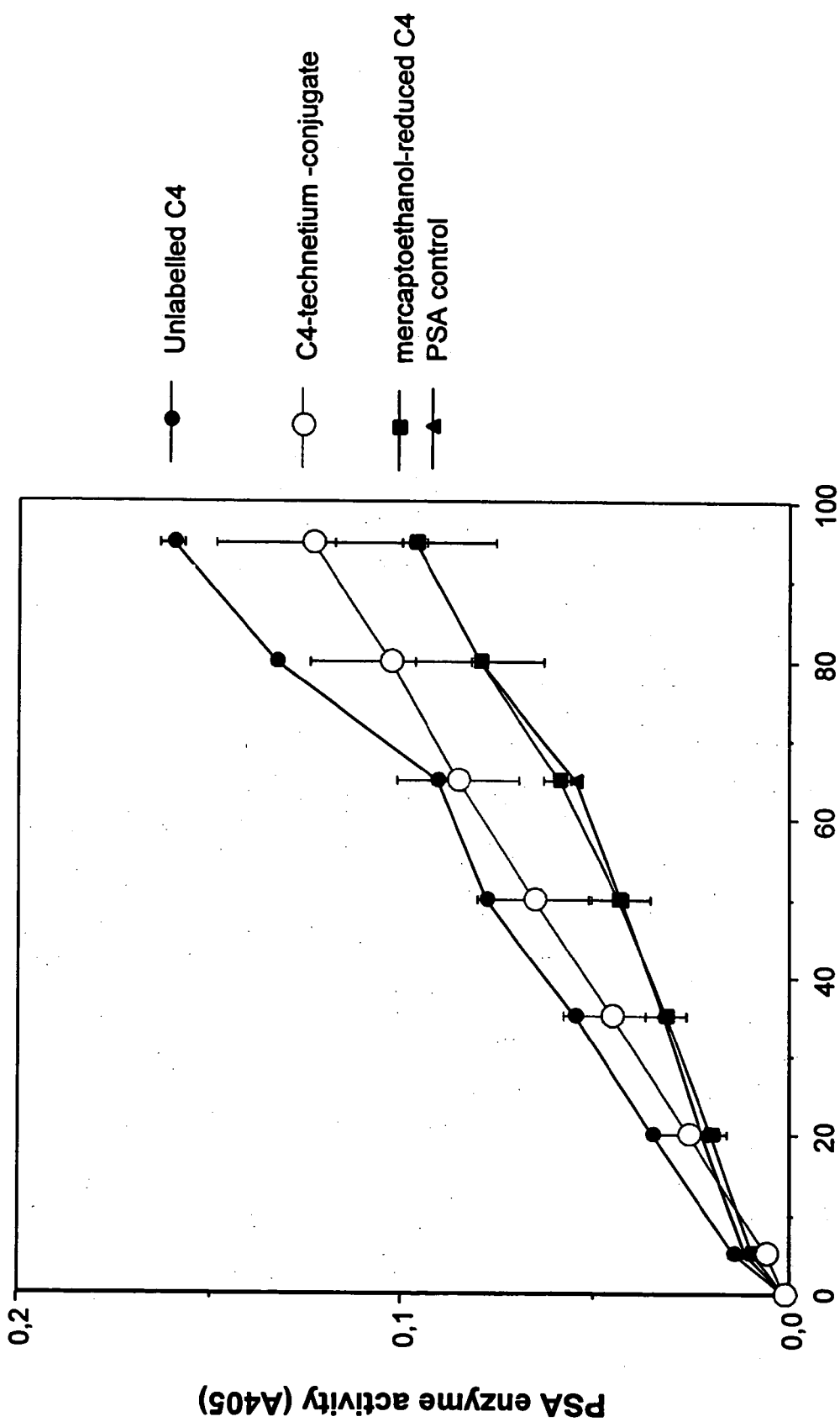
FIG. 18 shows the effect of technetium labeling on the binding activity of C4-peptide.

FIG. 18 shows the effect of technetium labeling on the binding activity of C4-peptide. PSA (0.33 µM) was incubated with Tc99m-labeled C4 (30-fold molar excess) for 1 h, after which the chromogenic substrate S-2586 was added and enzyme activity was monitored by measuring the absorbance at 405 nm. Data represent mean values from duplicate wells ±SE. The effect of unlabelled C4 on PSA is shown for comparison. As control, the effect of linear C4 (reduced by mercaptoethanol) on PSA activity and the activity of PSA alone are shown. This result showed that technetium labeling between thiol-sulfurs of a C4-peptide reduced the binding by about 50%.

Figure 19:
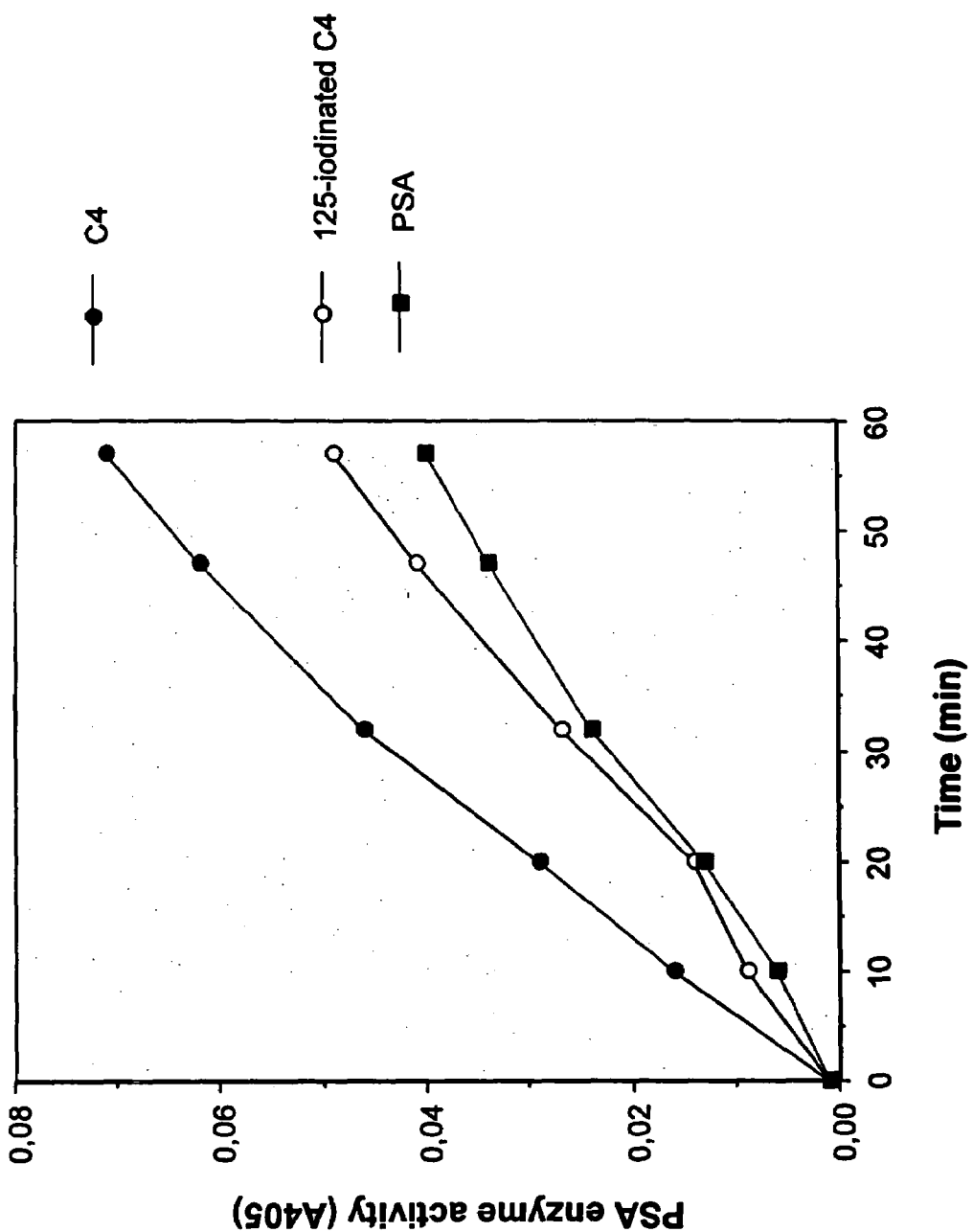
FIG. 19 shows the effect of iodination on the PSA binding activity of C4 peptide.

FIG. 19 shows the effect of iodination on the PSA binding activity of C4 peptide. 20 µg of the peptide was iodinated by the Iodogen method. After iodination the peptide was purified by using C18 Sep-Pak column. PSA (0.33 µM) was incubated with 125I-labeled C4 (30-fold molar excess) for 1 h, after which the chromogenic substrate S-2586 was added and enzyme activity was monitored by measuring the absorbance at 405 nm. For comparison, the effect of unlabelled C4 on PSA activity and the activity of PSA alone are shown. This result shows that 125-iodination of the C4-peptide (CVAY-CIEHHCWTC (SEQ ID NO:11)) by the iodogen method almost completely destroyed its binding activity. This suggests that the single Tyr residue in this peptide is important for binding.

These results show that various label groups can be coupled to the PSA binding peptides without affecting their binding activity, especially when the coupling is directed aminoterminus or to a tail added to the original peptide sequence. After chelating Tc99m between the thiol groups of the peptide the C4 peptide retained about half of its activity.

PSA Binding Peptides in Affinity Chromatography

The peptide affinity gels were prepared by coupling the lysine-serine-tailed derivatives of the peptides B2 and C4 (FIGS. 13 and 14) to activated CH-Sepharose 4B (Amersham-Pharmacia Biotech) according to the instructions of the manufacturer. The coupling was performed by using an equimolar concentration of the peptide as compared to the concentration of the coupling sites in Sepharose. For peptide affinity chromatography the columns were equilibrated with Tris-buffered saline, pH 7.8 or with the same buffer containing 100 µM $ZnCl_2$. After applying the sample the column was washed with Tris-buffered saline, pH 7.8. The column was eluted with a linear gradient decreasing pH using 10 mM ammoniumacetate, pH 6.5 and 10 mM sodium acetate-buffer, pH 3.5, or stepwise gradient using buffers with pH 6 and 4 for elution. Binding of PSA to these gels was monitored by PSA immunoassay. The identity of PSA eluted form the peptide affinity columns was further evaluated by SDS-PAGE (43) and immunoblotting (44). In immunoblotting experiments the proteins separated by SDS-PAGE were transferred to PVDF membranes and immunoreacted with a polyclonal anti-PSA antibody (Dako, Denmark).

Figure 20:
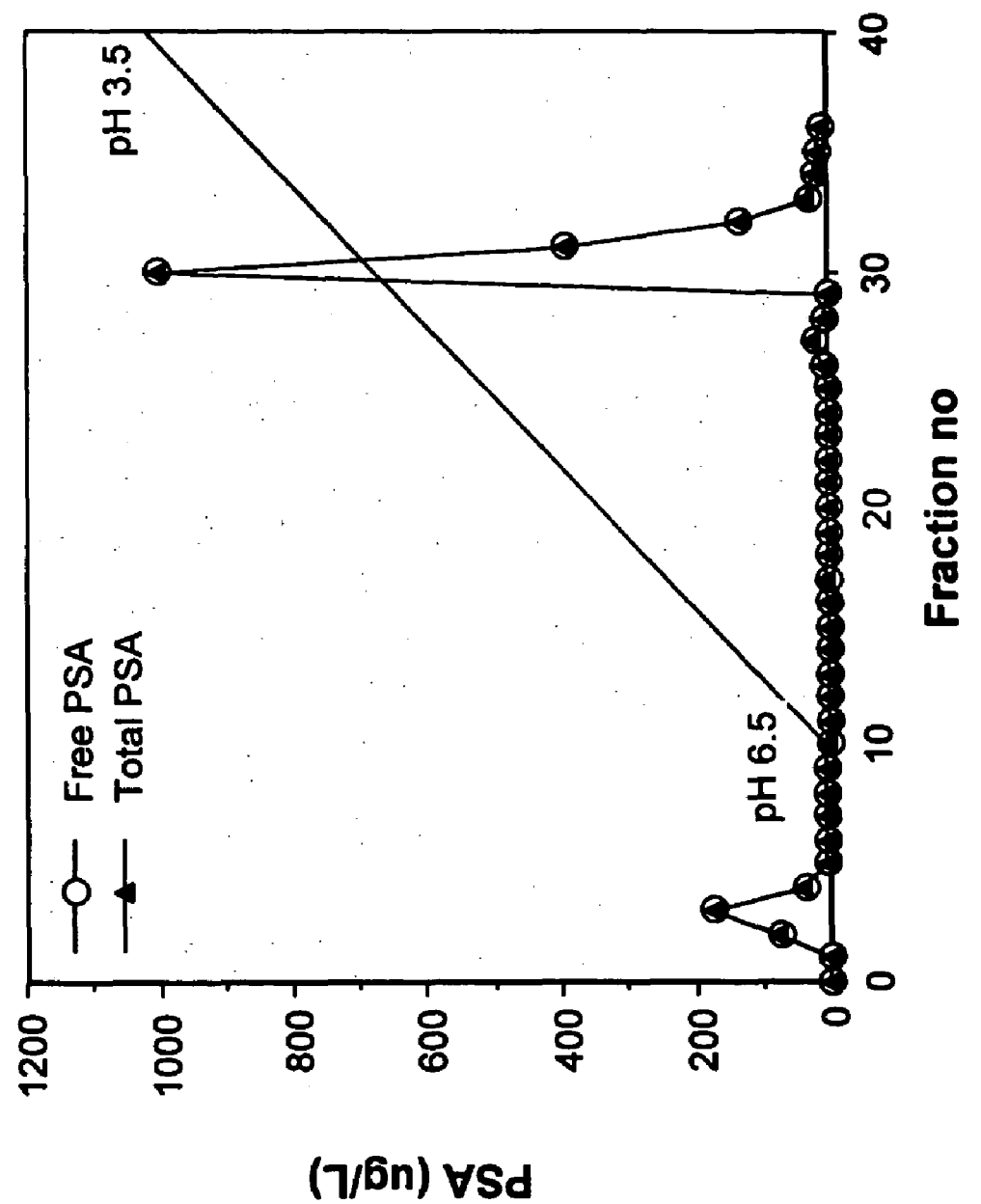
FIG. 20 shows the fractionation of seminal plasma sample by B2 peptide affinity chromatography in the presence of 100 µM $Zn^{2+}$.

FIG. 20 shows the fractionation of a seminal plasma sample by B2 peptide affinity chromatography in the presence of 100 µM $Zn^{2+}$ PSA was precipitated from seminal fluid by ammonium sulfate, after which it was diluted in equilibration buffer and applied into the column. After washing the column PSA was eluted with gradient decreasing pH. The flow rate was 0.5 mL/min and fractions of 1 mL were collected. About 80% of the applied PSA was bound to the column and eluted when pH was decreased (FIG. 20).

Figure 21:
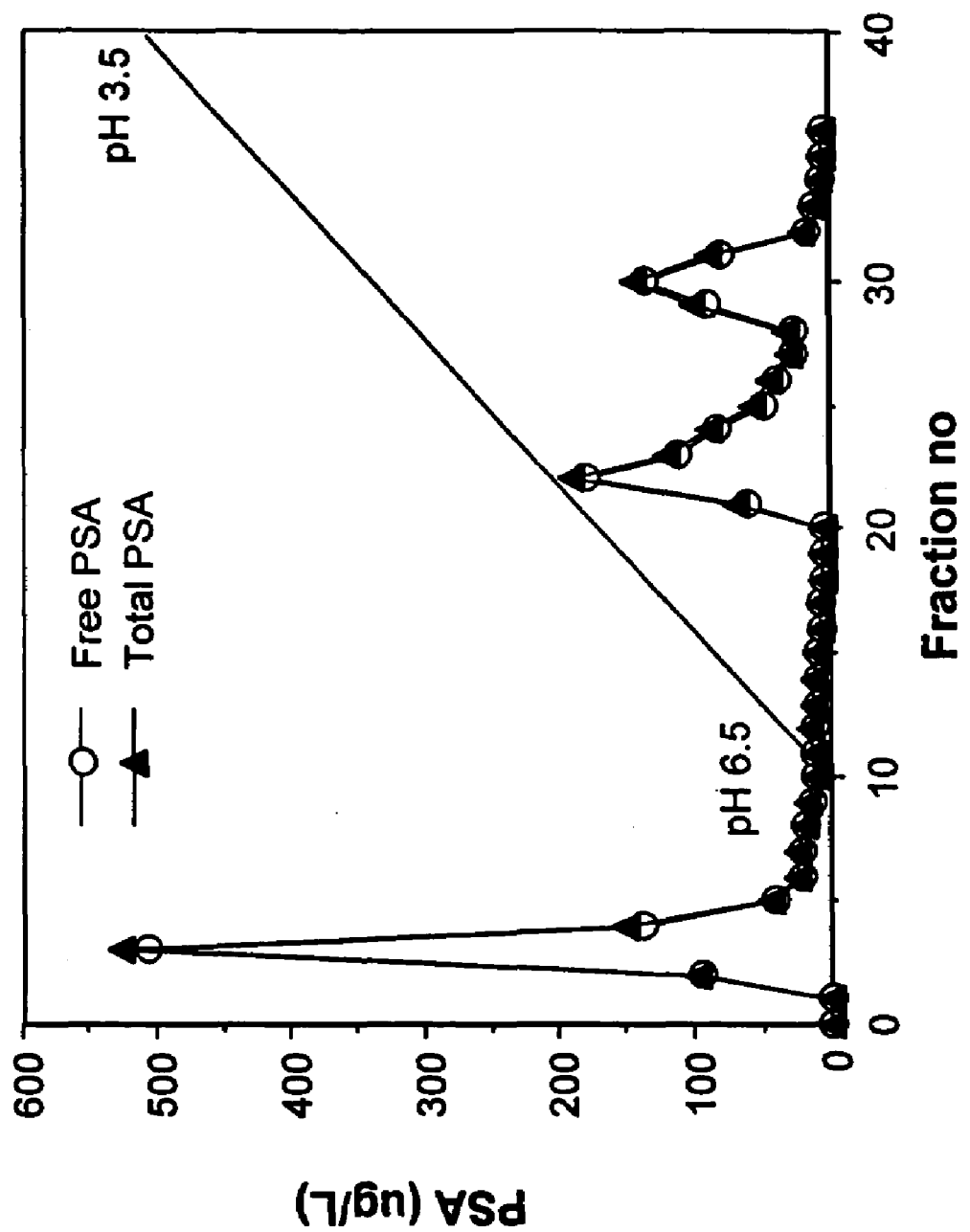
FIG. 21 shows the fractionation of seminal fluid as above in FIG. 20 but without $Zn^{2+}$
Figure 22:
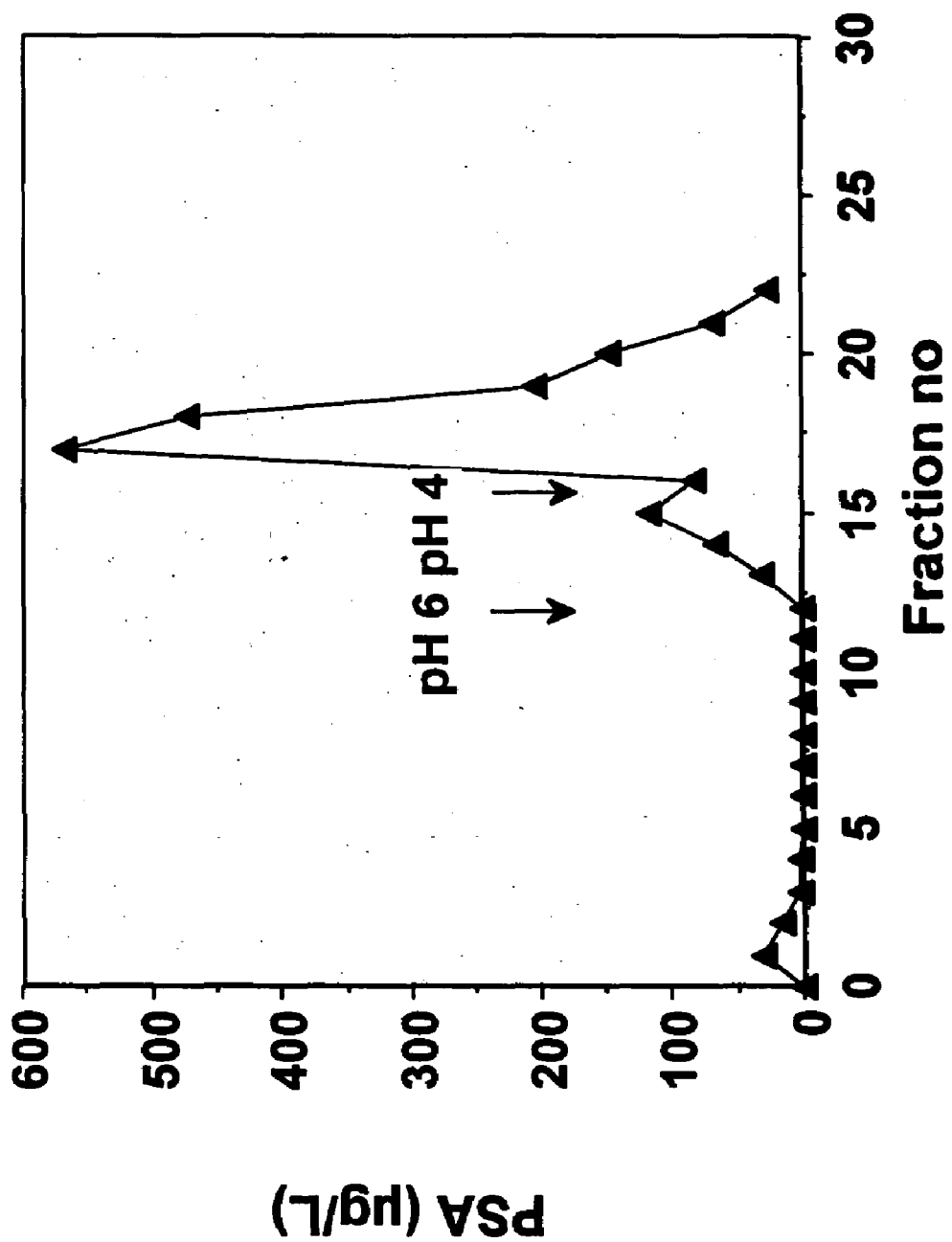
FIG. 22 shows the elution of PSA from a C4-peptide column at different pH-values.

In FIG. 21 it is shown the fractionation of seminal fluid as above in the FIG. 20, except $Zn^{2+}$ was omitted from the buffer. When $Zn^{2+}$ was omitted, nearly half of the seminal fluid PSA applied bound to the column and after eluting with gradient decreasing pH two peaks were recovered (FIG. 21). Also when fractionating seminal fluid with C4-peptide-Sepharose in the presence of $Zn^{2+}$, about 80% of PSA bound to the column and eluted as two peaks with stepwise gradient decreasing pH (FIG. 22). If Zn was omitted, about 80% of applied PSA was unbound.

Figure 23:
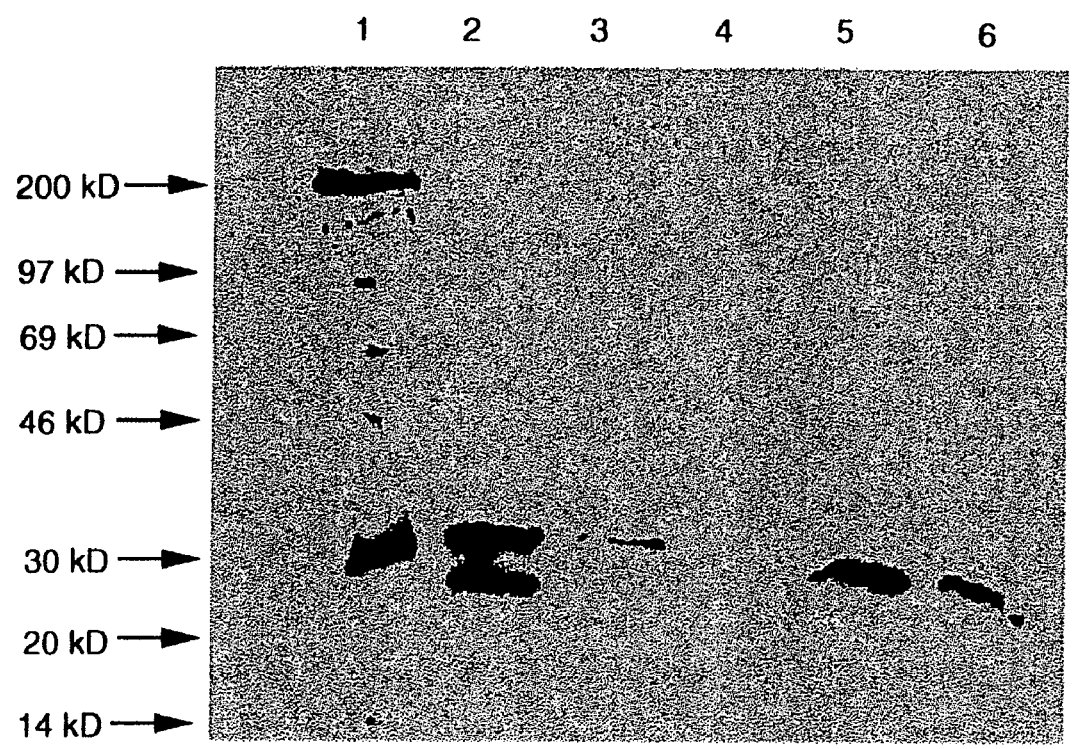
FIG. 23 shows the immunoblot analysis after SDS-PAGE under non-reducing conditions of PSA-containing fractions obtained from an affinity column of peptide B2.

The identity of the PSA forms separated by the B2-peptide affinity chromatography was evaluated by SDS-PAGE and immunoblotting using polyclonal anti-PSA antibody. FIG. 23 shows the immunoblot analysis after SDS-PAGE under non-reducing conditions of the PSA containing fractions from the B2 peptide affinity column (FIGS. 20 and 21). The samples were as follows: lane 1: MW-marker, lane 2: unbound PSA; $Zn^{2+}$ included (fraction no 4 in FIG. 20), lane 3: unbound PSA; $Zn^{2+}$ not included (fraction no. 4 in FIG. 21), lane 5: bound PSA; $Zn^{2+}$ included (fraction no 30 in FIG. 20), lane 6: bound PSA; $Zn^{2+}$ not included (fraction no 30 in FIG. 21).

Figure 24:
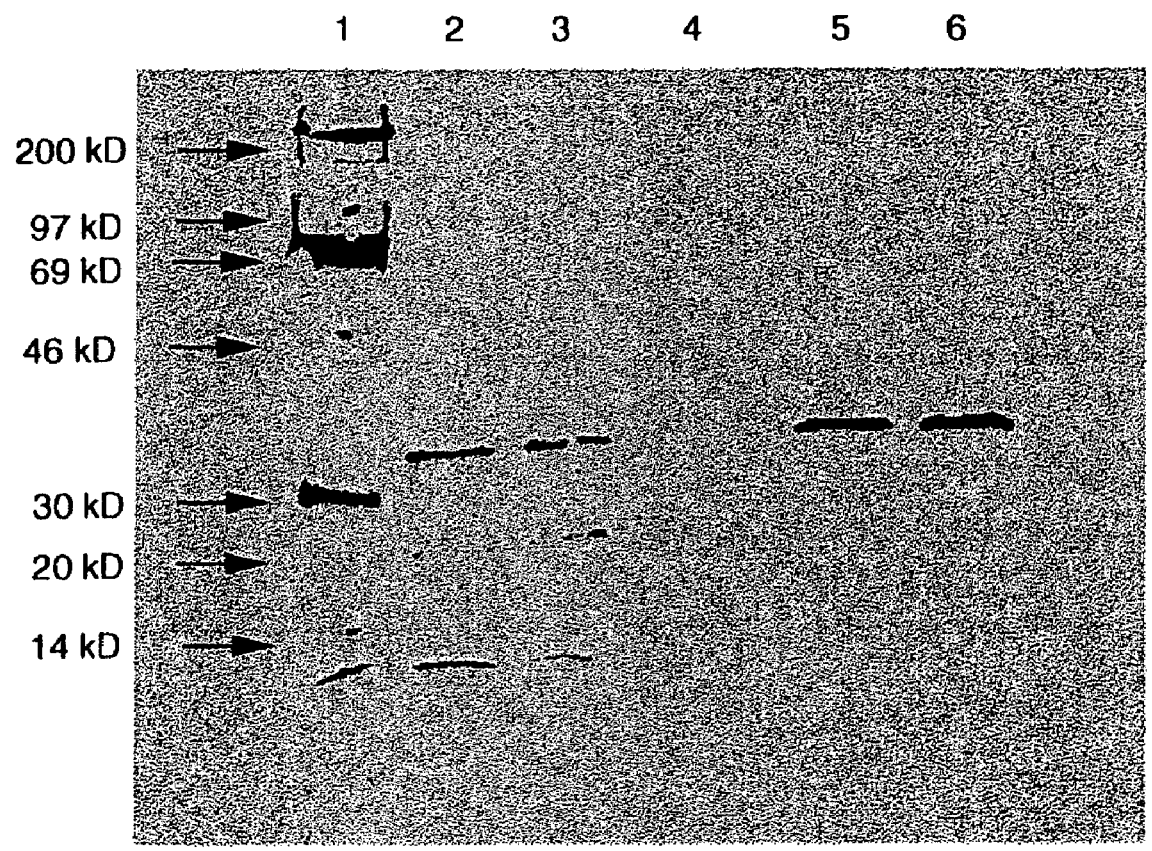
FIG. 24 shows the corresponding (cf FIG. 23) immunoblot analysis after SDS-PAGE under reducing conditions.

FIG. 24 shows the immunoblot analysis after SDS-PAGE under reducing conditions of the PSA containing fractions from the B2 peptide affinity column (FIGS. 20 and 21). The samples were as follows: lane 1: MW-marker, lane 2: unbound PSA; Zn2+ included (fraction no. 4 in FIG. 20), lane 3: unbound PSA; Zn2+ not included (fraction no 4 in FIG. 21), lane 5: bound PSA; $Zn^{2+}$ included (fraction no. 30 in FIG. 20), lane 6: bound PSA; $Zn^{2+}$ not included (fraction no. 30 in FIG. 21).

The immunoblotting analysis under non-reducing conditions of the fractions from the B2-peptide column revealed band with MW of about 30 kD both in unbound and bound fractions of PSA immunoreactivity (FIG. 23). This corresponds to the size of free PSA. However, immunoblotting after SDS-PAGE under reducing conditions revealed in the fractions containing the unbound PSA bands corresponding to molecular weights of about 10 and 20 kD (FIG. 24). These correspond to the sizes of the fragments of PSA derived from the proteolytically cleaved or nicked PSA. Some intact PSA was also detected in the unbound fraction of PSA (FIG. 24). The bound form of PSA only contained a 30 kD band under reducing conditions showing that it consists only of intact PSA.

Figure 25:
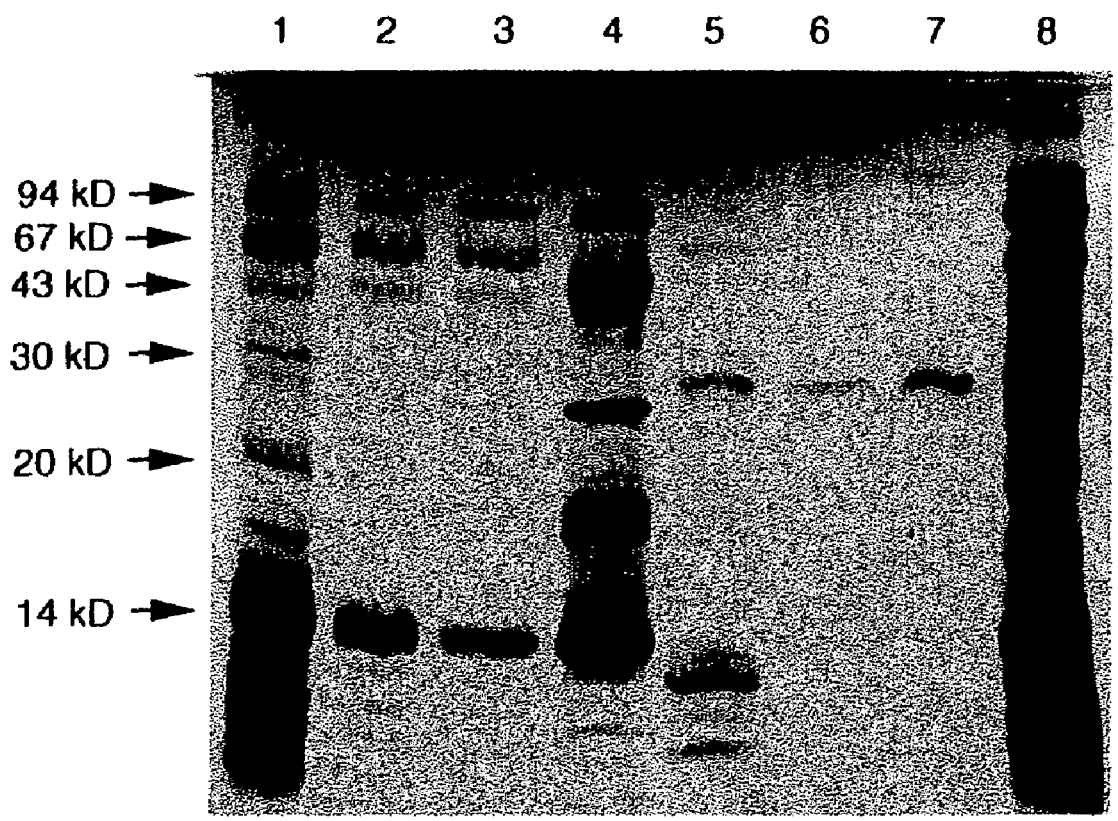
FIG. 25 shows SDS-PAGE under reducing conditions of seminal fluid fractionated by the B2 peptide column.

The SDS-PAGE analysis also showed that the peptide columns can be used to purify PSA from seminal fluid. FIG. 25 shows SDS-PAGE under reducing conditions of seminal fluid fractionated by the B2 peptide column. The samples were as follows: lanes 1, 2 and 3: unbound PSA, lane 4: MW marker, lanes 5, 6 and 7: PSA eluted at pH 6, 5 and 4, respectively, lane 8: seminal fluid. This result shows that by fractionating the seminal fluid with PSA binding peptide column most of the contaminating seminal fluid proteins could be removed by the one step peptide affinity chromatography.

These results show that these peptides can be used for purification of PSA and for differentiation between various forms of free PSA. Because these peptides possess novel binding specificities towards PSA, i.e. they bind specifically with the intact form of free PSA, they are potentially useful in development of assays with improved accuracy for prostate cancer.

EXAMPLE 5

Conformational and Biochemical Analysis of the Cyclic Peptides which Modulate Serine Protease Activity Materials and Methods Peptide synthesis: The peptides were synthesized using PerSeptive 9050 Plus automated peptide synthesizer, with Fmoc strategy, TBTU/DIPEA as the coupling reagent and NovaSyn TGA with 4-hydroxymethylphenoxyacetic acid linker as the solid phase (Novabiochem, Läufelfingen, Switzerland). The side-chain protecting groups used in synthesis were trityl (Trt) for Asn, Qln and His, O-tert-Butyl (OtBu) for Glu and Asp, t-Butyloxycarbonyl (Boc) for Trp and tert-Butyl (tBu) for Ser, Thr and Tyr. For Cys both Acetamidomethyl (Acm) and Trt protetion groups were used. For peptides A-1, B-2 and their modifications Cys(Acm) was used in the Cys position 1: C(Acm)VFTSDYAFC(Trt) (SEQ ID NO: 1) and C(Acm)VFAHNYDYLVC(Trt) (SEQ ID NO:6), for peptide C-4 and its modifications Cys(acm) was used in postions 2 and 3: C(Trt)VAYC(Acm)IEHHC(Acm)WTC(Trt) (SEQ ID NO: 11). During the cleavage from the resin with 96% TFA, the Acm-protection group remains in the Cys-side chain. For synthesis of head-to-tail cyclic C-4 peptide with one cystein bridge Cys(trt) and Fmoc-Glutamic acid with α-allyl ester (Fmoc-Glu-Oall) was used. Fmoc-Glu-Oall was first attached on the resin via the side chain carbonyl group. The synthesis continued from Glu(7) to His(8) (in parent sequence) NH$_2$— HHCWTVAYCIE (SEQ ID NO:46)-Oall. The cyclisation occurred on the resin before cleavage.

The peptides were purified by HPLC (Shimadzu, Japan) with C$_{18}$ reverse phase column and acetonitrile (ACN) as eluent (0.1% TFA in H$_2$O/0-60% ACN gradient for 60 min) and verified with MALDI-TOF mass spectrometer (Bruker, Germany) and the purity was determined by analytical HPLC with 240×1.4 mm C18 column 0-60% ACN for 30 minutes.

Cyclisation of the peptides: Peptides with cysteins (Acm) were cyclised by using Iodination method. Lyophilised peptide was dissolved in 50% acetic acid (AcOH) with the concentration of 2 mg/ml. 1 M HCl (0.1 ml/mg of peptide) was added followed immediately by 0.1 M iodine solution in 50% AcOH (5 eq./Acm). Solution was stirred vigorously at room temperature for 30 to 40 minutes. Reaction was stopped with 0.1 M sodium thiosulphate. After filtering (0.45 μm) peptides were purified with HPLC as described above. The formation of the sulphur bridges was verified with MALDI-TOF mass spectrometer (Brüker analytic GMBH, Karlsruhe, Germany).

Head-to-tail cyclization was started with the cleavage of the Oall-group from the carbonyl group of Glu. Three equivalents of palladium (Pd(PPh$_3$)$_4$ were dissolved into ChCl$_3$-AcOH N-methylmorpholine under argon. Palladium was added on the resin and stirred for 2 hours at RT under argon. After incubation the resin was washed with 0.5% diisopropylethanolamine DIPEA in DMF and 0.5% sodium diethylthiocarbamate in DMF to remove the catalyst. After removal of the Allyl-group a head-to-tail peptide bond was formed with equimolar concentrations of 0.6 M HTBU and 0.9 M DIPEA in DMF after stirring 2 hours at RT. After coupling the resin was washed with DMF, DCM and dried. After cleavage the peptide was purified with HPLC and dissolved in 0.1 M (NH$_4$)HCO$_3$. The sulphur bridge was formed by air-oxidation. The formation of the peptide bond and the sulphur bridge was verified with MALDI-TOF.

PSA activity measurements: The effect of different peptides on the activity of PSA was studied by using chymotrypsin substrate S-2586 (MeO-Suc-Arg-Pro-Tyr-pNA) (Chromogenix, Mölndal, Sweden). 77 pmoles (2 μg) of PSA, substrate and 10 μmoles of different peptides were incubated in Tris-buffer (10 mM Tris and 150 mM NaCl at pH 7.8) with 0.2 mM concentration of the substrate at room temperature. PSA reaction without any peptide was used as basic level control. Reaction was measured after 60 minutes incubation at 405 mm using Multiscan RC photometer (Labsystems, Finland). The effect of the peptides was calculated as a ratio from the OD value of PSA-peptide complex to PSA alone after 60 minutes incubation.

NMR Spectroscopy: NMR samples were prepared by dissolving purified and lyophilized peptides in 600 μl DMSO-d$_6$ to 5-10 mM. The pH of the samples were not tested. All spectra were recorded at 300-320 K on a Brüker Avance 500 NMR spectrometer (Brüker analytic GMBH, Karlsruhe, Germany) operating at a frequence of 500 MHz for $^1$H. All one-dimensional experiments were recorded at five different temperatures in the range from 300 K to 320 K. The temperature coefficients (dδ/dT) of the amide protons were calculated by analysing the chemical shifts at these five temperatures. All two-dimensional experiments were recorded either at 305 K or 310 K, depending on the quality and clarity of the spectra. All chemical shifts are reported with respect to the DMSO peak at 2.50 ppm. For all 2D experiments, standard pulse programs from the Brüker software library were used. TOCSY spectra were recorded with mixing times of 80 ms by means of MLEVTP (45) mixing sequence with TPPI phase cycling. NOESY (48) spectra were mainly recorded with mixing times of 400 ms for A-1, 420 ms for B-2 and 300 ms for C-4 using TPPI phase cycling. Various mixing times were tested and the best were decided based on quality and clarity of spectra's. NOE-build up curves were not determined. As well some COSY (c) spectra were recorded with mixing times of 30 ms. The data sets were processed with a phase-shifted sine bell functions. Typically the data were recorded with a resolution of 1024 points for both $t_1$ and $t_2$.

Structure calculations: Structure calculations were performed by DYANA software (46). NOE-intensities were approximately calibrated relative to the β-protons of Tyr7 and Cys10 and aromatic ring protons of Tyr7 in A-1, the aromatic ring protons of Tyr7 in B-2 and the aromatic ring protons of Trp11 in C-4. NOE correlations were classified as either strong (1.8 to 2.7 Å), medium (1.8 to 3.5 Å) or weak (1.8 to 5.0 Å). Some pseudo-atom corrections of 1.5 Å for methyl, 1.0 Å for methylene protons and 2.0 Å for tyrosine ring protons were added when needed (52). Dihedral angles were not mainly restricted because of fluctuation of 3-D structures (52).

Results

The most important data derived from NMR measurements, were sequential and long range nuclear Overhauser effects, C$^\alpha$H conformational shifts and temperature coefficients of amide protons. The sequential NH(i)/NH(i+1) NOE cross peaks are always an evidence of a more or less turned conformation. It has been suggested that the distance between amide protons has to be less than 3 Å before it is possible to observe NOE arising from dipolar contact between them. The understanding is that this dipolar contact primarily arises from right-handed ax-conformation. The existence of the observed strong sequential C$^\alpha$H(i)/NH(i+1) cross peaks were evidence of β-conformation. When they both exist in the same residue, there was dynamical equilibration between two conformations. Intensities of the sequential NH(i)/NH(i+1) and C$^\alpha$H(i)/NH(i+1) and intraresidual C$^\alpha$H(i)/NH(i) NOE-correlation's were indicative for the main event of backbone structural rigidity or dynamic behaviour.

The use of a strong hydrogen-bond-accepting solvent, such as DMSO-d$_6$, usually results in a downfield shift of solvent-exposed NH groups in peptides (50). Most of the NH chemical shifts lie either at the same location as or downfield from the random coil chemical shift. There were also significant upfield shifting among NH chemical shifts. The solvent exposure of NH groups were also detected by determining the temperature coefficients of NH groups. Every peptide investigated had an NH group or groups showing very low Δδ/ΔT-values (<3 ppm/K) characteristic for strong solvent shielding (Raghothama et al. 1996). We also found a couple of moderate Δδ/ΔT-values (3-5 ppm/K) which needed to be discussed. Chemical shifts and Δδ/ΔT-values of NH groups for each peptide are listed in Table 6. Part of the NH peaks were broadened indicating solvent-exposed NH groups or conformational fluctuation and dynamic behaviour (52, 50). Because of a broadening of all $^3J_{NHC\alpha H}$ could not be detected very well. Detected coupling constants were usually between 6.0 and 8.0 Hz, revealing no more information about structure.

Because of the low solubility in water, (especially C-4) spectra were recorded in DMSO-d$_6$ but significant H$_2$O-peak were found in every spectra. It interfered in particular with the C$^\alpha$H-peak area and C$^\alpha$H(i)/C$^\alpha$H(j) cross-peaks were usually not found. Second main distraction was t$_1$-noise (Wüthrich, 1986, 52) which complicated especially NH/NH cross peak intensity determination.

A more detailed approach for each of our peptide will be discussed in the following sections. All following data were used with NOE-data as conformational constraint in structure calculations.

Conformation of the Peptides

A-1:

In all NMR-measurements of the A-1 mutated peptide, (A-1-4, Table 7) were used because its even better biological activity. A low temperature coefficient for amide protons of Tyr7 (3.4 ppb) and especially Ala8 (1.8 ppb) were detected, proposing that they are protected from the solvent (Table 6). The low 3.7 ppb/K (dδ/dT) (Table 6) of the amide proton of Tyr7 indicate the existence of β-turn. Tyr7 is a residue i+3 and Ser5 is in position i+1 of type II β-turn explaining why Ser5 has C$^\alpha$H chemical shift in the higher field in respect to random coil values. Strong NH(i)/NH(i+1) between Asn6 and Tyr7 and strong intraresidual C$^\alpha$H(i)/NH(i) for Asn6 and Tyr7 indicates type II β-turn. Conformation with turn residues 4-7 resembles structure of peptide B-2.

Strong C$^\alpha$H(i)/NH(i+1) NOE-correlation's were found between residues 2-6 indicating possible β-type/extended structure outside of turn area. Chemical shifts of C$^\alpha$H are pretty equal with random coil values (FIG. 1) between residues 2-4 and 8-10. Only between in residues Ser5, Asn6 and Tyr7 chemical shifts of C$^\alpha$H moved upfield supporting appearance of β-conformations in this part of peptide (49, 51). Medium NH(i)/NH(i+1) correlation between residues Phe9 and Cys10 shows evidence of α-conformation nearby disulphide bridge.

Relatively strong downfield shifting for NH was detected for Val2 and Cys10 indicating their solvent-exposing conformation. Strongly upfield shifted amide protons were found for residues 4-9 indicating their solvent-shielding (Table 6).

B-2:

First of all, our interest was focused on the very low temperature coefficient for amide proton of Tyr7 (0,7 ppm/K), indicating its solvent-shielded structure. That revealed hydrogen bonding between the amide proton of Tyr7 and usually a backbone carbonyl group. In a classical 1-turn, the temperature coefficient of the fourth residue in the turn should be lowered due to hydrogen bond formation with the carbonyl of the first residue in the turn. Also were found moderate temperature coefficient to Tyr9 NH (4.0 ppm/K). Strong downfield shifting for NH were detected for Val2 and Cys12 indicating their solvent-exposing conformation. Strongly upfield shifted amide protons were Asn6, Tyr7 and Tyr9 indicating their solvent-shielding (Table 6).

Figure 26A:
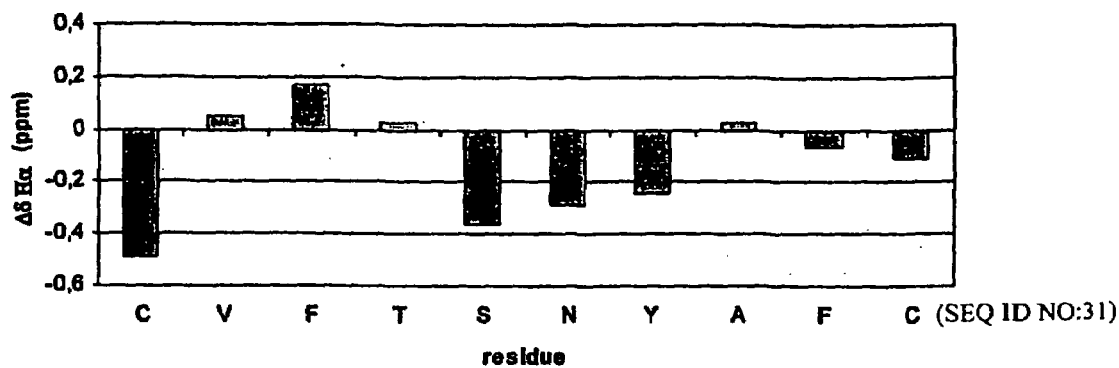
FIGS. 26a to c show plots of the differences between $C^{\alpha}H$ chemical shift values in the random coil and values determined experimentally in DMSO-$d_6$ for A-1 (a), B-2 (b) and C-4 (c).
Figure 26B:
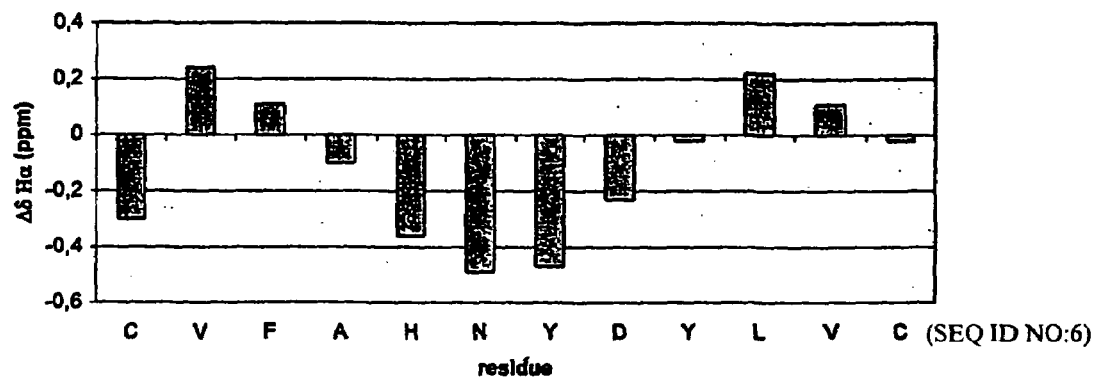
Figure 26C:
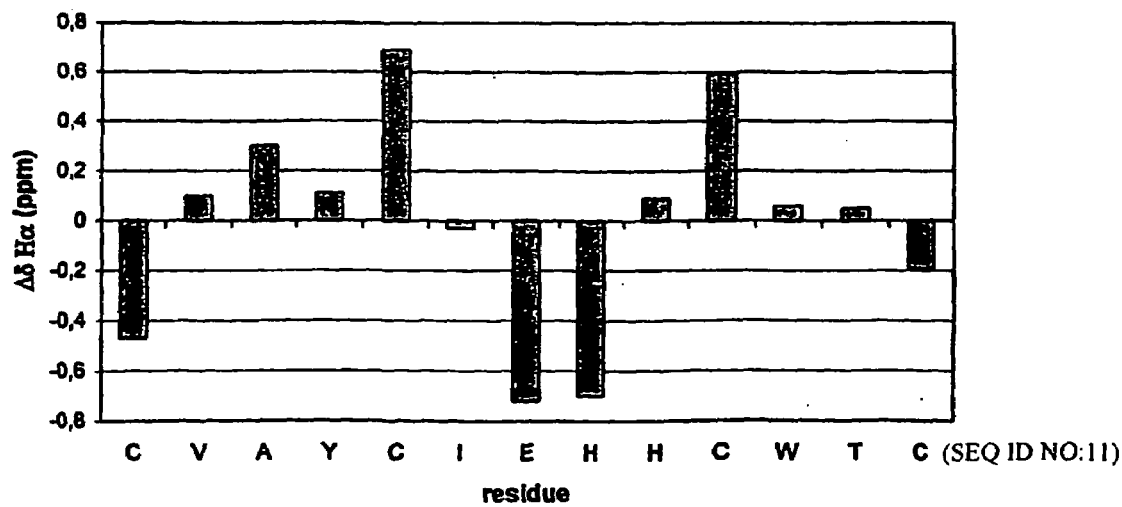

The strong NH(i)/NH(i+1) correlation's between residues His5-Asn6 and weak between Asn6-Tyr7 were found. This data appropriates to type 1 β-turn between residues 4-7 (52). Remarkable strong sequential C$^\alpha$H(i)/NH(i+1) correlation's between residues 1-4 and 9-12 and only medium or weak between residues 6-9 were as well detected. This reveals β-sheet type structure outside of 1-turn area. Further, weak NOE-correlation's between Ala4 C$^\beta$H$_3$-protons and Tyr7 and Tyr9 amide protons indicates type I β-turn (52). Chemical shifts of C$^\alpha$H are differs strongly to upfield from random coil values (FIG. 26) between residues 5-8 indicating turn area (49).

However, simultaneous strong or medium NH(i)/NH(i+1) and strong C$^\alpha$H(i)/NH(i+1) NOE-correlation's indicated the existence of conformational changes. NH(i)/NH(i+1)-correlation's were found between residues 7-8 and 8-9 (medium) and 9-10 and 11-12 (weak). Furthermore strong intraresidual C$^\alpha$H(i)/NH(i) correlation's indicates existence of α-conformation for Asp8 and Tyr9. Long range NOE-correlation's over peptide ring indicates however structural similarities between conformations. Remarkable NH(i)-NH(j) NOE-correlation's were found between Val2-Val11 and Ala4-Tyr9.

C-4:

The C-4-peptide differs from A-1 and B-2 peptides because of two disulphide bridges. Very low temperature coefficient for amide proton of His9 were detected and relatively low for Tyr4, Trp 11 and Cys 13. The amide proton of His9 is hydrogen bonded with carbonyl of Ile6 indicating existence of β-turn. The disulphide bridge between Cys5 and Cys10 made this part of peptide more rigid. Strong downfield shifting for NH were detected for Val2, Cys5, Ile6 and Cys10 and very strong for Glu7 and Trp11 indicating their solvent-exposed conformation. Strongly upfield shifted amide protons were Tyr4, His9 and Cys13 indicating their solvent-shielding (Table 6).

Turn type between residues Ile6-His9 were identified as type II β-turn. Both strong NH(i)/NH(i+1) correlation between His8-His9 and strong intraresidual C$^\alpha$H(i)/NH(i) correlation for His8 indicates type II turn. Very strong downfield shift for Glu7 NH shows its solvent-exposed conformation, which is intrinsic for type II turn. The NOE was found between Ile6 NH-Tyr9 NH indicating tight turn. Only conformational disagreement was weak NH(i)/NH(i+1) correlation between Glu7-His8 indicating fluctuation in turn area.

Chemical shifts of C$^\alpha$H for Glu7 and His8 were moved strongly upfield indicating turn area. Strong C$^\alpha$H(i)/NH(i+1) NOE-correlation's were found between residues 1-6 and 9-13 indicated β-conformation outside of β-turn area. Main disagreements were relatively strong NH(i)/NH(i+1) correlation between Val2-Ala3 and weak NH(i)/NH(i+1) correlation between Tyr4-Cys5, Ile6-Glu7 and Trp11-Thr12 indicating dynamic behaviour of backbone.

Some remarkable medium and long range NOE-correlation's were found. Remarkable well-defined NOE-cross peaks were detected between $C^\alpha H$ protons of Ala3 and Thr 12 and side chain protons of Tyr4 and Ile6. Moderated temperature coefficients of amide protons of Tyr4, Trp 11 and Cys 13 are consequences of the partial hydrogen bonding with carbonyl oxygen's of Trp11, Tyr4 and Val2 respectively.

The NMR-data proved bridge formation between Cys1-Cys13 and Cys5-Cys10, Strong NOE-cross peak were detected between $C^\alpha H$ protons in residues Cys5 and Cys10. Furthermore, the chemical shifts of $C^\alpha H$ protons in residues Cys5 and Cys10 moved interestingly downfield (Table 6). The chemical shift values can be explained by ring current effect of aromatic ring nearby these protons (Wüthrich, 1986, 52). Same behaviour can be detected for amide protons of Ile6 and Trp11. The aromatic ring which induced these shifts is the indole-ring of Trp11. The NOE were found between Ile6 HN-Trp11H5.

The Activity of Modified Peptides

The peptides with a PSA-peptide/PSA ratio above 1.1 was interpreted to be active, below 1.1 as inactive (Table 7).

Following modifications did not affect to the activity of peptides A-1, B-2 and C-4: The removal of the negative charge D→N in peptides A-1-4 and B-2-2 and E→Q in C-4-3. In the peptide A-1 the change F(9)→Y(9) (A-1-2) and A(8)→N(8) (A-1-3) did not affect to the activity. In the peptide B-2 the activity remained with the modification of Y(9)→A(9) (B-2-3). The sequences of A-1 and B-2 resemble each other despite of difference in length. When B-2 was shortened to 10 amino acids (B-2-4), the difference between the sequences is A(4)H(5) in B-2-4 vs. T(4)S(5) in A-1-3. In peptide C-4 the peptide with the modification of Y(4)→F(4) (C-4-3) was active.

The following modifications were inactive: In the peptide A-1 F(3)→Y(3) and both in the peptides A-1 and B-2 modification Y(7)→A(7). In the peptide C-4 modifications Y(4)→A(4) and W(11)→A(11) were inactive. In addition 10 amino acids sequence C-4-4 with one Cystein bond and C-4-6, cyclised by using peptide bonding, were inactive.

CONCLUSIONS

The sequences and the amino acid positions of the three peptides A-1, B-2 and C-4 are in Table 8. The two peptides A-1 and B-2 have similar structure and the same biological activity. The particularly important side chains in A-1 peptide are Phenylalanine (Phe) in position 3 and Tyrosine (Tyr) in position 7. In the peptide B-2 the corresponding amino acids are Phenylalanine (Phe) in position 3 and Tyrosine (Tyr) in position 7.

In sequences A-1 and B-2 the rigid β-turn stabilises the position of aromatic side chains of Phenylalanine (Phe) in position 3 and Tyrosine (Tyr) in position 7. The structure is stabilised in the peptide A-1 by hydrogen bond between the carbonyl oxygen of Threonine (Thr) in position 4 and the hydrogen of amide of Tyrosine (Tyr) in the position 7. The structure is stabilised in the peptide B-2 by the hydrogen bond between the carbonyl oxygen of Alanine (Ala) in position 4 and the hydrogen of the amide of Tyrosine (Tyr) in position 7.

The particularly important amino acids of the peptide C-4 are Tyrosine (Tyr) in position 4 and Tryptophan (Trp) in position 11. The structure is stabilised by the two disulphide bridges; the first between the positions Cys1 and Cys13 and second between the positions Cys5 and Cys10.

Figure 27A:
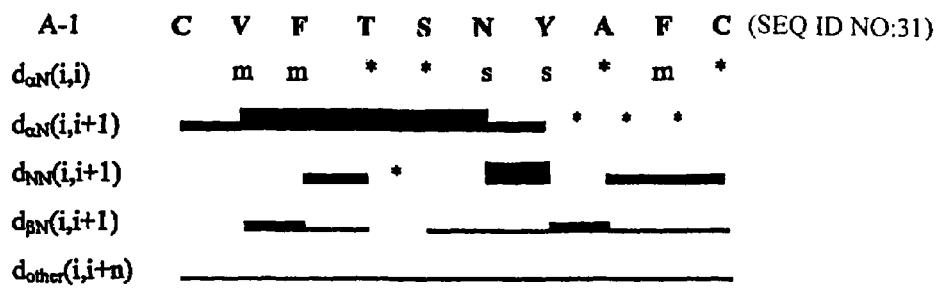
FIGS. 27a to c show the significant NOE-correlations of peptides A-1, B-2 and C-4 in DMSO-$d_6$
Figure 27B:
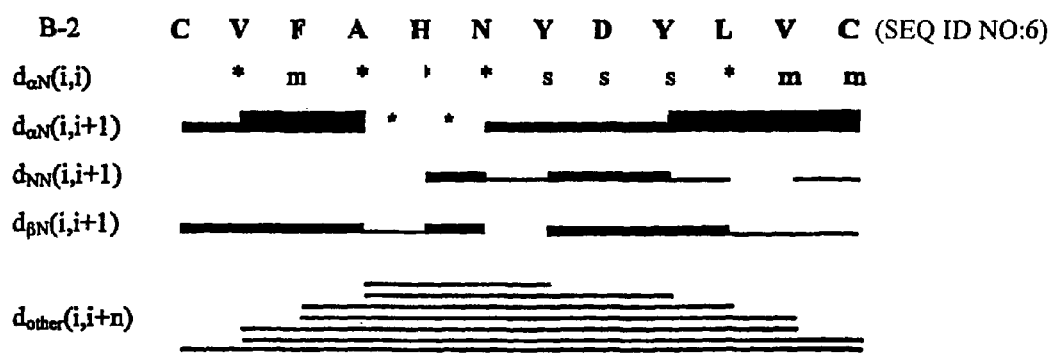
Figure 27C:
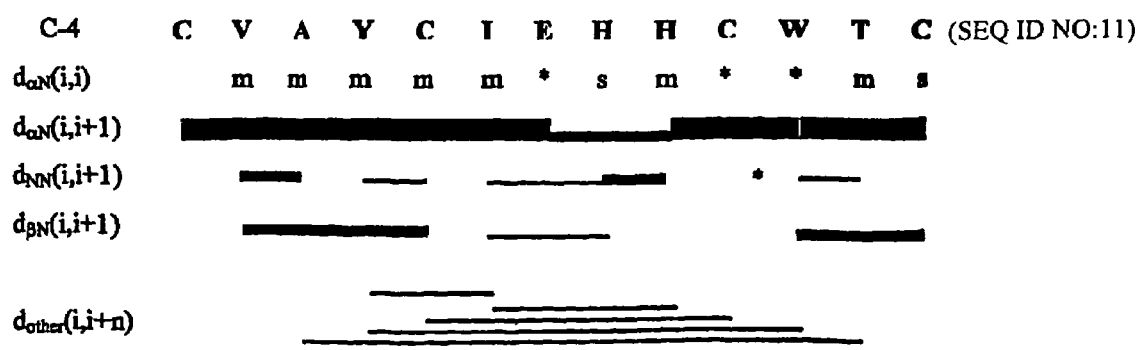

FIGS. 27a to 27c show the significant NOE-correlations of peptides A-1, B-2 and C-4 in DMSO-$d_6$. Relative cross-peak intensities were estimated from volume integration. Sings s and m mean relatively strong and medium intensities of intraresidual $d_{H\alpha NH}(i,i)$. Sing * mean disturbed NOE-correlation by some other NOE. NOEs indicated as "other" interaction include long range main chain-main chain, side chain-main chain or side chain-side chain interactions.

Figure 28:
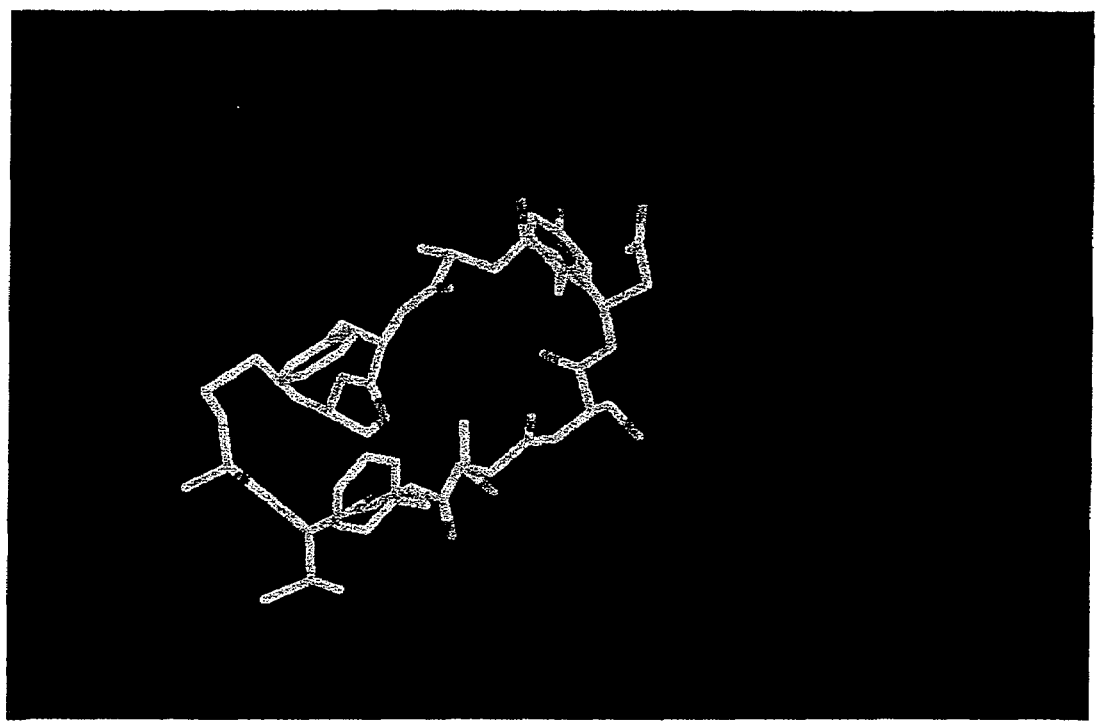
FIG. 28 shows the three-dimensional structure of the peptide A-1.
Figure 29:
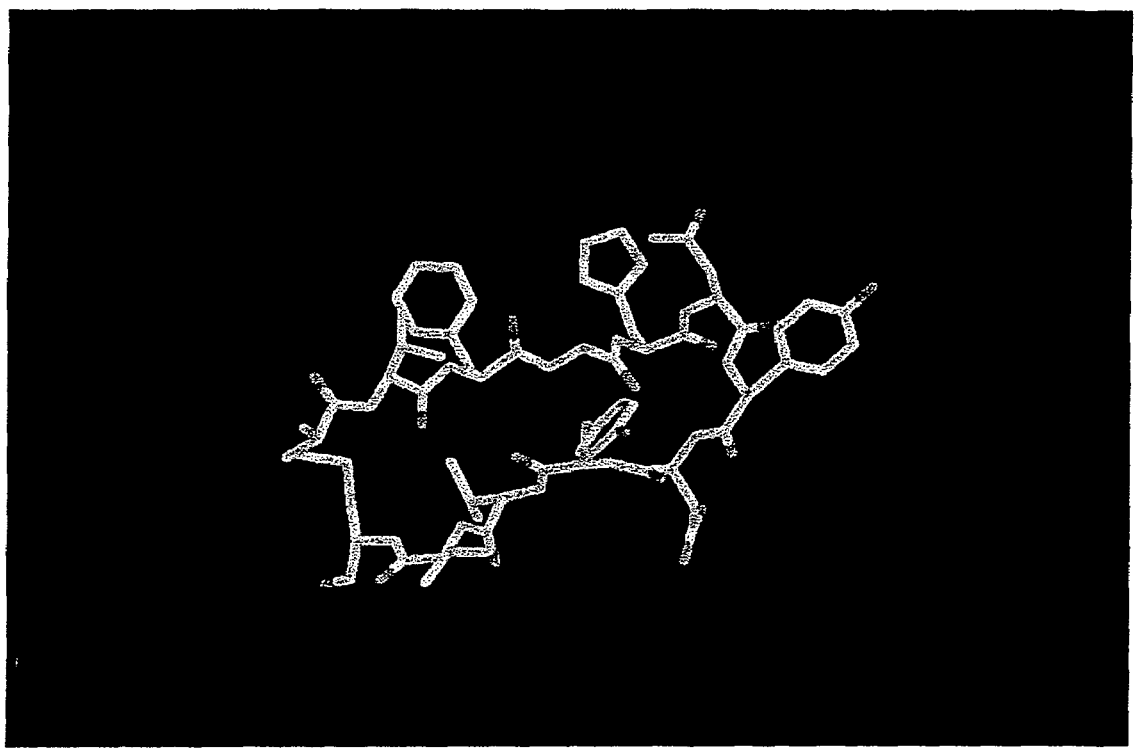
FIG. 29 shows the three-dimensional structure of the peptide B-2.
Figure 30:
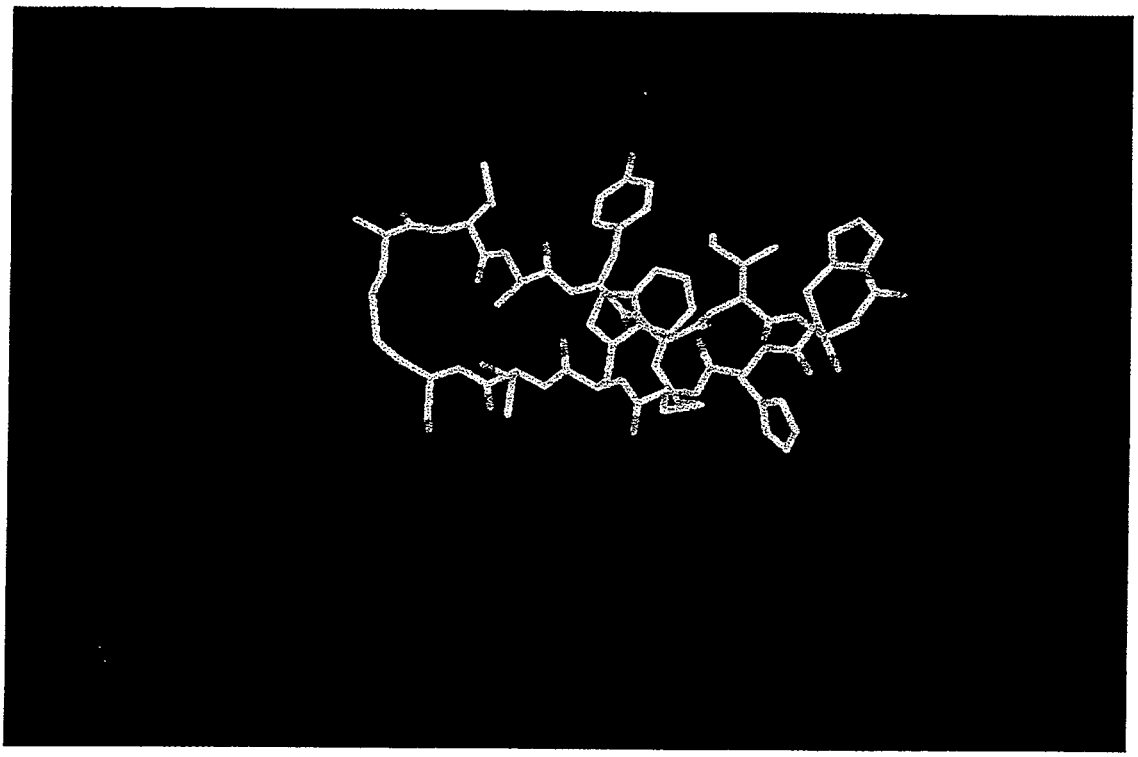
FIG. 30 shows the three-dimensional structure of the peptide C-4.

FIG. 28 shows a three-dimensional structure of the peptide A-1, FIG. 29 shows a three-dimensional structure of the peptide B-2 and FIG. 30 shows a three-dimensional structure of the peptide C-4. The structures have been calculated from the data given above and in the following tables.

TABLE 6

$^1$H chemical shifts and amide proton temperature coefficients of PSA-binding peptides

| Peptide Residue | NH | $C^\alpha H$ | $C^\beta H$ | $C^x H$ | $C^\delta H$ | Other | $-\Delta\delta/\Delta T$ (ppb/K) |
|---|---|---|---|---|---|---|---|
| A-1 | | | | | | | |
| Cys1 | | 4.20 | 2.98 | | | | |
| Val2 | 8.52 | 4.23 | 1.88 | 0,81 | | | 6.1 |
| Phe3 | 8.36 | 4.83 | 3.08, 2.88 | | 7.18 | 7.13-7.23 ($C^\epsilon H, C^\zeta H$) | 6.0 |
| Thr4 | 8.02 | 4.38 | 4.18 | 1,04 | | | 7.4 |
| Ser5 | 8.06 | 4.14 | 3.72, 3.65 | | | | 4.7 |
| Asn6 | 7.99 | 4.46 | 2.46, 2.39 | | | 6.93, 7.38 ($N^\delta H$) | 7.2 |
| Tyr7 | 7.81 | 4.36 | 2.86, 2.67 | | 6.94 | 6.62 ($C^\epsilon H$) | 3.7 |
| Ala8 | 7.89 | 4.37 | 1.09 | | | | 1.8 |
| Phe9 | 8.00 | 4.60 | 3.06, 2.82 | | | 7.13-7.23 ($C^\epsilon H, C^\zeta H$) | 7.0 |
| Cys10 | 8.48 | 4.58 | 3.17, 2.96 | | | | 7.5 |
| B-2 | | | | | | | |
| Cys1 | — | 4.39 | 3.03, 2.82 | | | | |
| Val2 | 8.62 | 4.42 | 2.07 | 0.87, 0.81 | | | 4.7 |
| Phe3 | 8.40 | 4.77 | 3.07, 2.73 | | 7.25 | 7.21-7.24 ($C^\epsilon H, C^\zeta H$) | 9.3 |
| Ala4 | 8.02 | 4.25 | 1.16 | | | | 7.6 |
| His5 | 8.42 | 4.27 | 3.13, 3.02 | | 7.27 (4H) | 8.81 ($C^\epsilon H$, 2H) | 8.7 |
| Asn6 | 7.99 | 4.26 | 2.59, 2.59 | | | 6.87, 7.44 ($N^\delta H$) | 5.0 |
| Tyr7 | 7.85 | 4.13 | 2.86, 2.75 | | 6.84 | 6.58 ($C^\epsilon H$) | 0.7 |
| Asp8 | 8.16 | 4.53 | 2.68, 2.50 | | | | 7.3 |
| Tyr9 | 7.53 | 4.58 | 2.94, 2.72 | | 6.94 | 6.57 ($C^\epsilon H$) | 4.0 |
| Leu10 | 8.30 | 4.50 | 1.35, 1.35 | 1.33 | 0.55, 0.53 | | 13.1 |

TABLE 6-continued

¹H chemical shifts and amide proton temperature coefficients of PSA-binding peptides

| Peptide Residue | NH | C$^\alpha$H | C$^\beta$H | C$^x$H | C$^\delta$H | Other | $-\Delta\delta/\Delta$T (ppb/K) |
|---|---|---|---|---|---|---|---|
| Val11 | 8.21 | 4.29 | 1.92 | 0.88, 0.87 | | | 10.8 |
| Cys12 | 8.75 | 4.67 | 3.21, 2.89 | | | | 10.3 |
| C-4 | | | | | | | |
| Cys1 | — | 4.22 | 3.23 | | | | |
| Val2 | 8.61 | 4.28 | 1.98 | 0.89, 0.88 | | | 6.7 |
| Ala3 | 8.15 | 4.65 | 1.20 | | | | 6.4 |
| Tyr4 | 7.96 | 4.71 | 2.87, 2.66 | | 6.89 | 6.53 (C$^\epsilon$H) | 4.5 |
| Cys5 | 8.67 | 5.38 | 2.83, 2.72 | | | | 9.9 |
| Ile6 | 8.55 | 4.20 | 1.81 | 1.14, 1.55 0.92 (C$^x$H$_3$) | 0.86 | | 6.5 |
| Glu7 | 8.98 | 3.57 | 2.17, 1.95 | 2.28 | | | 8.5 |
| His8 | 8.41 | 3.93 | 3.27 | | 7.24 (4H) | 8.74 (C$^\epsilon$H, 2H) | 5.9 |
| His9 | 7.86 | 4.72 | 3.04, 2.87 | | 7.18 (4H) | 8.63 (C$^\epsilon$H, 2H) | 1.0 |
| Cys10 | 8.60 | 5.27 | 2.74, 2.65 | | | | 9.1 |
| Trp11 | 8.58 | 4.76 | 3.09, 2.89 | | 7.14 (2H) | 7.65 (4H), 6.95 (5H), 6.98 (6H), 7.26 (7H), 10.62 (NH) | 4.3 |
| Thr12 | 8.20 | 4.40 | 3.94 | 1.10 | | | 10.3 |
| Cys13 | 7.97 | 4.50 | 3.17 | | | | 4.0 |

TABLE 7

The activity of the peptides A-1, B-2, C-4 and their modifications. The peptides with PSA-peptide/PSA ratio > 1.1 is interpreted to be active.

| Code | Peptide | Length | Sequence | PSA-peptide/ PSA ratio |
|---|---|---|---|---|
| A-1-1 | A-1 parent | 10 | CVFTSDYAFC (SEQ ID NO:1) | 2.3 |
| A-1-2 | A-1 N6Y9 | 10 | CVFTSNYAYC (SEQ ID NO:32) | 2.3 |
| A-1-3 | A-1 N6N8Y9 | 10 | CVFTSNYNYC (SEQ ID NO:33) | 1.9 |
| A-1-4 | A-1 N6 | 10 | CVFTSNYAFC (SEQ ID NO:34) | 2.4 |
| A-1-5 | A-1 Y39 | 10 | CVYTSDYAYC (SEQ ID NO:35) | 1.0 |
| A-1-6 | A1 N6Y7Y9 | 10 | CVFTSNAAYC (SEQ ID NO:36) | 1.0 |
| B-2-1 | B-2 parent | 12 | CVFAHNYDYLVC (SEQ ID NO:6) | 3.0 |
| B-2-2 | B-2 N8 | 12 | CVFAHNYNYLVC (SEQ ID NO:37) | 3.1 |
| B-2-3 | B-2 N8A9 | 12 | CVFAHNYNALVC (SEQ ID NO:38) | 2.6 |
| B-2-4 | B-2 10 N8 | 10 | CVFAHNYNYC (SEQ ID NO:39) | 1.9 |
| B-2-5 | B-2 A7 | 12 | CVFAHNANYLVC (SEQ ID NO:40) | 1.1 |
| C-4-1 | C4 parent | 13 | CVAYCIEHHCWTC (SEQ ID NO:11) | 2.1 |
| C-4-2 | C-4 F4 | 13 | CVAFCIEHHCWTC (SEQ ID NO:41) | 2.3 |
| C-4-3 | C-4 Q7 | 13 | CVAYCIQHHCWTC (SEQ ID NO:42) | 2.1 |
| C-4-4 | C-4 10A5Q7 | 10 | CVAYAIQHHC (SEQ ID NO:43) | 1.1 |
| C-4-5 | C-4 A4 | 13 | CVAACIEHHCWTC (SEQ ID NO:44) | 1.0 |
| C-4-6 | C-4 A11 | 13 | CVAYCIEHHCATC (SEQ ID NO:45) | 0.9 |
| C-4-7 | Cyclic with peptide pond | 11 | HHCWTVAYCIE \|_____\| (SEQ ID NO:46) | 0.8 |

TABLE 8

Synthetic peptides for NMR studies and their amino acid positions

| POSITION | 1 | 2 | 3 | 4 | 5 | 6 | 7 | 8 | 9 | 10 | 11 | 12 | 13 |
|---|---|---|---|---|---|---|---|---|---|---|---|---|---|
| A-1 (SEQ ID NO:31) | C | V | F | T | S | N | V | A | F | C | | | |
| B-2 (SEQ ID NO:6) | C | V | F | A | H | N | Y | D | Y | L | V | C | |
| C-4 (SEQ ID NO:11) | C | V | A | Y | C | I | E | H | H | C | W | T | C |

REFERENCES

1. Wang, M C, Valenzuela L A, Murphy G P, Chu T M. Purification of a human prostate specific antigen. Invest. Urol. 17, 1979, 159-163.
2. Lilja, H, Oldbrink J, Rannevik G, Laurell C-B. Seminal vesicle secreted proteins and their reactions during gelation and liquefaction of human semen. J. Clin. Invest 1987; 80:281-285.
3. Zhang, W M, Leinonen J, Kalkkinen N, Dowell B, Stenman U H. Purification and characterization of different molecular forms of prostate-specific antigen in human seminal fluid. Clin Chem 1995; 41:1567-73.
4. Stenman, U H, Leinonen J, Alfthan H, Rannikko S, Tuhkanen K, Alfthan O. A complex between prostate-specific antigen and alpha 1-antichymotrypsin is the major form of prostate-specific antigen in serum of patients with prostatic cancer: assay of the complex improves clinical sensitivity for cancer. Cancer Res 1991; 51:222-6.
5. Mikolajczyk, S D, Grauer L S, Millar L S, Hill T M, Kumar A, Rittenhouse H G, Wolfert R L, Saedi M S. A precursor form of PSA (PPSA) is a component of the free PSA in prostate cancer serum. Urology 1997; 50:710-4.
6. Chen, Z, Chen H, Stamey T A. Prostate specific antigen in benign prostatic hyperplasia: purification and characterization. J Urol 1997; 157:2166-70.

7. Zhang, W M, Finne P, Leinonen J, Vesalainen S, Nordling S, Rannikko S, Stenman U H. Characterization and immunological determination of the complex between prostate-specific antigen and alpha2-macroglobulin. Clin Chem 1998; 44:2471-9.

8. Fortier, A H, Nelson B J, Grella D K, Holaday J W. Anti-angiogenic activity of prostate-specific antigen. J Natl Cancer Inst 1999; 91:1635-40.

9. Heidtmann, H H, Nettelbeck D M, Mingels A, Jager R, Welker H G, Kontermann R E. Generation of angiostatin-like fragments from plasminogen by prostate-specific antigen. Br J Cancer 1999; 81:1269-73.

10. Adams, G P, Schier R. Generating improved single-chain Fv molecules for tumor targeting. J Immunol Methods 1999; 231:249-60.

11. Gersuk, G M, Corey M J, Corey E, Stray J E, Kawasaki G H, Vessella R L. High-affinity peptide ligands to prostate-specific antigen identified by polysome selection. Clin Invest Med 1997; 20:119-26.

12. Denmeade, S R, Lou W, Lovgren J, Malm J, Lilja H, Isaacs J T. Specific and efficient peptide substrates for assaying the proteolytic activity of prostate-specific antigen. Cancer Res 1997; 57:4924-30.

13. Denmeade, S R, Nagy A, Gao J, Lilja H, Schally A V, Isaacs J T. Enzymatic activation of a doxorubicin-peptide prodrug by prostate-specific antigen. Cancer Res 1998; 58:2537-40.

14. Arap, W, Pasqualini R, Ruoslahti E. Cancer treatment by targeted drug delivery to tumor vasculature in a mouse model [see comments]. Science 1998; 279:377-80.

15. Nargund, R P, Patchett A A, Bach M A, Murphy M G, Smith R G. Peptidomimetic growth hormone secretagogues. Design considerations and therapeutic potential. J Med Chem 1998; 41:3103-27.

16. Houghten, R A, Pinilla C, Appel J R, Blondelle S E, Dooley C T, Eichler J, Nefzi A, Ostresh J M. Mixture-based synthetic combinatorial libraries. J Med Chem 1999; 42:3743-78.

17. Harbottle, R P, Cooper R G, Hart S L, Ladhoff A, McKay T, Knight A M, Wagner E, Miller A D, Coutelle C. An RGD-oligolysine peptide: a prototype construct for integrin-mediated gene delivery [see comments]. Hum Gene Ther 1998; 9:1037-47.

18. Zalipsky, S, Puntambekar B, Boulikas P, Engbers C M, Woodle M C. Peptide attachment to extremities of liposomal surface grafted PEG chains: preparation of the long-circulating form of laminin pentapeptide, YIGSR. Bioconjug Chem 1995; 6:705-8.

19. Slepushkin, V A, Salem, I I, Andreev S M, Dazin P, Duzgunes N. Targeting of liposomes to HIV-1-infected cells by peptides derived from the CD4 receptor. Biochem Biophys Res Commun 1996; 227:827-33.

20. Rajotte, D, Arap W, Hagedom M, Koivunen E, Pasqualini R, Ruoslahti E. Molecular heterogeneity of the vascular endothelium revealed by in vivo phage display. Clin Invest 1998; 102:430-7.

21. Koivunen, E, Wang B, Dickinson C D, Ruoslahti E. Peptides in cell adhesion research. Methods Enzymol 1994; 245:346-69.

22. Koivunen, E, Huhtala M L, Stenman U H. Human ovarian tumor-associated trypsin. Its purification and characterization from mucinous cyst fluid and identification as an activator of pro-urokinase. J Biol Chem 1989; 264:14095-9.

23. Itkonen, O, Koivunen E, Hurme M, Alfthan H, Schroder T, Stenman U H. Time resolved immunofluorometric assays for trypsinogen-1 and 2 in serum reveal preferential elevation of trypsinogen-2 in pancreatitis. J Lab Clin Med 1990; 115:712-8.

24. Leinonen, J, Zhang W-M, Paus E, Stenman U-H. Reactivity of 77 antibodies to prostate specific antigen (PSA) with isoenzymes and complexes of PSA. Tumor Biol 1999; 20: Suppl 1:28-34.

25. Smith, D B, Johnson K S. Single-step purification of polypeptides expressed in *Escherichia coli* as fusions with glutathione S-transferase. Gene 1988; 67:31-40.

26. Leinonen, J, Lovgren T, Vomanen T, Stenman U H. Double-label time-resolved immunofluorometric assay of prostate-specific antigen and of its complex with alpha 1-antichymotrypsin. Clin Chem 1993; 39:2098-103.

27. Leinonen, J, Leinimaa M, Zhang W-M, Piironen T, Pettersson K, Lilja H, Dowell B, Stenman U-H. Reactivity of anti-PSA monoclonal antibodies with recombinant human kallikrein-2. Tumor Biol 1999; 20: Suppl 1:35-7.

28. Zhang, W-M, Leinonen J, Stenman U-H. Prostate specific antigen forms a complex with and cleaves alpha-1-protease inhibitor in vitro. Prostate 1997; 33:87-96.

29. Fisher, R J, Fivash M. Surface plasmon resonance based methods for measuring the kinetics and binding affinities of biomolecular interactions. Curr Opin Biotechnol 1994; 5:389-95.

30. Stenman, U H, Paus E, Allard W J, Andersson I, Andres C, Barnett T R, Becker C, Belenky A, Bellanger L, Pellegrino C M, Bormer O P, Davis G, Dowell B, Grauer L S, Jette D C, Karlsson B, Kreutz F T, van der Kwast T M, Lauren L, Leinimaa M, Leinonen J, Lilja H, Linton H J, Nap M, Hilgers J, et al. Summary report of the TD-3 workshop: characterization of 83 antibodies against prostate-specific antigen. Tumour Biol 1999; 20:1-12.

31. Lovgren, J, Piironen T, Overmo C, Dowell B, Karp M, Pettersson K, Lilja H, Lundwall A. Production of recombinant PSA and HK2 and analysis of their immunologic cross-reactivity. Biochem Biophys Res Commun 1995; 213:888-95.

32. Cohen, P, Graves H C, Peehl D M, Kamarei M, Giudice L C, Rosenfeld R G. Prostate-specific antigen (PSA) is an insulin-like growth factor binding protein-3 protease found in seminal plasma. J Clin Endocrinol Metab 1992; 75:1046-53.

33. Koistinen, H, Seppala M, Koistinen R. Different forms of insulin-like growth factor-binding protein-3 detected in serum and seminal plasma by immunofluorometric assay with monoclonal antibodies. Clin Chem 1994; 40:531-6.

34. Sottrup-Jensen, L. Alpha-macroglobulins: structure, shape, and mechanism of proteinase complex formation. J Biol Chem 1989; 264:11539-42.

35. Berg, J M, Shi Y. The galvanization of biology: a growing appreciation for the roles of zinc. Science 1996; 271:1081-5.

36. Katz, B A, Clark J M, Finer-Moore J S, Jenkins T E, Johnson C R, Ross M J, Luong C, Moore W R, Stroud R M. Design of potent selective zinc-mediated serine protease inhibitors. Nature 1998; 391:608-12.

37. Feng, S, Kasahara C, Rickles R J, Schreiber S L. Specific interactions outside the proline-rich core of two classes of Src homology 3 ligands. Proc Natl Acad Sci USA 1995; 92:12408-15.

38. Scott, J K, Smith G P. Searching for peptide ligands with an epitope library. Science 1990; 249:386-90.

39. Lilja, H, Abrahamsson P A, Lundwall A. Semenogelin, the predominant protein in human semen. Primary structure and identification of closely related proteins in the male accessory sex glands and on the spermatozoa. J Biol Chem 1989; 264:1894-900.
40. Coombs, G S, Bergstrom R C, Pellequer J L, Baker S I, Navre M, Smith M M, Tainer J A, Madison E L, Corey D R. Substrate specificity of prostate-specific antigen (PSA). Chem Biol 1998; 5:475-488.
41. Hemmila, I., Dakubu, S., Mukkala, V.-M., Siitari, H. & Löwgren, T. (1984). Europium as a label in time-resolved immunofluorometric assays. Anal. Biochem., 137, 335-343.
42. Karonen, S. L., Aronen, H., Liewendahl, K., Nikkinen, P., Mantyla, M. & Lindgren, J. (1988). Localization of human malignant tumors with radioiodinated recombinant tissue plasminogen activator. J Nucl Med, 29, 1194-9.
43. Laemmli, U. K. (1970). Cleavage of structural proteins during the assembly of the head of bacteriophage T4. Nature, 227, 680-5.
44. Towvbin, H., Staehelin, T. & Gordon, J. (1979). Electrophoretic transfer of proteins from polyacrylamide gels to nitrocellulose sheets: procedure and some applications. Proc Natl Acad Sci USA, 76, 4350-4.
45. Bax, A., and Davis, D. G. (1985), MLEV-17-based two-dimensional homonuclear magnetization transfer spectroscopy, *J. Magn. Reson.* 65, 355-360.
46. Güntert, P., Mumenthaler, C., Wüthrich, K. (1997). Torsion angle dynamics for NMR structure calculation with the new program DYANA. J. Mol. Biol. 273, 283-298.
47. Hutchinson, G., Thornton, J., M., (1994). A Revised Set of Potentials for β-turn Formation in Proteins, *Protein Science,* 3, 2207-2216.
48. Jeener, J., Meier, B. H., Bachmann, P. and Ernst, R. R., (1979). Investigation of exchance processes by two-dimensional NMR spectroscopy, J. Chem. Phys., 71, (11), 4546-4553.
49. Maynard, A., J., Sharman, G., J., Searle, M., S., (1998) Origin of β-hairpin Stability in Solution: Structural and Thermodynamic Analysis of Folding of a Model Peptide Supports Hydrophobic Stabilation in Water, *J. Am. Chem. Soc.,* 120, 1996-2007.
50. Raghothama, S., Chaddha, M., Balaram, P., (1996). NMR Analysis of a Conformational Transition in an Acyclic Peptide. Model System for Studying Helix Unfolding, *J. Phys. Chem.* 100, 19666-19671.
51. Wishart, D., S., Sykes, B., D., Richards, F., M., (1991), Relationship Between Nuclear Magnetic Resonance Chemical Shift and Protein Secondary Structure, *J. Mol. Biol.* 222, 311-333.
52. Wüthrich, K., (1986). NMR of Proteins and Nucleic Acids, Wiley-Interscience, New York.

The invention claimed is:

1. A peptide represented by formula (III):

$$CX^1X^2X^3CX^4X^5X^6X^7CX^8X^9C \quad (III),$$

wherein
 $X^1$ is V or A,
 $X^2$ is A, S, E, T, V or Q,
 $X^3$ is Y,
 each of $X^4$, $X^5$, $X^6$ and $X^7$ is independently any amino acid,
 $X^8$ is Y or W, and
 $X^9$ is V, T, M, Y, G or F,
wherein at least one pair of cysteines which are separated by at least two amino acids are interconnected by a disulfide bond to form a cyclic structure defined by the cysteines, intermediary amino acids and the disulfide bond, and wherein said peptide selectively binds to free prostate specific antigen.

2. The peptide of claim 1, wherein
 $X^1$ is V,
 $X^2$ is A or S,
 $X^8$ is Y or W,
 $X^9$ is V, T or Y, and
 each of $X^4$, $X^5$, $X^6$ and $X^7$ is independently selected from the group consisting of L, F, E, W, G, S, I, H, D, Q, Y, V, A, M and K.

3. The peptide of claim 1, wherein $X^1$ is V and $X^2$ is A.

4. The peptide of claim 1, wherein $X^5$ is E or Q.

5. The peptide of claim 1, selected from the group consisting of:
 CVSYCLFEFCYVC (SEQ ID NO: 8), CVEYCWEGSCYVC (SEQ ID NO: 9), CVAYCEEWECYVC (SEQ ID NO: 10), CVAYCIEHHCWTC (SEQ ID NO: 11), CVSYCDGLQCWMC (SEQ ID NO: 12), CVTYCYGEVCYYC (SEQ ID NO: 15), CAAYCVAGLCYGC (SEQ ID NO: 16), CVQYCIGGDCWFC (SEQ ID NO: 17), CVVYCDSMKCWTC (SEQ ID NO: 18) and CVAYCISSLCYYC (SEQ ID NO: 19).

6. The peptide of claim 1, wherein the peptide enhances the enzymatic activity of prostate specific antigen.

7. A protein comprising the peptide of any one of claims 1-6, wherein said protein selectively binds to free prostate specific antigen, and enhances its enzymatic activity.

8. A diagnostic composition comprising at least one peptide of any one of claims 1-6, and a diagnostically acceptable carrier and/or labeling substance.

9. A pharmaceutical composition comprising at least one peptide of any one of claims 1-6, and a pharmaceutically acceptable carrier.

* * * * *

UNITED STATES PATENT AND TRADEMARK OFFICE
CERTIFICATE OF CORRECTION

PATENT NO. : 7,414,023 B2  Page 1 of 1
APPLICATION NO. : 10/363662
DATED : August 19, 2008
INVENTOR(S) : Ulf-Hakan Stenman et al.

It is certified that error appears in the above-identified patent and that said Letters Patent is hereby corrected as shown below:

Please amend columns 3, 4 and 5 as follows:

Column 3, line 10, after backbone delete "5";

Column 3, line 22, delete "comprising" and insert --comprises--;

Column 3, line 34, delete "X1 is V, X2 is F, X~" and insert --$X^1$ is V, $X^2$ is F, $X^6$--;

Column 3, line 38, delete "X1 is V, X2 is 1, X6" and insert --$X^1$ is V, $X^2$ is I, $X^6$--;

Column 3, line 42, delete "art" and insert --an--;

Column 3, line 47, delete "Xs" and insert --$X^8$--;

Column 3, line 48, delete "beating" and insert --being--;

Column 3, line 52, delete "X9" and insert --$X^9$--;

Column 3, line 63, after $CX^1$ delete "X" and insert --$X^2$--;

Column 4, line 28, delete "5";

Column 4, line 33, delete "CVPYLOLWLC" and insert --CVPYLGLWLC--;

Column 5, line 5, after motif delete "10";

Column 5, line 30, delete "carder" and insert --carrier--;

Column 5, line 40, delete "is" and insert --are--

Signed and Sealed this

Twenty-seventh Day of January, 2009

JOHN DOLL
*Acting Director of the United States Patent and Trademark Office*

```
                         SEQUENCE LISTING

<160> NUMBER OF SEQ ID NOS: 29

<210> SEQ ID NO 1
<211> LENGTH: 10
<212> TYPE: PRT
<213> ORGANISM: Artificial Sequence
<220> FEATURE:
<223> OTHER INFORMATION: Prostate Specific Antigen Binding Peptide

<400> SEQUENCE: 1

Cys Val Phe Thr Ser Asp Tyr Ala Phe Cys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Prostate Specific Antigen Binding Peptide

<400> SEQUENCE: 2

Cys Val Ile Tyr Asp Gly Asn His Trp Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Prostate Specific Antigen Binding Peptide

<400> SEQUENCE: 3

Cys Ile Phe Glu Pro Asp Tyr Ser Tyr Cys
1               5                   10

<210> SEQ ID NO 4
<211> LENGTH: 10
<212> TYPE: PRT
<213> ORGANISM: Artificial Sequence
```

```
<220> FEATURE:
<223> OTHER INFORMATION: Prostate Specific Antigen Binding Peptide

<400> SEQUENCE: 4

Cys Val Phe Asp Asp Leu Tyr Ser Phe Cys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Prostate Specific Antigen Binding Peptide

<400> SEQUENCE: 5

Cys Thr Phe Ser Val Asp Tyr Lys Tyr Leu Met Cys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Prostate Specific Antigen Binding Peptide

<400> SEQUENCE: 6

Cys Val Phe Ala His Asn Tyr Asp Tyr Leu Val Cys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Prostate Specific Antigen Binding Peptide

<400> SEQUENCE: 7

Cys Arg Phe Asp Lys Glu Tyr Arg Thr Leu Val Cys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Prostate Specific Antigen Binding Peptide

<400> SEQUENCE: 8

Cys Val Ser Tyr Cys Leu Phe Glu Phe Cys Tyr Val Cys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Prostate Specific Antigen Binding Peptide

<400> SEQUENCE: 9

Cys Val Glu Tyr Cys Trp Glu Gly Ser Cys Tyr Val Cys
1               5                   10

<210> SEQ ID NO 10
<211> LENGTH: 13
<212> TYPE: PRT
<213> ORGANISM: Artificial Sequence
```

```
<220> FEATURE:
<223> OTHER INFORMATION: Prostate Specific Antigen Binding Peptide

<400> SEQUENCE: 10

Cys Val Ala Tyr Cys Glu Glu Trp Glu Cys Tyr Val Cys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Prostate Specific Antigen Binding Peptide

<400> SEQUENCE: 11

Cys Val Ala Tyr Cys Ile Glu His His Cys Trp Thr Cys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Prostate Specific Antigen Binding Peptide

<400> SEQUENCE: 12

Cys Val Ser Tyr Cys Asp Gly Leu Gln Cys Trp Met Cys
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Prostate Specfiic Antigen Binding Peptide

<400> SEQUENCE: 13

Cys Leu Ser Thr Cys Ala Gln Ser Cys Arg Ile Ser Cys
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Prostate Specfiic Antigen Binding Peptide

<400> SEQUENCE: 14

Cys Leu Leu Tyr Cys His Asp Ala Cys Trp Trp Val Cys
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Prostate Specific Antigen Binding Peptide

<400> SEQUENCE: 15

Cys Val Thr Tyr Cys Tyr Gly Glu Val Cys Tyr Tyr Cys
1               5                   10

<210> SEQ ID NO 16
<211> LENGTH: 13
<212> TYPE: PRT
<213> ORGANISM: Artificial Sequence
```

```
<220> FEATURE:
<223> OTHER INFORMATION: Prostate Specfiic Antigen Binding Peptide

<400> SEQUENCE: 16

Cys Ala Ala Tyr Cys Val Ala Gly Leu Cys Tyr Gly Cys
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Prostate Specfiic Antigen Binding Peptide

<400> SEQUENCE: 17

Cys Val Gln Tyr Cys Ile Gly Gly Asp Cys Trp Phe Cys
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Prostate Specific Antigen Binding Peptide

<400> SEQUENCE: 18

Cys Val Val Tyr Cys Asp Ser Met Lys Cys Trp Thr Cys
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Prostate Specific Antigen Binding Peptide

<400> SEQUENCE: 19

Cys Val Ala Tyr Cys Ile Ser Ser Leu Cys Tyr Tyr Cys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Prostate Specific Antigen Binding Peptide

<400> SEQUENCE: 20

Cys Val Trp Tyr Thr Gly Asn Thr Trp Cys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Prostate Specfiic Antigen Binding Peptide

<400> SEQUENCE: 21

Cys Val Phe Asp Ala Leu Tyr Thr Phe Cys
1               5                   10

<210> SEQ ID NO 22
<211> LENGTH: 10
<212> TYPE: PRT
<213> ORGANISM: Artificial Sequence
```

```
<220> FEATURE:
<223> OTHER INFORMATION: Prostate Specific Antigen Binding Peptide

<400> SEQUENCE: 22

Cys Val Ile Tyr Pro Gly Asn Val Trp Cys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Prostate Specific Antigen Binding Peptide

<400> SEQUENCE: 23

Cys Ile Phe Asp Gly Phe Trp Ile Leu Cys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Prostate Specific Antigen Binding Peptide

<400> SEQUENCE: 24

Cys Val Pro Tyr Leu Gly Leu Trp Leu Cys
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Prostate Specfiic Antigen Binding Peptide

<400> SEQUENCE: 25

Cys Met Phe Asp Pro Met Tyr Met Trp Met Thr Cys
1               5                   10

<210> SEQ ID NO 26
<211> LENGTH: 21
<212> TYPE: DNA
<213> ORGANISM: Artificial Sequence
<220> FEATURE:
<223> OTHER INFORMATION: Sequencing Primier

<400> SEQUENCE: 26
ccctcatagt taagcgtaac g                                              21

<210> SEQ ID NO 27
<211> LENGTH: 29
<212> TYPE: DNA
<213> ORGANISM: Artificial Sequence
<220> FEATURE:
<223> OTHER INFORMATION: PCR Primer

<400> SEQUENCE: 27
aggctcgagg atcctcggcc gacggggct                                      29

<210> SEQ ID NO 28
<211> LENGTH: 27
<212> TYPE: DNA
<213> ORGANISM: Artificial Sequence
<220> FEATURE:
<223> OTHER INFORMATION: PCR Primer
```

```
-continued

<400> SEQUENCE: 28
aggtctagaa ttcgccccag cggcccc                                          27

<210> SEQ ID NO 29
<211> LENGTH: 5
<212> TYPE: PRT
<213> ORGANISM: Artificial Sequence
<220> FEATURE:
<223> OTHER INFORMATION: Prostate Specific Antigen Binding Peptide

<400> SEQUENCE: 29

Cys Val Ala Tyr Cys
  1               5
```